(12) United States Patent
Carreira et al.

(10) Patent No.: US 7,544,667 B2
(45) Date of Patent: Jun. 9, 2009

(54) HYPOCHOLESTEROLEMIC COMPOUNDS

(75) Inventors: Erick Carreira, Zumikon (CH); Helmut Hauser, Uerikon (CH); Lisbet Kvaerno, Zürich (CH); Tobias Ritter, Zürich (CH); Moritz Werder, Bremgarten (CH)

(73) Assignee: Lipideon Biotechnology AG, Uerikon (CH)

( * ) Notice: Subject to any disclaimer, the term of this patent is extended or adjusted under 35 U.S.C. 154(b) by 0 days.

(21) Appl. No.: 10/575,025

(22) PCT Filed: Sep. 15, 2004

(86) PCT No.: PCT/CH2004/000584

§ 371 (c)(1),
(2), (4) Date: Apr. 25, 2007

(87) PCT Pub. No.: WO2005/033100

PCT Pub. Date: Apr. 14, 2005

(65) Prior Publication Data
US 2007/0275909 A1     Nov. 29, 2007

(30) Foreign Application Priority Data
Oct. 7, 2003 (EP) .................................. 03405719

(51) Int. Cl.
*A61K 31/70*    (2006.01)
*A61K 31/7028*    (2006.01)
*A61K 31/7042*    (2006.01)
*A61K 31/421*    (2006.01)
*A61K 31/397*    (2006.01)
*C07D 207/00*    (2006.01)
*C07D 205/00*    (2006.01)

(52) U.S. Cl. ............... 514/25; 514/23; 514/210.01; 514/210.02; 514/376; 514/379; 514/461; 536/4.1; 548/952

(58) Field of Classification Search .............. 514/25, 514/210.01, 210.02, 403, 23, 376, 379, 461; 536/4.1; 548/952
See application file for complete search history.

(56) References Cited

U.S. PATENT DOCUMENTS

| | | | |
|---|---|---|---|
| 5,306,817 | A | 4/1994 | Thiruvengadam et al. |
| 5,631,365 | A | 5/1997 | Rosenblum et al. |
| 5,633,246 | A | 5/1997 | McKittrick et al. |
| 5,756,470 | A | 5/1998 | Yumibe et al. |
| 6,593,078 | B1 | 7/2003 | Altmann et al. |
| 2003/0105028 | A1 | 6/2003 | Ghosal et al. |
| 2003/0119428 | A1 | 6/2003 | Davis et al. |
| 2003/0119809 | A1 | 6/2003 | Davis et al. |

FOREIGN PATENT DOCUMENTS

| | | |
|---|---|---|
| DE | 3620467 | 1/1987 |
| WO | WO 97/16455 | 5/1997 |

OTHER PUBLICATIONS

STN abstract of Van Heek et al. (Journal of Pharmacology and Experimental Therapeutics (1997), 283(1), pp. 157-163) (Abstract Sent).*

Rosenblum et al. (Journal of Medicinal Chemistry (1998) 41, pp. 973-980).*

Dugar et al. Bioorganic & Medicinal Chemistry Letters (1995), 5(24), 2947-52 (Abstract Sent).*

Mukerjee, Arya K. et al., "Rapid Synthesis of Dehydropeptides Carrying a β Lactam Moiety," J. Chem. Research (S), 1993, pp. 280-281, No. 7, London, Great Britain.

Van Heek, Margaret et al., "In vivo Metabolism-Based Discovery of a Potent Cholesterol Absorption Inhibitor . . . " JPET, 1997, pp. 157-163, vol. 283, No. 1.

Wu, George Guangzhong, "A Concise Asymmetric Synthesis of a β-Lactam-Based Cholesterol Absorption Inhibitor," Organic Process Research & Development, 2000, pp. 298-300, vol. 4.

Udupi, R. H. et al., "Synthesis of 1-(2'-carboxy-5'-nitrophenyl)-3,4-substituted azetidin-2-ones . . . " Indian Journal of Heterocyclic Chem., Oct.-Dec. 1996, pp. 99-102, vol. 6.

Clader, John W. et al., "2-Azetidinone Cholesterol Absorption Inhibitors: Structure-Activity Relationships . . . " J. Med. Chem., 1996, pp. 3684-3693, vol. 39, No. 19.

Otto, Hans-Hartwig et al., "Stereochemie der Dehydratisierung und Halogenierung der αR* . . . " Liebigs Ann. Chem., 1983, pp. 1162-1168, Verlag Chemie GmbH, Weinheim, Germany.

Browne, Margaret et al., "Trans Diastereoselective Synthesis of 3-Alkyl Substituted β-Lactams via the Acid . . . " Tetrahedron Letters, 1995, pp. 2555-2558, vol. 36, No. 15.

Bose, Ajay K. et al., "Microwave-Assisted Rapid Synthesis of α-Amino-β-Lactams . . . " Tetrahedron Letters, 1996, pp. 6989-6992, vol. 37, No. 39.

(Continued)

*Primary Examiner*—Shaojia Anna Jiang
*Assistant Examiner*—Michael C Henry
(74) *Attorney, Agent, or Firm*—The Webb Law Firm

(57) ABSTRACT

The present invention relates to novel hypocholesterolemic compounds of formula (I) useful in the treatment and prevention of atherosclerosis and for the reduction of cholesterol levels as well as to pharmaceutical compositions comprising said compounds alone or in combination with other active agents.

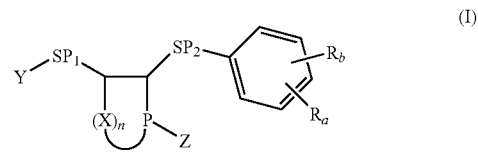

18 Claims, No Drawings

OTHER PUBLICATIONS

Van Leusen, Albert M. et al., "Base-Induced Cycloaddition of Sulfonylmethyl Isocyanides to C,N Double Bonds . . . " J. Org. Chem., 1977, pp. 1153-1159, vol. 42, No. 7.

Burnett, Duane A. et al., "Synthesis of 3-(1-Hydroxyethyl)-2-azetidinones via Ester-Imine Condensations," J. Org. Chem., 1985, pp. 5120-5123, vol. 50, No. 25.

Burnett, Duane A. et al., "2-Azetidinones as Inhibitors of Cholesterol Absorption," Journal of Medicinal Chemistry, Jun. 10, 1994, pp. 1733-1736, vol. 37, No. 12.

Rosenblum, Stuart B. et al., "Synthesis of 3-Arylpropenyl, 3-Arylpropynyl and 3-Arylpropyl 2-Azetidinones as Cholesterol Absorption . . . " Tetrahedron, 2000, pp. 5735-5742, vol. 56.

Kirkup, Michael P. et al., "(-)-SCH 57939: Synthesis and Pharmacological Properties of a Potent, Metabolically . . . " Bioorg. Med. Chem. Lett., 1996, pp. 2069-2072, vol. 6, No. 17.

Otto, Hans-Hartwig et al., "Darstellung und Stereochemie von 3-(α-Hydroxybenzyl)-1,4-diphenyl . . . " Liebigs Ann. Chem., 1983, pp. 1152-1161, Verlag Chemie GmbH, Weinheim, Germany.

Rosenblum, Stuart B. et al., "Discovery of 1-(4-Fluorophenyl)-(3R)-[3-(4-fluorophenyl)-(3S)-hydroxypropyl]-(4S) . . . " J. Med. Chem., 1998, pp. 973-980, vol. 41, No. 6.

Burnett, Duane A. et al., "Synthesis of Fluorescent Biochemical Tools Related to the 2-Azetidinone Class . . . " Bioorg. Med. Chem. Lett., 2002, pp. 315-318, vol. 12, No. 3.

Burnett, Duane A. et al., "Synthesis of Iodinated Biochemical Tools Related to the 2-Azetidinone Class . . . " Bioorg. Med. Chem. Lett., 2002, pp. 311-314, vol. 12, No. 3.

* cited by examiner

HYPOCHOLESTEROLEMIC COMPOUNDS

The present invention relates to novel hypocholesterolemic compounds useful in the treatment and prevention of atherosclerosis and for the reduction of cholesterol levels as well as to pharmaceutical compositions comprising said compounds alone or in combination with other active agents.

Atherosclerotic coronary heart disease represents the major cause for death and cardiovascular morbidity in the western world. Risk factors for atherosclerotic coronary heart disease include hypertension, diabetes mellitus, family history, male gender, cigarette smoke as well as serum cholesterol. Elevated concentrations of serum cholesterol have been demonstrated by a number of clinical studies to be a major contributing factor in the development and progression of atherosclerosis, which is characterized by the formation of cholesterol-containing plaques in the aorta and lesser arteries.

In mammals, ⅓ of the serum cholesterol is derived from exogenous dietary sources which enters the body through absorption in the intestine and ⅔ of the serum cholesterol are derived through endogenous de novo synthesis in the liver involving a complex set of enzyme-catalyzed reactions and regulatory mechanisms.

Recently it has been shown that intestinal cholesterol absorption is an energy-independent, protein-mediated process (Hauser, H. et al, *Biochemistry* 1998, 37, 17843-17850; Schulthess, G. et al, *Biochemistry* 2000, 39, 12623-12631; Werder, M. et al, *Biochemistry* 2001, 40, 11643-11650) rather than a passive diffusion process. The proteins facilitating intestinal cholesterol absorption were identified as two brush border membrane-resident scavenger receptors (Hauser, H. et al, *Biochemistry* 1998, 37, 17843-17850; Werder, M. et al, *Biochemistry* 2001, 40, 11643-11650). Both in vitro and in vivo animal experiments confirmed the presence of these two scavenger receptors in the intestinal BBM and proved that they are responsible for the protein-mediated cholesterol uptake.

Various 2-azetidinone compounds have been reported as being useful in lowering cholesterol and/or in inhibiting the formation of cholesterol-containing lesions in mammalian arterial walls: For example WO 93/02048, WO 94/17038, WO 95/08532, PCT/US95/03196, U.S. Pat. No. 5,633,246 describe 2-azetidinone compounds with different substituents at the 3-position, and U.S. Pat. No. 5,756,470 discloses 2-azetidinones having varying substituents at the 4 position. Other azetidinone derivatives include for example elastase inhibitory substituted azetidinones disclosed in European Patent 199,630B1 and European Patent Application 337,549A1. The most prominent representative of these 2-azetidinones, Ezetimibe (also known under trade names Zetia™ and Ezetrol®), has been in use as a cholesterol-lowering drug in monotherapy and in dual therapy combined with a statin. It is the first representative of the new class of cholesterol-lowering drugs that inhibit intestinal cholesterol absorption by targeting the two scavenger receptors in the intestinal brush border membrane described above.

However, it has been shown that the 2-azetidinones upon administration are readily absorbed and extensively metabolized into the pharmalogically active glucuronide of which over 95% remained in the intestinal wall upon direct administration as the glucuronide (van Heek, M. et al. *Br. J. Pharmacol.* 2000, 129, 1748-1754). In addition side effects such as allergic reactions including rash and angioedema have been reported.

Applicants have now discovered that the compounds of the present invention with the structural characteristics as depicted in formula I and in particular formulas II and III are able to inhibit the protein-mediated process mentioned above by which cholesterol absorption is mediated, while overcoming the above described disadvantages of compounds known in the art. Thus the compounds of the present invention are particularly useful in the treatment and prevention of atherosclerosis and for the reduction of cholesterol levels.

In a first aspect, the present invention thus relates to novel hypocholesterolemic compounds of formula I, and in particular to compounds of formulas II and III having a four- or five-membered ring, respectively.

In one embodiment, the present invention is directed to a compound of formula I, or a pharmaceutically acceptable salt or solvate thereof,

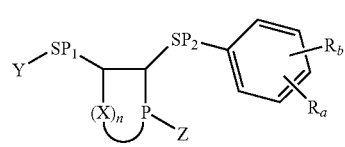

wherein

P represents —N< or —C=,

X represents independently of each other —CH$_2$—, CR$_1$ (sp$_2$-hybridised), O, —NH—, =N—, —CO— or —CS—, wherein R$_1$ represents H or NR$_2$, wherein R$_2$ represents H or lower alkyl, which optionally is linked to Z such that a bicyclic structure is formed;

n represents 1 or 2,

R$_a$ represents H, lower alkyl, —OR$_3$, —O(CO)R$_3$, —O(CO)OR$_3$, —O(CO)NR$_3$R$_4$, —NR$_3$R$_4$, —NR$_3$(CO)R$_4$, —COOR$_3$, —CONR$_3$R$_4$, —CH=CHCOOR$_3$, —CF$_3$, —CN, —NO$_2$, SO$_3$H, PO$_3$H or halogen, wherein R$_3$ and R$_4$ represent H or lower alkyl, R$_b$ represents H, OH, —OSO$_2$Me, —OSO$_2$W wherein W represents optionally substituted aryl or heteroaryl, —OCO(CHOH)$_2$COOR$_5$ wherein R$_5$ represents H or lower alkyl; or represents the formula -Sp$_3$-R$_6$, wherein Sp$_3$ represents a covalent bond, —O—, —OCH$_2$—, —OSO$_2$CH$_2$—, —OSO$_2$—, —OSO$_2$—(p)C$_6$H$_4$O— and R$_6$ represents one of carbohydrate structures A-D:

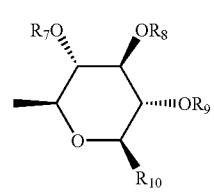

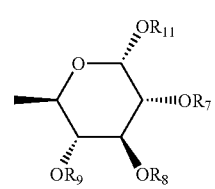

-continued

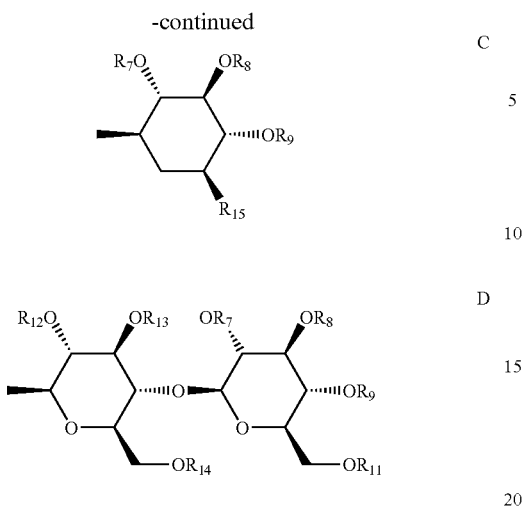

wherein $R_7$, $R_8$, $R_9$, $R_{11}$, $R_{12}$, $R_{13}$ and $R_{14}$ represent independently of each other H, lower alkyl, aryl(lower alkyl), —CO-lower alkyl, —CO-aryl, —SO$_3^-$ or —PO$_3^-$, $R_{10}$ represents —CH$_2$OR$_{16}$ or —COOR$_{17}$, and $R_{15}$ represents —CH$_2$OR$_{16}$, —COOR$_{17}$, —CH$_2$NH$_2$, —CH$_2$OPO$_3^-$ or —CH$_2$OSO$_3^-$, wherein $R_{16}$ and $R_{17}$ independently of each other represent H, lower alkyl, aryl(lower alkyl), —CO-lower alkyl, —CO-aryl, —SO$_3^-$ or —PO$_3^-$, Z represents optionally substituted aryl or heteroaryl, Sp$_1$ represents a spacer unit, such as a straight-chain or branched lower alkyl group —(CH$_2$)$_p$—, wherein p is from 2-6, which is unsubstituted, mono or poly-substituted by —OH, —OR$_{18}$, halogen or cyano group, wherein one or more —CH$_2$— groups may independently be replaced by —O—, —CO—, —CO—O—, —O—CO—, —NR$_{19}$—, —NR$_{19}$—CO—, —CO—NR$_{19}$—, —CH=CH—, —C≡C— and wherein R$_{18}$ and R$_{19}$ represent a hydrogen atom or lower alkyl;

Sp$_2$ represents an optional spacer unit, such as a covalent bond or a straight-chain or branched lower alkyl group —(CH$_2$)$_q$—, wherein q is from 1-6, which is unsubstituted, mono or poly-substituted by —OH, —OR$_{20}$, halogen or cyano group, wherein one or more —CH$_2$— groups may independently be replaced by —O—, —CO—, —CO—O—, —O—CO—, —NR$_{21}$—, —NR$_{21}$—CO—, —CO—NR$_{21}$—, —CH=CH—, —C≡C— and wherein R$_{20}$ and R$_{21}$ represents a hydrogen atom or lower alkyl;

Y represents optionally substituted aryl or heteroaryl, with the proviso, that if P=—N<, n=1, X=—CO— and Sp$_2$ represents a covalent bond, R$_6$ may not represent carbohydrate structures A or D for Sp$_3$=—O— and R$_6$ may not represent carbohydrate B for Sp$_3$=—OCH$_2$—.

Preferably, if P=—N<, n=1, X=—CO— and Sp$_2$ represents a covalent bond, R$_b$ may not represent H or OH and Sp$_3$ may not represent a covalent bond, —O— or —OCH$_2$—.

In a preferred embodiment, the present invention is directed towards compounds of formula I wherein P=—N<, n=1 and X=—CO—, —CS—, —CH$_2$— or —NH—.

Thus, the present invention is preferably directed towards compounds of formula IIa-d

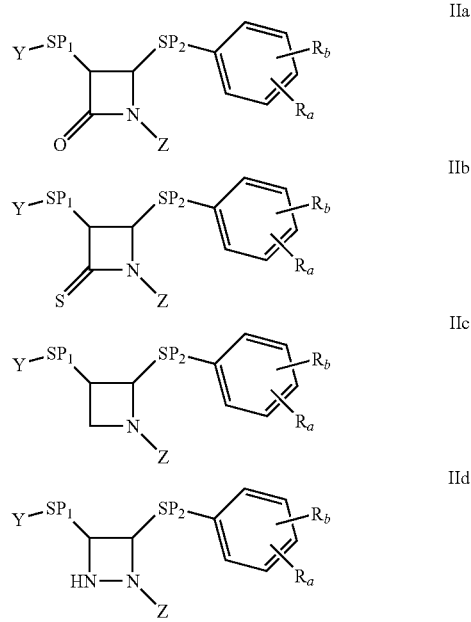

or a pharmaceutically acceptable salt or solvate thereof, wherein the groups R$_a$, R$_b$, Sp$_1$, Sp$_2$, Y and Z are as defined above.

In another preferred embodiment, the present invention is directed towards compounds of formula I wherein for P=—N<, —(X)$_n$— represents —OOC—, —COO—, —CONH—, —CH=N—, and for P=—C=, —(X)$_n$— represents —NH—N= or —O—N=.

Thus, the present invention is directed towards compounds of formula IIIa-f:

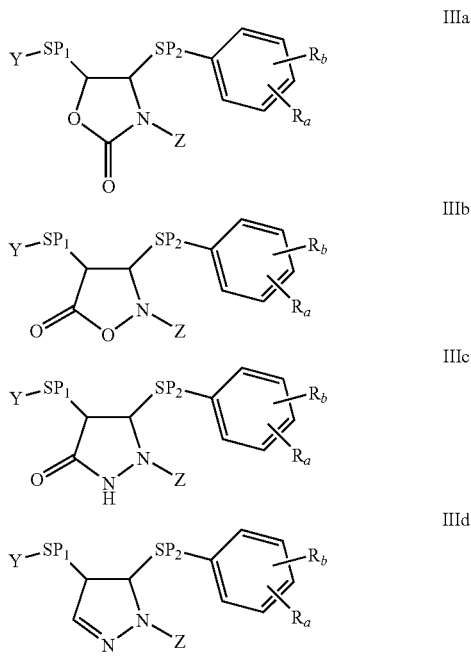

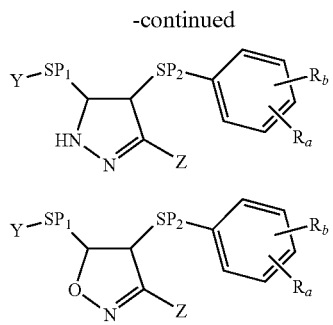

IIIe

IIIf or a pharmaceutically acceptable salt or solvate thereof, wherein the groups $R_a$, $R_b$, $Sp_1$, $Sp_2$, Y and Z are as defined above.

In a further preferred embodiment, the present invention is directed towards compounds of formula I with $P=$—$N<$ where —$(X)_n$— represents —CH—C=NR— or —CH—NH—CR— or wherein ring Z is coupled to —$(X)_n$— to form bicyclic compounds.

Thus, the present invention is further directed towards compounds of formula IIIg-h:

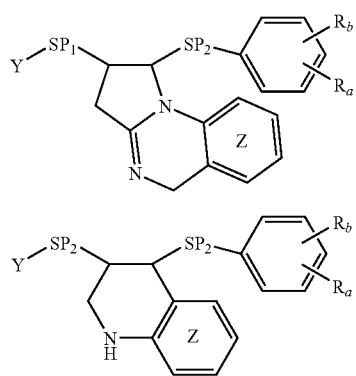

IIIg

IIIh $R_a$ preferably represents H, lower alkyl, —$OR_3$, —$NR_3R_4$, —$COOR_3$, —$CONR_3R_4$, —CH=$CHCOOR_3$, —$CF_3$, —CN, —$NO_2$, $SO_3H$, $PO_3H$ or halogen, more preferably H, lower alkyl, —$OR_3$, —$NR_3R_4$, —$COOR_3$, —$CONR_3R_4$ or halogen, most preferably H, lower alkyl, —$OR_{19}$ or halogen, wherein $R_3$ and $R_4$ represent independently of each other H or lower alkyl.

$R_b$ preferably represents H, OH, —$OSO_2Me$, —$OSO_2W$ wherein W represents Phenyl (Ph) or isomers of salicylic acid (all combinations of disubstituted phenyl with OH and COOH substituents); or the formula -$Sp_3$-$R_6$, wherein $Sp_3$ preferably represents a covalent bond, —O—, —$OCH_2$— or —$OSO_2CH_2$— and $R_6$ represents one of carbohydrate structures A-D, preferably carbohydrate structures A, B or D. More preferably $R_b$ represents H, OH, —$OSO_2Me$, —$OSO_2Ph$; or the formula -$Sp_3$-$R_6$, wherein $Sp_3$ preferably represents a covalent bond, —O—, —$OCH_2$— or —$OSO_2CH_2$— and $R_6$ represents one of carbohydrate structures A-D, preferably carbohydrate structures A, B or D.

$Sp_1$ preferably represents a straight-chain or branched —$(CH_2)_m$— group, which is unsubstituted, mono or poly-substituted by —OH, —$OR_{18}$, halogen or cyano group, wherein $R_{18}$ represents hydrogen or lower alkyl and m is 1 to 3. More preferably $Sp_1$ represents a —$(CH_2)_3$—, which is unsubstituted or substituted by —OH or halogen.

$Sp_2$ preferably represents a straight-chain or branched —$(CH_2)_p$— group, which is unsubstituted, mono or poly-substituted by —OH, —$OR_{20}$, halogen or cyano group, wherein $R_{20}$ represents hydrogen or lower alkyl and p is 1 to 3. More preferably $Sp_1$ represents an unsubstituted —$(CH_2)_p$—, wherein p is 1 to 3, most preferably a covalent bond.

$R_{15}$ preferably represents —$CH_2OR_{16}$, —$COOR_{17}$ or —$CH_2NH_2$, wherein $R_{16}$ and $R_{17}$ independently of each other represent H, lower alkyl, aryl(lower alkyl), —CO-lower alkyl, —CO-aryl, —$SO_3^-$ or —$PO_3^-$, preferably H, acetyl or benzyl.

$R_7$, $R_8$, $R_9$, $R_{11}$, $R_{12}$, $R_{13}$, and $R_{14}$ preferably represent independently of each other H, lower alkyl, aryl-lower alkyl, —CO-lower alkyl, —CO-aryl, more preferably, H, acetyl or benzyl.

The term "optionally substituted aryl group" should be understood to include an aromatic ring system having 4 to 10, preferably 5, 6 or 10 ring atoms. The aryl group can be substituted with one or more substituents, which may be the same or different, and are selected from a group as defined hereinafter. Non-limiting examples of suitable aryl groups include phenyl, naphthalene or tetraline groups, most preferably phenyl groups substituted by halogeno, preferably fluoro.

The term "optionally substituted heteroaryl" should be understood to include an aromatic ring system of 5 to 14, preferably 5 to 10, more preferably 5 to 6 or 10 ring atoms, in which one or more of the atoms in the ring system is/are atoms other than carbon, for example nitrogen, oxygen or sulfur. The heteroaryl can be optionally substituted by one or more substituents, which may be the same or different, and are selected from a group as defined hereinafter. Examples of suitable 6-membered heteroaryl groups include pyridyl, pyrimidinyl, pyrazinyl, pyridazinyl and the like. Examples of useful 5-membered heteroaryl rings include furyl, thienyl, pyrrolyl, thiazolyl, isothiazolyl, imidazolyl, pyrazolyl, oxazolyl and isoxazolyl. Useful bicyclic groups are benzo-fused ring systems derived from the heteroaryl groups named above, e.g., quinolyl, phthalazinyl, quinazolinyl, benzofuranyl, benzothienyl and indolyl.

The term "lower alkyl" should be understood to include straight chain and branched hydrocarbon groups having from 1 to 8, preferably 1 to 6, more preferably from 1 to 3 carbon atoms, which may be optionally substituted. Non-limiting examples of suitable lower alkyl groups include methyl, ethyl, n-propyl, isopropyl, n-butyl, t-butyl, n-pentyl, fluoromethyl and trifluoromethyl.

The term "branched" should be understood to represent a linear straight chain hydrocarbon group having one or more lower alkyl groups such as methyl, ethyl or propyl, attached to it.

The term "lower alkoxy" should be understood to include "lower alkyl-O-"-groups, wherein the lower alkyl groups are as described above and have from 1 to 8, preferably 1 to 6, more preferably from 1 to 3 carbon atoms. Methoxy, ethoxy and isopropoxy groups are especially preferred.

The term "aryl(lower alkyl)" should be understood to include an aryl(lower alkyl) group in which the aryl and lower alkyl are as previously described. Non-limiting examples of suitable aryl(lower alkyl) groups include benzyl, phenethyl and naphthalenylmethyl.

If not otherwise indicated, the term "optionally substituted" should be understood to represent substituents independently selected from the group consisting of aryl, heteroaryl, aryl(lower alkyl), (lower alkyl)aryl, aralkenyl, heteroaralkyl, alkylheteroaryl, heteroaralkenyl, hydroxy, hydroxyalkyl, alkoxy, aryloxy, aralkoxy, acyl, aroyl, halogen, nitro, cyano, carboxy, alkoxycarbonyl, aryloxycarbonyl, aralkoxycarbonyl, aminoalkyl, alkylthio, arylthio, heteroarylthio, aralkylthio, heteroaralkylthio, cycloalkyl, cycloalkenyl, heterocyclyl, heterocyclenyl, preferably lower alkyl, hydroxy, lower alkoxy, cyano, alkylthio, amino, —NH(lower alkyl), —N(lower alkyl)2 (which alkyls can be the same or different), carboxy, —C(O)O-(lower alkyl) and halogen. Those skilled in the art will recognize that the size and nature of the substituent(s) will affect the number of substituents which can be present.

The term "halogen" should be understood to include fluoro, chloro, bromo. iodo, preferably, fluoro and chloro, most preferably, fluoro.

It is understood that all isomers, including enantiomers, stereoisomers, rotamers, tautomers and racemates of the compounds of formula I and in particular the compounds of formulas II and III are contemplated as being part of this invention. The invention includes stereoisomers in optically pure form and in admixture, including racemic mixtures. Isomers can be prepared using conventional techniques, either by reacting optically pure or optically enriched starting materials or by separating isomers of a compound of formula I and in particular the compounds of formulas II and III. In a preferred embodiment the stereochemistry in the central ring is such that the substituents at the 3- and 4-position are in trans configuration to each other.

In yet a further embodiment, preferred combinations of groups $R_a$ and $R_b$ include combinations wherein $R_b$ is as defined hereinabove and is in para-position (in relation to the linker $Sp_2$) and $R_a$ is as defined hereinabove, most preferably H, and is in meta-position.

Thus in a further preferred embodiment the present invention is directed towards a compound of formula IVa,

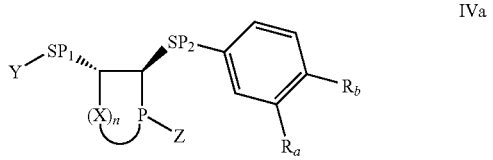

IVa wherein $R_a$, $R_b$, $Sp_1$, $Sp_2$, P, X, Y, Z and n are as defined hereinabove.

Such preferred combinations are thus compounds of formulas IIa-f and IIIa-h wherein $R_b$ is as defined hereinabove and is in para-position (in relation to the linker $Sp_2$) and $R_a$ is as defined hereinabove, most preferably H, and is in meta-position.

Further preferred embodiments include combinations, wherein $Sp_2$ is a covalent bond and Y and Z represent optionally substituted phenyl rings.

Thus in a further preferred embodiment the present invention is directed towards a compound of formula IVb,

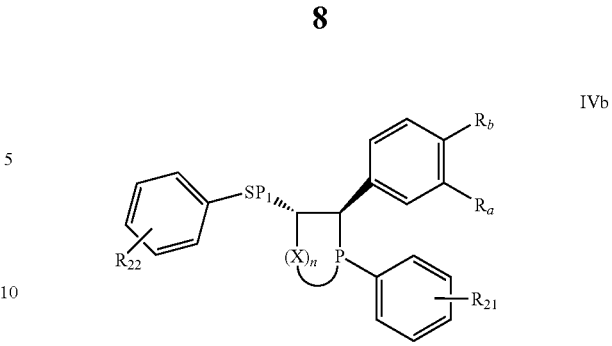

IVb wherein $R_a$, $R_b$, $Sp_1$, P and X are as defined hereinabove and wherein $R_{21}$ and $R_{22}$ preferably represent H, lower alkyl, lower alkoxy or halogen, most preferably in para-position.

Such combinations are thus compounds of formulas IIa-f and IIIa-h wherein $Sp_2$ is a covalent bond and Y and Z represent optionally substituted phenyl rings.

Compounds of formula I and in particular compounds of formulas II and III may be prepared using methods of preparation known in the art and are described in the following paragraphs:

The 2-azetidinone portions of the compounds of formula II can be prepared by known methods, such as are disclosed in U.S. Pat. Nos. 5,631,365, 5,756,470, 5,767,115, 5,846,966, 6,207,822, U.S. Provisional Patent Application No. 60/279, 288 filed Mar. 28, 2001, and PCT Patent Application WO 93/02048, each of which is incorporated herein by reference. Compounds of formula IIa according to the invention may then be obtained by further linkage to appropriate carbohydrate structures using literature procedures as illustrated by the Examples.

Compounds of formula IIb may be obtained through conversion of β-lactams to thiolactams, most commonly performed with Lawesson's reagent (Verkoyen, C. and Rademacher, P. *Chem. Ber.* 1985, 118, 653-660; Yde, B. et al. *Tetrahedron* 1984, 40, 2047-2052; Steliou, K.; Mrani, M. *J. Am. Chem. Soc.* 1982, 104, 3104-3106; Clader, J. W. et al. *J. Med. Chem.* 1996, 39, 3684-3693).

Compounds of formula IIc may be obtained through conversion of β-lactams to azetidines, which may be achieved by a number of well known methods in the art, such as (1) direct one-step reduction with reducing agents of the composition $AlH_xCl_{3-x}$, such as chlorodihydroalane or alane (Jackson, M. B. et al. *Aust. J. Chem.* 1983, 36, 779), or diborane (Jackson, M. B. et al.; *Aust. J. Chem.* 1983, 36, 779-788), $AlHCl_2$ and DIBAL-H (Yamashita, M. and Ojima, I. *J. Am. Chem. Soc.* 1983, 105, 6339-6342; Ojima, I. et al. *J. Org. Chem.* 1991, 56, 5263-5277); and (2) cyclodehydration of 1,3-amino alcohols using various methods (Sohar, P. et al. *Chem. Soc. Perkin Trans.* 2 2000, 287-293; Suga, H. et al. S. *J. Am. Chem. Soc.* 1994, 116, 11197-11198; Barluenga, J. et al. *Tetrahedron* 1996, 52, 3095-3106; Obika, S. et al. *Tetrahedron Lett.* 2003, 44, 5267-5270) as also outlined in the Examples.

The preparation of compounds of formula IIIa is effected as outlined in Scheme I through initial Sharpless asymmetric amino hydroxylation reaction of the desired trans-1,2-disubstituted alkenes (Demko, Z. P. et al. *Org. Lett.* 2000, 2, 2221-2223; O'Brien, P. *Angew. Chem. Int. Edit. Engl.* 1999, 38, 326-329; Bodkin, J. A.; McLeod, M. D. *J. Chem. Soc. Perkin Trans.* 1 2002, 2733-2746), followed by chromatographic separation to obtain the desired regioisomeric product. Subsequent cleavage of the paratoluene sulfonamide group furnishes a primary amine which upon Buchwald-Hartwig arylation reaction (Hartwig, J. F. *Acc. Chem. Res.* 1998, 31, 852-860; Wolfe, J. P.; Wagaw, S.; Marcoux, J. F.; Buchwald, S. L. *Acc. Chem. Res.* 1998, 31, 805-818) and subsequent exposure to triphosgene eventually leads to the formation of the desired oxazolidinones of formula IIIa. Alternatively, they can be accessed as outlined in the Examples.

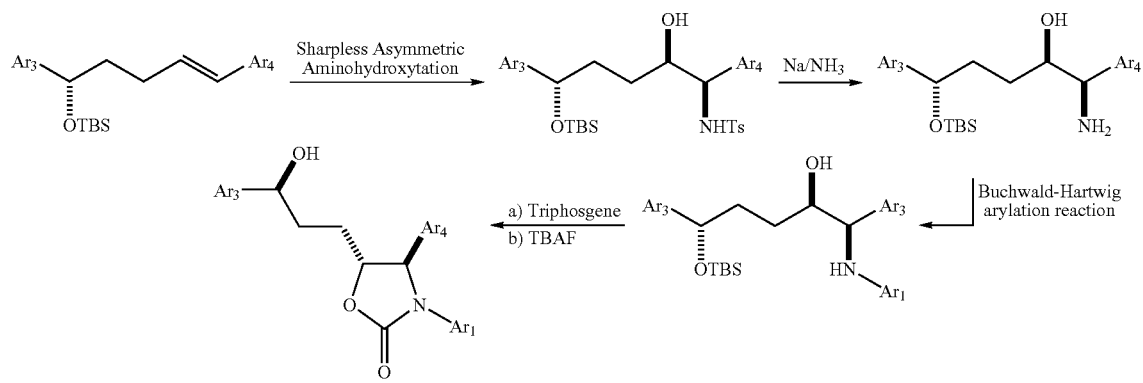

Compounds of formula IIIe may be obtained e.g. as illustrated in Scheme II using known methods in the art (Mish, M. R. et al. *J. Am. Chem. Soc.* 1997, 119, 8379-8380; Guerra, F. M. et al. *Org. Lett.* 2000, 2, 4265-4267). Alternatively, compounds in which $sp_2$ is not a covalent bond can be synthesized as demonstrated in the Examples.

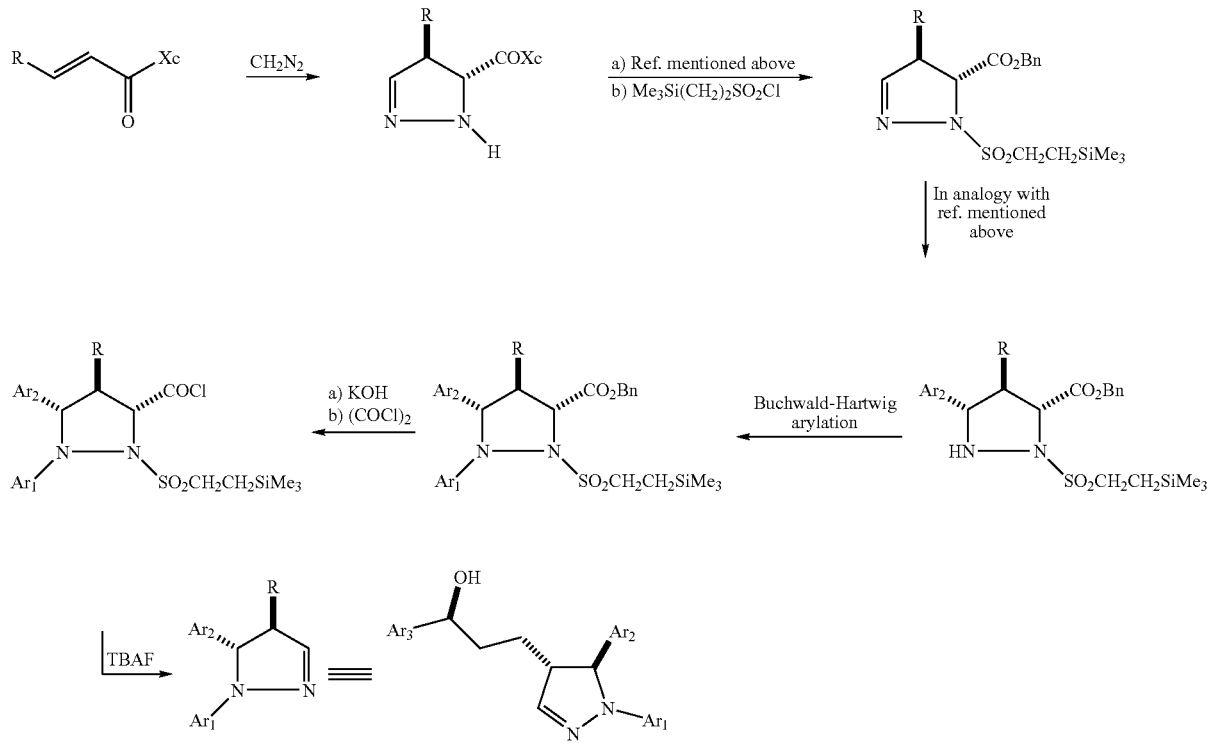

The preparation of pyrazolidinones of formula IIIc proceeds in an analogous strategy to that reported in the literature as illustrated in Scheme III (Lou, B. S. et al. *J. Org. Chem.* 1995, 60, 5509-5514; Tomkinson, N. C. O. *Rodd's Chemistry of Carbon Compounds* (2nd Edition), *Asymmetric Catalysis*, Ed. M. Sainsbury 2001, 5, 199-258).

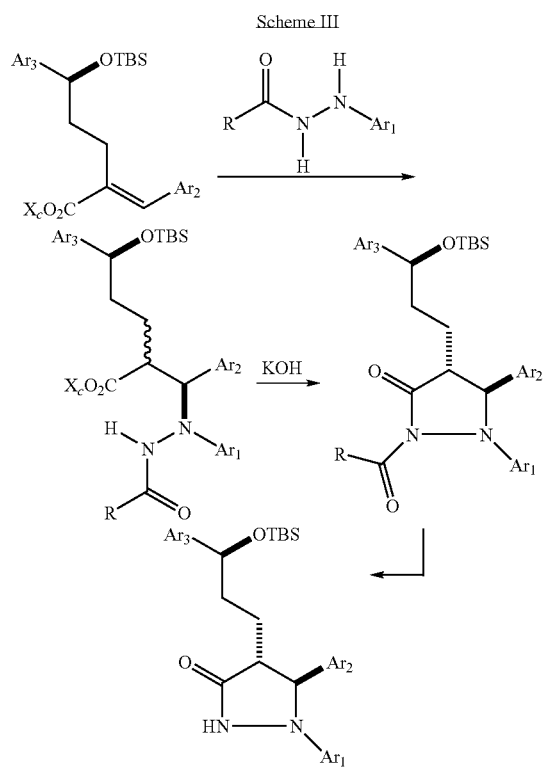

Scheme III

It has been found that the use of sulfonate linkages in e.g. the Rb or Sp3 group, i.e. linking carbohydrates to the phenylene ring is particularly beneficial in that the S=O double bonds in the linkages may function as hydrogen bond acceptors compared to the more non-polar nature of a C-glycoside linkage. Such linkages have not yet been reported to link carbohydrates to other kinds of molecules. Furthermore the linkages are nonhydrolyzable, i.e. the carbohydrates are not hydrolyzed off.

It has further been shown that the compounds of the invention display superior pharmacological activities and are able to overcome the drawbacks of known cholesterol-lowering agents using well-established methods in the art, e.g. evaluation of their $IC_{50}$ value for cholesterol uptake in rabbit brush border membrane vesicles (BBMV) as well as in Caco-2 cells (Hauser, H. et al, *Biochemistry* 1998, 37, 17843-17850; Schulthess, G. et al, *Biochemistry* 2000, 39, 12623-12631; Werder, M. et al, *Biochemistry* 2001, 40, 11643-11650; Boffelli, D. et al. *FEBS Lett.* 1997, 411, 7-11) (see also Table I).

Thus, the compounds of the invention, e.g. compounds of formula I and their pharmaceutically acceptable acid addition salts, exhibit pharmacological activity and are, therefore, useful as pharmaceuticals. The compounds of the invention have been shown to effectively inhibit cholesterol absorption and are therefore useful in the treatment and/or prevention of atherosclerosis and of the reduction of cholesterol levels.

Thus in yet a further aspect, the present invention is directed to a method of treatment and/or prevention of atherosclerosis, of the reduction of cholesterol levels and of treating or preventing a vascular condition, comprising administering to a mammal in need of such treatment an effective amount of a compound of formula I and in particular a compound of formulas II and III.

The novel compounds of formula I can be used, for example, in the form of pharmaceutical compositions containing a therapeutically effective amount of the active ingredient, if appropriate together with inorganic or organic, solid or liquid, pharmaceutically acceptable carriers suitable for enteral, e.g. oral, or parenteral administration. Accordingly, tablets or gelatin capsules are used that contain the active ingredient together with diluents, typically lactose, dextrose, saccharose, mannitol, sorbitol, cellulose and/or lubricants, e.g. diatomaceous earth, talcum, stearic acid or salts thereof, such as magnesium stearate or calcium stearate, and/or polyethylene glycol. Tablets may also contain binders, typically magnesium aluminium silicate, starches, typically corn starch, wheat starch, rice starch or arrow root starch, gelatin, tragacanth, methylcellulose, sodium carboxymethylcellulose and/or polyvinylpyrrolidone, and, if desired, disintegrators, typically starches, agar, alginic acid or a salt thereof, e.g. sodium alginate, and/or effervescent mixtures, or absorbents, colourants, flavourings and sweeteners.

Thus in another aspect, the invention relates to a pharmaceutical composition comprising a compound of formula I, and in particular a compound of formulas II and III (and optionally other therapeutically effective agents), and a pharmaceutically acceptable carrier for the treatment or prevention of arteriosclerosis or for the reduction of cholesterol levels.

The terms "effective amount" and "therapeutically effective amount" mean that amount of a compound of formula I and in particular compounds of formulas II and III (and optionally other therapeutically effective agents), that will elicit a biological or medical response of a tissue, system, animal or mammal, which includes alleviation of the symptoms of the condition or disease being treated and the prevention, slowing or halting of progression of one or more conditions, for example atherosclerosis, hypercholesterolemia.

The pharmaceutical compositions so obtained which, if desired, contain further pharmacologically active substances, are prepared in a manner known per se by conventional mixing, granulating, sugar-coating, solution or lyophilising methods and contain from about 0.1% to 100%, preferably from about 1% to about 50%, lyophilisate to about 100%, of active ingredient.

The compounds, compositions and treatments of the present invention can be administered by any suitable means which produce contact of these compounds with the site of action in the body, for example in the plasma, liver or small intestine of a mammal or human. Thus the novel compounds of formula I may also be used in the form of compositions for parenteral, oral, transdermal administration or infusion solutions. Such solutions are preferably isotonic aqueous solutions or suspension which, e.g. in the case of lyophilised compositions that contain the active ingredient by itself or together with a carrier, such as mannitol, can be prepared before use. The pharmaceutical compositions can be sterilised and/or can contain excipients, typically preservatives, stabilisers, wetting agents and/or emulsifiers, solubilisers, salts for regulating the osmotic pressure and/or buffers.

In yet a further aspect, the invention relates to a kit comprising an effective amount of a compound of formula I and in particular a compound of formulas II and III in a pharmaceutically acceptable carrier (and optionally an effective amount of another therapeutically effective agent), optionally in separate compartments.

The following non-limiting Examples illustrate the above-described invention in more detail.

EXAMPLES

Materials and Methods: Reactions in anhydrous solvents were all performed using oven dried glassware under an atmosphere of argon. Reagent grade solvents were all purchased from chemical companies and used without prior purification. For chromatic purification, technical grade solvents were distillated prior to use. TLC was performed using Machery-Nagel Alugram Sil G/UV$_{254}$ TLC plates and visualized with ultraviolet light at 254 nm and 12 g phosphor molybdic acid in 250 mL EtOH or 10% H$_2$SO$_4$ in MeOH (v/v). Chromatographic purification of products was accomplished using dry column vacuum chromatography on Merck Silica Gel 60 (15-40 μm) according to literature procedures (Pedersen, D. S. and Rosenbohm, C. *Synthesis* 2001, 2431-2434); fractions containing product were pooled, the solvents were evaporated under reduced pressure and the residue was dried under high vacuum to give the product. NMR spectra were recorded on a Varian Mercury 300 MHz apparatus operating at 300 MHz and 75 MHz for $^1$H and $^{13}$C, respectively, and chemical shifts (δ) were referenced to the internal solvent signals. IR-Spectra were recorded in CHCl$_3$ on a Perkin Elmer Spectrum RX I FT-IR apparatus (thin films on NaCl plates) and are reported as absorption maxima in cm$^{-1}$. Elemental analysis was performed by the Mikroelementaranalytisches Laboratorium at the ETH, Zürich. High resolution matrix-assisted laser desorption ionization mass spectrometry (MALDI-MS) was recorded in positive ion mode.

Example 1

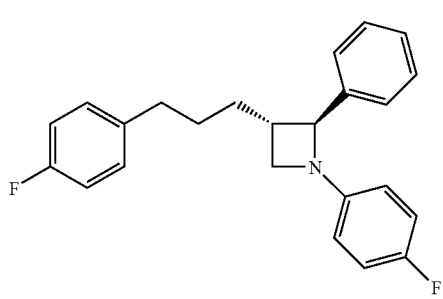

V

LiAlH$_4$ (114 mg, 3.0 mmol) and AlCl$_3$ (390 mg, 2.9 mmol) were suspended in anhydrous ether (15 mL) and refluxed for 30 min. Trans-1-(4-fluorophenyl)-3-[(3-phenyl)-propyl]-4-phenyl-2-azetidinone (361 mg, 1.00 mmol; prepared according to Browne, M. et al. Tetrahedron Lett. 1995, 36, 2555-2558) dissolved in anhydrous ether (15 mL) was added and after stirring at reflux for 30 min, the suspension was cooled and H$_2$O (5 mL) was added dropwise followed by addition of 50% sat. aq. NaHCO$_3$ (30 mL). The layers were separated, the aqueous layer was extracted with EtOAc/hexane and ether and the combined organic layer was washed successively with sat. aq. NaHCO$_3$ (20 mL) and H$_2$O (20 mL), evaporated on celite and purified by dry column vacuum chromatography (3.7×3.3 cm) on silica gel eluting with a gradient of 0-10% EtOAc in hexane (v/v) to give the desired compound V (281 mg, 81%) as a colourless oil.

$^1$H-NMR (300 MHz, CDCl$_3$) δ: 7.51-7.14 (10H, m), 6.87 (2H, t, J=8.7 Hz), 6.38 (2H, dd, J=4.7, 9.0 Hz), 4.46 (1H, d, J=6.8 Hz), 4.17 (1H, t, J=6.8 Hz), 3.35 (1H, dd, J=6.8, 7.5 Hz), 2.69-2.58 (3H, m), 1.85-1.56 (4H, m). $^{13}$C-NMR (75 MHz, CDCl$_3$) δ: 157.64, 154.52, 148.53, 142.69, 141.95 (C), 128.66, 128.25, 127.47, 125.99, 125.73, 115.41, 115.12, 113.04, 112.94 (CH), 74.37 (CH), 56.05 (CH$_2$), 42.09 (CH), 35.85, 33.52, 28.92 (CH$_2$). IR (cm$^{-1}$): 3026, 2933, 2852, 1603, 1508, 1473, 1453, 1321, 1222, 1120, 823, 773, 747, 699. MALDI-MS (C$_{24}$H$_{24}$FN): [MH]$^+$ 346.1982 (calcd. 346.1971). Anal. Calcd for C$_{24}$H$_{24}$FN: C, 83.44; H, 7.00; N, 4.05. Found: C, 83.45; H, 7.06; N, 4.27.

Example 2

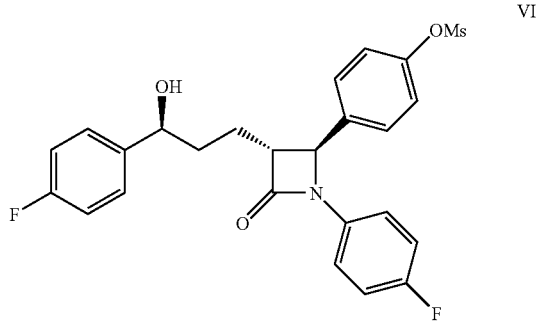

VI a)

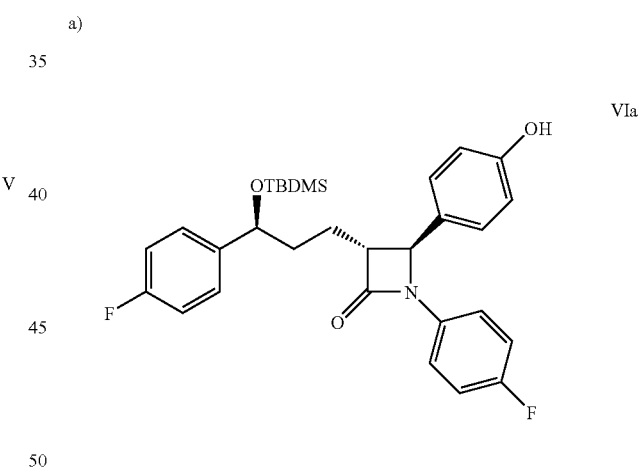

VIa

Ezetimibe (commercially obtained or synthesized according to Wu, G. Z. et al., *J. Org. Chem.* 1999, 64, 3714-3718) (5.530 g, 13.5 mmol) was suspended in 2-propanol (70 mL), aq. NaOH (2M, 15 mL) followed by AC$_2$O (3.0 mL, 32 mmol) were added and the solution was stirred for 5 h followed by addition of sat. aq. NaHCO$_3$ (200 mL). After extraction with EtOAc (4×50 mL), the combined organic layer was washed successively with sat. aq. NaHCO$_3$ (50 mL) and H$_2$O (50 mL), evaporated on celite and purified by dry column vacuum chromatography (5.2×5.5 cm) on silica gel eluting with a gradient of 0-100% EtOAc in hexane (v/v) to give the corresponding azetidinone acetate (5.930 g, 97%) as a white foam.

$^1$H-NMR (300 MHz, CDCl$_3$) δ: 7.31 (2H, d, J=8.7 Hz), 7.29-7.18 (4H, m), 7.09 (2H, d, J=8.7 Hz), 6.99 (2H, t, J=8.7 Hz), 6.92 (2H, t, J=8.7 Hz), 4.67 (1H, bs), 4.61 (1H, d, J=2.5

Hz), 3.08-3.04 (1H, m), 2.75 (1H, bs), 2.29 (3H, s), 1.97-1.85 (4H, m). $^{13}$C-NMR (75 MHz, CDCl$_3$) δ: 169.16, 167.23, 163.56, 160.46, 160.32, 157.24, 150.58, 139.94, 139.90, 134.85, 133.53, 133.50 (C), 127.32, 127.21, 126.78, 122.38, 118.34, 118.23, 115.95, 115.65, 115.35, 115.07 (CH), 72.95, 60.81, 60.33 (CH), 36.61, 25.07 (CH$_2$), 21.19 (CH$_3$). IR (cm$^{-1}$): 3443, 3019, 2936, 2862, 1747, 1605, 1509, 1427, 1388, 1370, 1221, 1198, 1157, 1016, 835, 757, 668. MALDI-MS (C$_{26}$H$_{23}$F$_2$NO$_4$): [MH-H$_2$O]$^+$ 434.1556 (calcd. 434.1568); [MNa]$^+$ 474.1485 (calcd. 474.1493))

Subsequently the acetate (1.864 g, 4.13 mmol) was dissolved in anhydrous DMF (25 mL), imidazole (939 mg, 13.8 mmol) and TBDMSCl (1.853 g, 12.3 mmol) were added sequentially and the solution was stirred for 3 h followed by addition of 50% sat. aq. NaHCO$_3$ (150 mL). After extraction with EtOAc (4×40 mL), the combined organic layer was washed successively with sat. aq. NaHCO$_3$ (40 mL) and H$_2$O (40 mL), evaporated on celite and purified by dry column vacuum chromatography (4.2×5.5 cm) on silica gel eluting with a gradient of 0-30% EtOAc in hexane (v/v) to give the corresponding silylated azetidinone acetate (2.137 g, 91%) as a colourless oil.

$^1$H-NMR (300 MHz, CDCl$_3$) δ: 7.31 (2H, d, J=8.7 Hz), 7.26-7.20 (4H, m), 7.10 (2H, d, J=8.7 Hz), 6.98 (2H, t, J=8.7 Hz), 6.91 (2H, t, J=8.7 Hz), 4.67 (1H, t, J=5.3 Hz), 4.58 (1H, d, J=1.9 Hz), 3.06-3.02 (1H, m), 2.28 (3H, s), 1.96-1.80 (4H, m), 0.88 (9H, s), 0.02 (3H, s), −0.16 (3H, s). $^{13}$C-NMR (75 MHz, CDCl$_3$) δ: 169.16, 167.06, 163.42, 160.47, 160.16, 157.23, 150.62, 140.50, 135.10, 133.74, 133.70 (C), 127.26, 127.14, 126.77, 122.37, 118.27, 118.16, 115.89, 115.58, 115.03, 114.76 (CH), 73.74, 60.67, 60.53 (CH), 37.94 (CH$_2$), 25.73 (CH$_3$), 24.55 (CH$_2$), 20.99 (CH$_3$), 18.07 (C), −4.74, −5.05 (CH$_3$). IR (cm$^{-1}$): 2953, 2930, 2857, 1752, 1606, 1510, 1472, 1426, 1385, 1370, 1252, 1219, 1197, 1166, 1140, 1102, 1086, 1015, 912, 835, 777, 736. MALDI-MS: [MH-TBDMSOH]$^+$ 434.1556 (calcd. 434.1568); [MNa]$^+$ 588.2347 (calcd. 588.2358). Anal. Calcd for C$_{32}$H$_{37}$F$_2$NO$_4$Si: C, 67.94; H, 6.59; N, 2.48. Found: C, 67.94; H, 6.64; N, 2.37)

The silylated azetidinone acetate (5.123 g, 9.06 mmol) was dissolved in CH$_2$Cl$_2$ (200 mL), neutral alumina (50 g) was added and the suspension was evaporated to dryness. The coated alumina was dried shortly under vacuum and then heated to 70° C. for 5.5 h. After cooling, the alumina was extracted with 10% MeOH in CH$_2$Cl$_2$ (8×50 mL) and the combined organic extracts were evaporated on celite and purified by dry column vacuum chromatography (5.4×5.5 cm) on silica gel eluting with a gradient of 0-30% EtOAc in hexane (v/v) to give the silylated azetidinone phenol VIa (3.919 g, 83%) as a white foam.

$^1$H-NMR (300 MHz, CDCl$_3$) δ: 7.26-7.14 (6H, m), 6.99-6.83 (6H, m), 6.16 (1H, bs), 4.65 (1H, t, J=5.3 Hz), 4.52 (1H, d, J=1.9 Hz), 3.04-2.98 (1H, m), 1.92-1.76 (4H, m), 0.86 (9H, s), 0.00 (3H, s), −0.17 (3H, s). $^{13}$C-NMR (75 MHz, CDCl$_3$) δ: 167.82, 163.28, 160.42, 156.12, 140.50, 140.45, 133.57 (C), 128.92, 127.19, 127.15, 127.08, 118.43, 118.32, 116.05, 115.85, 115.55, 115.01, 114.72 (CH), 73.82, 61.17, 60.35 (CH), 38.07 (CH$_2$), 25.89 (CH$_3$), 24.68 (CH$_2$), 18.25 (C), −4.54, −4.84 (CH$_3$). IR (cm$^{-1}$): 3351, 2953, 2938, 2857, 1722, 1615, 1604, 1510, 1450, 1391, 1361, 1252, 1223, 1156, 1103, 1087, 863, 834, 776, 760. MALDI-MS: [MH-TBDMSOH]$^+$ 392.1451 (calcd. 392.1462); [MH]$^+$ 524.2409 (calcd. 524.2433); [MNa]$^+$ 546.2242 (calcd. 546.2252). Anal. Calcd for C$_{30}$H$_{35}$F$_2$NO$_3$Si: C, 68.81; H, 6.74; N, 2.67. Found: C, 68.61; H, 6.82; N, 2.66.

b)

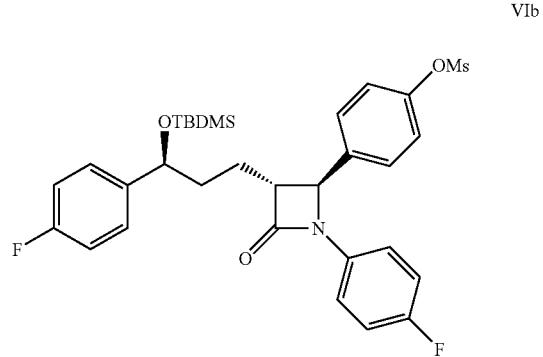

The silylated azetidinone phenol VIa (176 mg, 0.336 mmol) was dissolved in anhydrous CH$_2$Cl$_2$ (10 mL), anhydrous pyridine (0.5 mL) followed by MsCl (0.1 mL, 1.29 mmol) were added and the solution was stirred for 22 h, diluted with EtOAc (50 mL) and washed sequentially with sat. aq. NaHCO$_3$ (20 mL) and H$_2$O (20 mL). The organic layer was evaporated on celite and purified by dry column vacuum chromatography (4.2×3.3 cm) on silica gel eluting with a gradient of 0-50% EtOAc in hexane (v/v) to give the intermediate mesylate VIb (195.5 mg, 92%) as a colourless oil.

$^1$H-NMR (300 MHz, CDCl$_3$) δ: 7.35 (2H, d, J=8.7 Hz), 7.28 (2H, d, J=8.7 Hz), 7.26-7.18 (4H, m), 6.98 (2H, t, J=8.7 Hz), 6.93 (2H, t, J=8.7 Hz), 4.67 (1H, dd, J=4.4, 6.2 Hz), 4.59 (1H, d, J=1.9 Hz), 3.16 (3H, s), 3.04-3.00 (1H, m), 1.93-1.79 (4H, m), 0.87 (9H, s), 0.01 (3H, s), −0.16 (3H, s). $^{13}$C-NMR (75 MHz, CDCl$_3$) δ: 166.83, 163.46, 160.57, 160.21, 157.34, 148.88, 140.53, 140.49, 137.07, 133.59, 133.56 (C), 127.36, 127.28, 127.18, 122.94, 118.26, 118.16, 116.04, 115.73, 115.10, 114.81 (CH), 73.79, 60.67, 60.41 (CH), 37.97 (CH$_2$), 37.59, 25.76 (CH$_3$), 24.60 (CH$_2$), 18.11 (C), −4.71, −5.02 (CH$_3$). IR (cm$^{-1}$): 2952, 2931, 2857, 1752, 1605, 1509, 1371, 1252, 1220, 1176, 1153, 1102, 1086, 971, 871, 835, 777. MALDI-MS: [MH-TBDMSOH]$^+$ 470.1228 (calcd. 470.12376); [MNa]$^+$ 624.2029 (calcd. 624.2027). Anal. Calcd for C$_{31}$H$_{37}$F$_2$NO$_5$SiS: C, 61.87; H, 6.20; N, 2.33. Found: C, 61.69; H, 6.19; N, 2.15).

c)

The intermediate mesylate received in the previous step (67.7 mg, 0.112 mmol) was dissolved in THF (2 mL), TBAF (0.2 mL, 1M in THF) was added and the solution was stirred for 1.5 h, diluted with EtOAc (20 mL) and washed successively with sat. aq. NaHCO$_3$ (10 mL) and H$_2$O (10 mL). The organic layer was evaporated on celite and purified by dry column vacuum chromatography (4.2×2.0 cm) on silica gel eluting with a gradient of 0-90% EtOAc in hexane (v/v) to give the desired mesylated azetidinone VI (37.0 mg, 68%) as a white solid after coevaporation with hexane (10

$^1$H-NMR (300 MHz, CDCl$_3$) δ: 7.37-7.17 (8H, m), 7.03-6.91 (4H, m), 4.69 (1H, t, J=5.9 Hz), 4.65 (1H, d, J=1.9 Hz), 3.16 (3H, s), 3.07-3.01 (1H, m), 2.63 (1H, bs), 2.03-1.84 (4H, m). $^{13}$C-NMR (75 MHz, CDCl$_3$) δ: 167.11, 163.76, 160.68, 160.50, 157.44, 148.89, 139.92, 136.86, 133.41 (C), 127.40, 127.27, 122.98, 118.35, 118.24, 116.10, 115.79, 115.45, 115.18, 115.11 (CH), 73.03, 60.48, 60.41 (CH), 37.63 (CH$_3$), 36.48, 25.00 (CH$_2$). IR (cm$^{-1}$): 3428, 2937, 1744, 1604, 1510, 1426, 1369, 1221, 1176, 1152, 1103, 1016, 971, 912, 872, 835, 788, 734. MALDI-MS: [MH-H$_2$O]$^+$ 470.1239

(calcd. 470.1238); [MNa]+ 510.1164 (calcd. 510.1163). Anal. Calcd for $C_{25}H_{23}F_2NO_5S$: C, 61.59; H, 4.75; N, 2.87. Found: C, 61.79; H, 4.89; N, 2.76.

Example 3

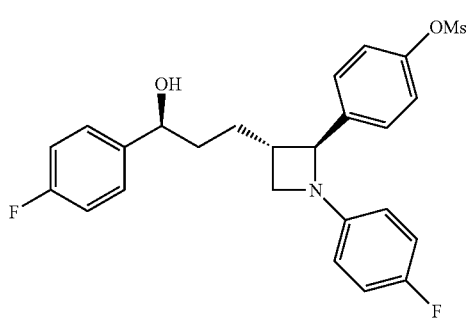

VII

LiAlH$_4$ (58 mg, 1.5 mmol) and AlCl$_3$ (202 mg, 1.5 mmol) were suspended in anhydrous ether (15 mL), refluxed for 30 min and cooled to 0° C. The mesylate VIb obtained in step 2b) (195.5 mg, 0.325 mmol) dissolved in anhydrous ether (5 mL) was added and after stirring at 0° C. for 15 min, sat. aq. NaHCO$_3$ (1 mL) was added dropwise. The suspension was evaporated on celite and purified by dry column vacuum chromatography (4.6×3.3 cm) on silica gel eluting with a gradient of 0-50% EtOAc in hexane (v/v) to give the intermediate silylated azetidine (146.4 mg, 77%) as a colourless oil.

$^1$H-NMR (300 MHz, CDCl$_3$) δ: 7.49 (2H, d, J=8.7 Hz), 7.30 (2H, d, J=8.7 Hz), 7.18 (2H, dd, J=5.0, 8.7 Hz), 6.98 (2H, t, J=8.7 Hz), 6.85 (2H, t, J=8.7 Hz), 6.31 (2H, dd, J=4.4, 9.3 Hz), 4.58 (1H, t, J=5.3 Hz), 4.40 (1H, d, J=6.8 Hz), 4.11 (1H, t, J=7.2 Hz), 3.28 (1H, t, J=7.2 Hz), 3.17 (3H, s), 2.56-2.49 (1H, m), 1.77-1.50 (4H, m), 0.88 (9H, s), 0.01 (3H, s), −0.15 (3H, s). $^{13}$C-NMR (75 MHz, CDCl$_3$) δ: 163.22, 159.99, 157.69, 154.57, 148.23, 148.07, 141.97, 140.62 (C), 127.41, 127.13, 127.03, 122.25, 115.43, 115.13, 114.96, 114.68, 113.00, 112.90 (CH), 73.86, 73.29 (CH), 55.88 (CH$_2$), 41.88 (CH), 37.90 (CH$_2$), 37.43 (CH$_3$), 29.43 (CH$_2$), 25.85 (CH$_3$), 18.24 (C), −4.53, −4.88 (CH$_3$). IR (cm$^{-1}$): 2932, 2856, 1605, 1509, 1473, 1372, 1331, 1252, 1222, 1198, 1171, 1151, 1090, 970, 870, 836, 776. MALDI-MS: [MH-TBDMSOH]+ 456.1442 (calcd. 456.14449); [MNa]+ 610.2236 (calcd. 610.22348). Anal. Calcd for $C_{31}H_{39}F_2NO_4SiS$: C, 63.34; H, 6.69; N, 2.38. Found: C, 63.49; H, 6.87; N, 2.33.

This intermediate silylated azetidine (146.3 mg, 0.249 mmol) was dissolved in anhydrous THF (5.0 mL, teflon bottle) at 0° C., anhydrous pyridine (1.0 mL) followed by HF-pyridine complex (1.0 mL) were added and the solution was stirred at 0° C. for 1 h and at room temperature for 7 h, diluted with ether (30 mL) and washed with sat. aq. NaHCO$_3$ (3×10 mL). The organic layer was evaporated on celite and purified by dry column vacuum chromatography (4.2×2.0 cm) on silica gel eluting with a gradient of 0-90% EtOAc in hexane (v/v) to give the desired mesylated azetidine VII (100.0 mg, 85%) as a white foam.

$^1$H-NMR (300 MHz, CDCl$_3$) δ: 7.50 (2H, d, J=8.7 Hz), 7.28 (2H, d, J=8.7 Hz), 7.22 (2H, dd, J=5.6, 8.7 Hz), 7.01 (2H, t, J=8.7 Hz), 6.84 (2H, t, J=8.7 Hz), 6.30 (2H, dd, J=4.3, 9.3 Hz), 4.57 (1H, t, J=5.6 Hz), 4.41 (1H, d, J=6.8 Hz), 4.12 (1H, t, J=6.8 Hz), 3.30 (1H, dd, J=6.8, 7.5 Hz), 3.16 (3H, s), 2.55 (1H, dt, J=6.8, 7.5 Hz), 1.93 (1H, bs), 1.88-1.53 (4H, m).

$^{13}$C-NMR (75 MHz, CDCl$_3$) δ: 163.62, 160.37, 157.74, 154.61, 148.22, 148.01, 141.89, 139.95, 139.91 (C), 127.46, 127.28, 127.17, 122.29, 115.46, 115.42, 115.13, 113.02, 112.92 (CH), 73.43, 73.28 (CH), 55.92 (CH$_2$), 41.81 (CH), 37.49 (CH$_3$), 36.28, 29.85 (CH$_2$). IR (cm$^{-1}$): 3416, 2938, 2853, 1508, 1367, 1221, 1196, 1171, 1149, 970, 871, 823. MALDI-MS ($C_{25}H_{25}F_2NO_4S$): [MH-H$_2$O]+ 456.1447 (calcd. 456.1445); [M]+ 473.1481 (calcd. 473.1472); [MNa]+ 496.1380 (calcd. 496.1370).

Example 4

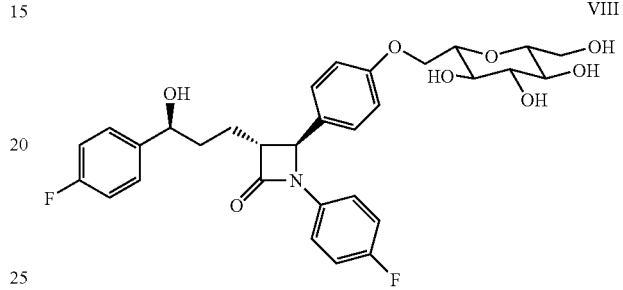

VIII

The silylated azetidinone phenol VIa obtained in step 2a) (143 mg, 0.273 mmol) and C-(hydroxymethyl)-2,3,4,6-tetra-O-benzyl-β-D-glucopyranoside (prepared according to RajanBabu, T. V. and Reddy, G. S. *J. Org. Chem.* 1986, 51, 5458-5461; 180 mg, 0.325 mmol) were dissolved in anhydrous THF (10 mL) at 0° C., Bu$_3$P (0.20 mL, 0.80 mmol) and 1,1'-(azodicarbonyl)dipiperidine (206 mg, 0.82 mmol) were added sequentially and the suspension was allowed to warm to ambient temperature over several hours and stirred for 24 h. EtOAc/hexane (1:4 (v/v), 20 mL) was added, the suspension was filtered through celite (2×10 mL EtOAc/hexane (1:4 (v/v)) washings) and the filtrate was evaporated on celite and purified by dry column vacuum chromatography (4.1×3.3 cm) on silica gel eluting with a gradient of 0-50% EtOAc in hexane (v/v) to give the corresponding C-glycoside (60.1 mg, 21%) as a colourless oil.

$^1$H-NMR (300 MHz, CDCl$_3$) δ: 7.37-7.17 (26H, m), 7.04-6.89 (6H, m), 4.96 (2H, bs), 4.89 (1H, d, J=9.3 Hz), 4.86 (1H, d, J=8.7 Hz), 4.69 (1H, t, J=5.3 Hz), 4.63-4.53 (5H, m), 4.21 (1H, d, J=10.6 Hz), 4.10 (1H, dd, J=5.0, 10.6 Hz), 3.85-3.52 (7H, m), 3.07-3.02 (1H, m), 2.01-1.78 (4H, m), 0.91 (9H, s), 0.05 (3H, s), −0.13 (3H, s). $^{13}$C-NMR (75 MHz, CDCl$_3$) δ: 167.25, 158.74, 140.53, 140.49, 138.29, 137.85, 137.79, 137.65, 133.81 (C), 129.53, 128.32, 128.28, 128.18, 127.96, 127.81, 127.78, 127.74, 127.66, 127.54, 127.48, 127.18, 127.08, 126.90, 118.22, 118.12, 115.77, 115.47, 115.30, 114.98, 114.70 (CH), 87.12, 79.14, 78.25, 77.87, 77.71 (CH), 75.56, 75.11, 75.03 (CH$_2$), 73.82 (CH), 73.44, 68.93, 67.23 (CH$_2$), 61.02, 60.47 (CH), 38.10 (CH$_2$), 25.89 (CH$_3$), 24.71 (CH$_2$), 18.24 (C), −4.54, −4.83 (CH$_3$). IR (cm$^{-1}$): 2951, 2929, 2858, 1749, 1608, 1510, 1454, 1386, 1361, 1250, 1223, 1156, 1141, 1101, 1028, 911, 835, 777, 735, 699. MALDI-MS ($C_{65}H_{71}F_2NO_8Si$): [MNa]+ 1082.4831 (calcd. 1082.4815).

This C-Glycoside (72 mg, 0.068 mmol) was subsequently dissolved in EtOH (5 mL), Pd(OH)$_2$/C (20% (w/w), 40 mg) was added and the suspension was evacuated 4 times with H$_2$ and stirred under an H$_2$-atmosphere for 17 h. The suspension was evaporated on celite and purified by dry column vacuum chromatography (3.8×2.0 cm) on silica gel eluting with a gradient of 0-100% EtOAc in hexane followed by 10%

MeOH in CH$_2$Cl$_2$ (v/v) to give the debenzylated C-glycoside (28 mg, 59%) as colourless oil.

$^{13}$C-NMR (75 MHz, CDCl$_3$) δ: 167.22, 163.28, 160.05, 158.36, 157.03, 140.57, 133.75, 130.30, 129.52, 127.22, 127.11, 118.23, 115.83, 115.54, 116.35, 115.05, 114.91, 114.76, 79.16, 78.33, 77.70, 73.88, 70.18, 69.52, 67.75, 61.54, 60.79, 60.57, 38.14, 25.91, 24.81, 18.27, −4.51, −4.80. IR (cm$^{-1}$): 3391, 2930, 2858, 1747, 1609, 1510, 1387, 1362, 1223, 1140, 1086, 1043, 1014, 835, 758. MALDI-MS (C$_{37}$H$_{47}$F$_2$NO$_8$Si): [MH-TBDMSOH]$^+$ 568.2132 (calcd. 568.2147); [MNa]$^+$ 722.2939 (calcd. 722.2937).

Subsequently, the debenzylated C-Glycoside (27.0 mg, 0.039 mmol) was dissolved in THF (1.0 mL), TBAF (0.2 mL, 1M in THF) was added and the solution was stirred for 15 h, diluted with CH$_2$Cl$_2$, evaporated on celite and purified by dry column vacuum chromatography (3.5×2.0 cm) on silica gel eluting with a gradient of 0-18% MeOH in CH$_2$Cl$_2$ (v/v) to give the desired C-glycoside VIII (14.0 mg, 62%) as a white solid after coevaporation with hexane (10 mL).

$^1$H-NMR (300 MHz, CD$_3$OD) δ: 7.33-7.23 (6H, m), 7.05-6.94 (6H, m), 4.78 (1H, d, J=1.9 Hz), 4.59 (1H, t, J=5.3 Hz), 4.29 (1H, dd, J=1.5, 10.3 Hz), 4.13 (1H, dd, J=5.6, 10.6 Hz), 3.85 (1H, d, J=11.2 Hz), 3.67-3.61 (1H, m), 3.57-3.51 (1H, m), 3.44-3.37 (2H, m), 3.31-3.28 (2H, m), 3.11-3.06 (1H, m), 1.97-1.81 (4H, m). $^{13}$C-NMR (75 MHz, CD$_3$OD) δ: 169.20, 160.12, 130.69, 128.36, 128.25, 128.14, 119.52, 119.41, 116.35, 116.04, 115.93, 115.63, 115.35, 81.55, 79.49, 79.39, 73.35, 71.30, 71.23, 68.77, 62.66, 61.74, 60.86, 37.22, 25.84. MALDI-MS (C$_{31}$H$_{33}$F$_2$NO$_8$): [MH-TBDMSOH]$^+$ 568.2143 (calcd. 568.2147); [MNa]$^+$ 608.2073 (calcd. 608.2072).

Example 5

IX

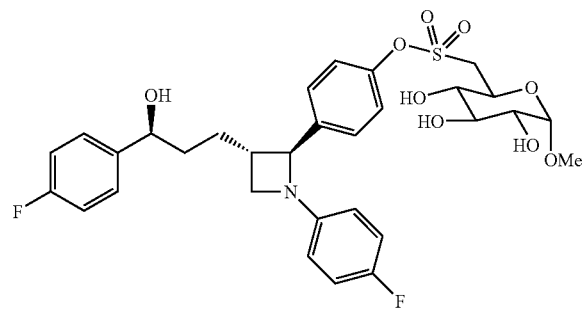

a)

IXa

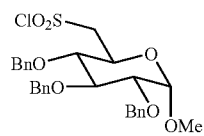

Methyl 2,3,4-Tri-O-benzyl-α-D-glucopyranoside (prepared according to Jaramillo, C. et al; Chiara, J. L.; Martin-lomas, M. J. Org. Chem. 1994, 59, 3135-3141; 1.181 g, 2.54 mmol) was dissolved in anhydrous CH$_2$Cl$_2$ (25 mL) at 0° C., anhydrous pyridine (3.0 mL) followed by MsCl (0.50 mL, 6.4 mmol) were added and the solution was stirred at 0° C. for 1 h and at room temperature for 7 h followed by addition of sat. aq. NaHCO$_3$ (50 mL). The layers were separated and the aqueous layer extracted with EtOAc (3×25 mL). The combined organic layer was washed successively with sat. aq. NaHCO$_3$ (25 mL) and H$_2$O (25 mL), evaporated on celite and purified by dry column vacuum chromatography (4.1×3.3 cm) on silica gel eluting with a gradient of 0-100% CH$_2$Cl$_2$ in hexane (v/v) followed by 0.25-1.0% MeOH in CH$_2$Cl$_2$ (v/v) to give the corresponding mesylate (1.303 g, 94%) as a colourless oil after coevaporation with acetonitrile (3×10 mL).

$^1$H-NMR (300 MHz, CDCl$_3$) δ: 7.39-7.26 (15H, m), 5.02 (1H, d, J=10.6 Hz), 4.92 (1H, d, J=10.6 Hz), 4.84 (1H, d, J=10.6 Hz), 4.80 (1H, d, J=12.5 Hz), 4.66 (1H, d, J=11.8 Hz), 4.63 (1H, d, J=10.6 Hz), 4.60 (1H, d, J=3.7 Hz), 4.41-4.32 (2H, m), 4.02 (1H, t, J=9.3 Hz), 3.85 (1H, dt, J=3.7, 10.0 Hz), 3.52 (1H, dt, J=3.7, 6.2 Hz), 3.50 (1H, bs), 3.39 (3H, s), 2.98 (3H, s). $^{13}$C-NMR (75 MHz, CDCl$_3$) δ: 138.30, 137.75, 137.56 (C), 128.36, 128.30, 127.94, 127.84, 127.76, 127.57 (CH), 98.06, 81.73, 79.69, 76.86 (CH), 75.73, 75.09, 73.44 (CH$_2$), 68.59 (CH), 68.36 (CH$_2$), 55.46, 37.54 (CH$_3$). IR (cm$^{-1}$): 3031, 2913, 1497, 1454, 1359, 1177, 1089, 1074, 1046, 1003, 965, 931, 813, 739, 699. MALDI-MS: [MNa]$^+$ 565.1873 (calcd. 565.1872). Anal. Calcd for C$_{29}$H$_{34}$O$_8$S: C, 64.19; H, 6.32. Found: C, 63.99; H, 6.27.

Subsequently, this mesylate (1.290 g, 2.38 mmol) was dissolved in EtOH (25 mL), KOSCMe (869 mg, 7.61 mmol) was added and the unclear solution was stirred at reflux for 4 h (orange precipitate). After cooling, 50% sat. aq. NaHCO$_3$ (100 mL) was added and the suspension was extracted with EtOAc (3×50 mL). The combined organic layer was washed successively with sat. aq. NaHCO$_3$ (50 mL) and H$_2$O (50 mL), evaporated on celite and purified by dry column vacuum chromatography (4.1×3.3 cm) on silica gel eluting with a gradient of 0-30% EtOAc in hexane (v/v) to give the corresponding thioacetate (1.189 g, 96%) as a light orange solid.

$^1$H-NMR (300 MHz, CDCl$_3$) δ: 7.41-7.32 (15H, m), 5.03 (1H, d, J=10.6 Hz), 4.94 (1H, d, J=10.6 Hz), 4.86 (1H, d, J=10.6 Hz), 4.82 (1H, d, J=11.8 Hz), 4.69 (1H, d, J=11.8 Hz), 4.66 (1H, d, J=10.6 Hz), 4.58 (1H, d, J=3.1 Hz), 4.02 (1H, t, J=9.0 Hz), 3.81 (1H, dt, J=2.5, 7.5 Hz), 3.55 (1H, dd, J=3.7, 9.3 Hz), 3.48 (1H, dd, J=3.1, 13.7 Hz), 3.40 (3H, s), 3.35 (1H, t, J=9.5 Hz), 3.08 (1H, dd, J=7.5, 13.7 Hz), 2.36 (3H, s). $^{13}$C-NMR (75 MHz, CDCl$_3$) δ: 194.67, 138.46, 137.90, 137.78 (C), 128.33, 128.29, 128.03, 127.94, 127.85, 127.81, 127.74, 127.53 (CH), 97.72, 81.69, 80.36, 79.78 (CH), 75.64, 75.04, 73.22 (CH$_2$), 69.23 (CH), 55.02 (CH$_3$), 30.73 (CH$_2$), 30.39 (CH$_3$). IR (cm$^{-1}$): 3063, 3031, 2908, 1694, 1497, 1454, 1358, 1201, 1156, 1136, 1092, 1072, 1050, 1029, 999, 955, 737, 698, 630. MALDI-MS: [MNa]$^+$ 545.1974 (calcd. 545.1974). Anal. Calcd for C$_{30}$H$_{34}$O$_6$S: C, 68.94; H, 6.56. Found: C, 68.77; H, 6.63.

The thioacetate received above (1.180 g, 2.26 mmol) was then dissolved in AcOH (25 mL), KOAc (4.082 g, 41.6 mmol) followed by Oxone (2KHSO$_5$.KHSO$_4$.K$_2$SO$_4$, 4.019 g, 8.69 mmol) were added and after stirring for 15 h, sat. aq. NaHCO$_3$ (100 mL), H$_2$O (50 mL) and sat. aq. Na$_2$CO$_3$ (50 mL) were carefully added. After extraction with EtOAc (4×40 mL), the combined organic layer was washed with sat. aq. Na$_2$CO$_3$ (50 mL), evaporated on celite and purified by dry column vacuum chromatography (4.0×3.3 cm) on silica gel eluting with a gradient of 0-90% EtOAc in hexane (v/v) followed by 0-50% MeOH in EtOAc (v/v) to give the corresponding sulfonate salt (1.116 g, 90%) as a white solid.

$^1$H-NMR (300 MHz, CD$_3$OD) δ: 7.37-7.21 (15H, m), 4.90 (1H, d, J=11.2 Hz), 4.86 (1H, d, J=10.6 Hz), 4.84 (1H, d, J=11.2 Hz), 4.73 (1H, d, J=3.1 Hz), 4.72 (1H, d, J=11.2 Hz), 4.64 (1H, d, J=12.5 Hz), 4.60 (1H, d, J=11.2 Hz), 4.16 (1H, t, J=9.2 Hz), 3.90 (1H, t, J=9.3 Hz), 3.55 (1H, dd, J=3.4, 9.3 Hz), 3.48 (3H, s), 3.30-3.22 (2H, m), 2.92 (1H, dd, J=10.0, 14.3 Hz). $^{13}$C-NMR (75 MHz, CD$_3$OD) δ: 140.03, 139.57, 139.55 (C), 129.42, 129.31, 129.15, 128.93, 128.89, 128.84, 128.67, 128.59 (CH), 98.53, 83.03, 81.65, 81.52 (CH), 76.44, 75.83, 73.85 (CH$_2$), 68.52 (CH), 55.95 (CH$_3$), 53.65 (CH$_2$). IR (cm$^{-1}$): 3484, 3030, 2922, 1497, 1454, 1360, 1230, 1198, 1177, 1156, 1093, 1058, 1028, 736, 696. MALDI-MS (C$_{28}$H$_{31}$NaO$_8$S): [MNa]$^+$ 573.1536 (calcd. 573.1535). Finally, the obtained sulfonate salt (696 mg, 1.26 mmol) was suspended in anhydrous acetonitrile/CH$_2$Cl$_2$ (10 mL, 1:1 (v/v)) at 0° C., Ph$_3$P (1.002 g, 3.8 mmol) and thionyl chloride (0.40 mL, 5.5 mmol) were added sequentially and the suspension was stirred at room temperature for 13 h. EtOAc/hexane (1:4 (v/v), 100 mL) was added, the suspension was filtered through celite (4×15 mL EtOAc/hexane (1:3 (v/v)) washings) and the filtrate was evaporated and dried shortly under vacuum to give the desired sulfonyl chloride IXa (657 mg, 95%) as a yellowish oil.

$^1$H-NMR (300 MHz, CDCl$_3$) δ: 7.42-7.28 (15H, m), 5.05 (1H, d, J=10.6 Hz), 4.96 (1H, d, J=11.8 Hz), 4.85 (1H, d, J=10.6 Hz), 4.83 (1H, d, J=11.8 Hz), 4.67 (1H, d, J=12.5 Hz), 4.60 (1H, d, J=11.2 Hz), 4.60 (1H, d, J=3.1 Hz), 4.33 (1H, t, J=9.6 Hz), 4.07 (1H, t, J=9.0 Hz), 3.85 (1H, dd, J=1.2, 13.7 Hz), 3.55 (1H, d, J=9.3 Hz), 3.52 (1H, t, J=10.0 Hz), 3.46 (3H, s), 3.26 (1H, t, J=9.5 Hz). $^{13}$C-NMR (75 MHz, CDCl$_3$) δ: 138.02, 137.57, 137.06 (C), 128.58, 128.36, 128.30, 128.23, 128.12, 127.92, 127.66 (CH), 98.00, 81.56, 79.41, 78.49 (CH), 75.85, 74.76, 73.38, 66.75 (CH$_2$), 65.93 (CH), 55.90 (CH$_3$). MALDI-MS (C$_{28}$H$_{31}$ClO$_7$S): [MNa]$^+$ 569.1378 (calcd. 569.1377).

b)

IXb

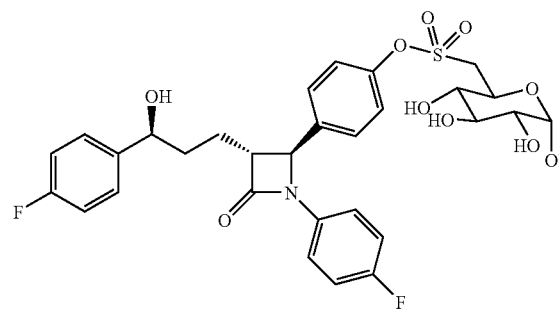

The sulfonyl chloride IXa obtained in step 5a) (197 mg, 0.36 mmol) was suspended in anhydrous CH$_2$Cl$_2$ (5 mL), anhydrous pyridine (0.5 mL) followed by the silylated azetidinone phenol VIa obtained in step 2a) (70.0 mg, 0.13 mmol) were added and the solution was stirred for 22 h, diluted with EtOAc (25 mL) and washed sequentially with sat. aq. NaHCO$_3$ (10 mL) and H$_2$O (10 mL). The organic layer was evaporated on celite and purified by dry column vacuum chromatography (4.3×2.0 cm) on silica gel eluting with a gradient of 0-35% EtOAc in hexane (v/v) to give the corresponding glycosylated azetidinone (125.5 mg, 91%) as a colourless oil/glass.

$^1$H-NMR (300 MHz, CDCl$_3$) δ: 7.37-7.14 (23H, m), 7.00 (2H, t, J=8.7 Hz), 6.95 (2H, t, J=8.7 Hz), 5.05 (1H, d, J=11.2 Hz), 4.97 (1H, d, J=11.2 Hz), 4.84 (1H, d, J=11.8 Hz), 4.82 (1H, d, J=10.6 Hz), 4.69 (1H, t, J=6.8 Hz), 4.67 (1H, d, J=12.5 Hz), 4.60 (1H, d, J=3.7 Hz), 4.56 (1H, d, J=12.5 Hz), 4.54 (1H, d, J=10.6 Hz), 4.29 (1H, t, J=9.5 Hz), 4.06 (1H, t, J=9.0 Hz), 3.57 (1H, t, J=3.1 Hz), 3.53 (1H, d, J=3.1 Hz), 3.46 (3H, s), 3.26 (1H, t, J=9.3 Hz), 3.14 (1H, dd, J=10.0, 14.3 Hz), 2.96 (1H, dt, J=1.9, 6.8 Hz), 1.97-1.78 (4H, m), 0.90 (9H, s), 0.04 (3H, s), −0.13 (3H, s). $^{13}$C-NMR (75 MHz, CDCl$_3$) δ: 166.62, 163.27, 160.37, 160.03, 157.14, 148.91, 140.33, 138.05, 137.63, 137.29, 136.67, 133.45, 133.42 (C), 128.44, 128.31, 128.18, 128.04, 127.96, 127.86, 127.65, 127.15, 127.03, 126.97, 123.15, 118.13, 118.03, 115.93, 115.64, 115.02, 114.75 (CH), 97.92, 81.67, 79.60, 79.23 (CH), 75.78, 74.86 (CH$_2$), 73.78 (CH), 73.37 (CH$_2$), 65.64, 60.66, 60.48 (CH), 55.73 (CH$_3$), 51.63, 38.06 (CH$_2$), 25.85 (CH$_3$), 24.69 (CH$_2$), 18.22 (C), −4.54, −4.87 (CH$_3$). IR (cm$^{-1}$): 3032, 2930, 2858, 1750, 1605, 1510, 1455, 1386, 1252, 1220, 1153, 1086, 1073, 1048, 870, 836, 755, 699. MALDI-MS: [MNa]$^+$ 1056.3969 (calcd. 1056.3964). Anal. Calcd for C$_{58}$H$_{65}$F$_2$NO$_{10}$SiS: C, 67.35; H, 6.33; N, 1.35. Found: C, 67.43; H, 6.44; N, 1.33.

Subsequently the glycosylated azetidinone (105.1 mg, 0.102 mmol) was dissolved in EtOH (5 mL), Pd(OH)$_2$/C (20% (w/w), 33 mg) was added and the suspension was evacuated 4 times with H$_2$ and stirred under an H$_2$-atmosphere for 6 h. The suspension was evaporated on celite and purified by dry column vacuum chromatography (4.2×2.0 cm) on silica gel eluting with a gradient of 0-10% MeOH in CH$_2$Cl$_2$ (v/v) to give the debenzylated azetidinone (63.2 mg, 81%) as a colourless oil.

$^1$H-NMR (300 MHz, acetone-d$_6$) δ: 7.55 (2H, d, J=8.7 Hz), 7.42 (2H, d, J=8.7 Hz), 7.37 (2H, dd, J=5.9, 8.4 Hz), 7.28 (2H, dd, J=5.0, 9.3 Hz), 7.11-7.01 (4H, m), 4.96 (1H, d, J=1.9 Hz), 4.84 (1H, t, J=5.3 Hz), 4.69 (1H, d, J=3.7 Hz), 4.61 (1H, d, J=5.0 Hz), 4.35 (1H, d, J=3.1 Hz), 4.16 (1H, dt, J=1.2, 10.0 Hz), 3.87 (1H, dd, J=1.2, 14.9 Hz), 3.79 (1H, d, J=7.5 Hz), 3.65 (1H, t, J=9.0 Hz), 3.56 (1H, dd, J=10.0, 14.9 Hz), 3.45-3.40 (1H, m), 3.38 (3H, s), 3.27-3.14 (2H, m), 2.00-1.88 (4H, m), 0.87 (9H, s), 0.05 (3H, s), −0.15 (3H, s). $^{13}$C-NMR (75 MHz, acetone-d$_6$) δ: 167.25, 163.96, 160.84, 160.75, 157.65, 150.14, 141.91, 141.87, 138.13, 134.95, 134.91 (C), 128.32, 128.23, 123.84, 118.98, 118.88, 116.43, 116.12, 115.49, 115.21 (CH), 100.74, 74.77, 74.42, 73.55, 73.04, 68.01, 61.25, 60.50 (CH), 55.56 (CH$_3$), 52.83, 38.50 (CH$_2$), 26.16 (CH$_3$), 25.34 (CH$_2$), 18.65 (C), −4.47, −4.71 (CH$_3$). IR (cm$^{-1}$): 3396, 2951, 2931, 2857, 1754, 1701, 1605, 1510, 1426, 1385, 1250, 1220, 1151, 1103, 1088, 1053, 1015, 988, 872, 836, 778. MALDI-MS (C$_{37}$H$_{47}$F$_2$NO$_{10}$SSi): [MNa]$^+$ 786.2559 (calcd. 786.2556).

This debenzylated azetidinone (58.9 mg, 0.077 mmol) was dissolved in anhydrous THF (2.5 mL, teflon bottle), anhydrous pyridine (0.5 mL) followed by HF.pyridine complex (0.5 mL) were added and the solution was stirred for 14.5 h, diluted with ether (20 mL) and washed with sat. aq. NaHCO$_3$ (3×5 mL). The organic layer was evaporated on celite and purified by dry column vacuum chromatography (4.2×2.0 cm) on silica gel eluting with a gradient of 0-10% MeOH in CH$_2$Cl$_2$ (v/v) to give the desired azetidinone IXb (44.9 mg, 90%) as a white solid.

$^1$H-NMR (300 MHz, acetone-d$_6$) δ: 7.56 (2H, d, J=8.7 Hz), 7.43 (2H, d, J=8.7 Hz), 7.37 (2H, dd, J=5.6, 8.7 Hz), 7.30 (2H, dd, J=4.7, 9.0 Hz), 7.06 (2H, d, J=9.3 Hz), 7.03 (2H, d, J=8.7 Hz), 4.99 (1H, d, J=2.5 Hz), 4.69 (1H, d, J=3.7 Hz), 4.61 (1H, d, J=5.0 Hz), 4.42 (1H, d, J=3.7 Hz), 4.34 (1H, bs), 4.15 (1H, dt, J=1.2, 8.7 Hz), 3.86 (1H, dd, J=1.2, 14.9 Hz), 3.79 (1H, d, J=8.1 Hz), 3.65 (1H, t, J=8.7 Hz), 3.57 (1H, dd, J=10.0, 14.9 Hz), 3.44-3.38 (1H, m), 3.38 (3H, s), 3.32-3.14 (2H, m), 2.08-1.86 (4H, m). $^{13}$C-NMR (75 MHz, acetone-d$_6$) δ: 167.42, 163.87, 160.85, 157.67, 150.13, 142.52, 138.18, 134.93 (C), 128.35, 128.22, 128.13, 123.83, 119.01, 118.89, 116.44, 116.13, 115.40, 115.11 (CH), 100.74, 74.77, 73.56, 73.04, 72.77, 68.01, 61.27, 60.56 (CH), 55.56 (CH$_3$), 52.83, 37.54, 25.70 (CH$_2$) IR (cm$^{-1}$): 3395, 2925, 1732, 1604, 1509, 1365, 1219, 1148, 1103, 1051, 1014, 871, 834, 752. MALDI- MS: [MNa]+ 672.1693 (calcd. 672.1691). Anal. Calcd for $C_{31}H_{33}F_2NO_{10}S$: C, 57.31; H, 5.12; N, 2.16. Found: C, 57.34; H, 5.26; N, 2.21.

c)

LiAlH$_4$ (57 mg, 1.5 μmmol) and AlCl$_3$ (200 mg, 1.5 mmol) were suspended in anhydrous ether (15 mL), refluxed for 30 min and cooled to 0° C. The azetidinone IXb obtained under step 5b) (26.8 mg, 0.041 mmol) dissolved in anhydrous THF (1 mL, 2×0.5 mL rinse) was added and after stirring at 0° C. for 10 min, sat. aq. NaHCO$_3$ (1 mL) was added dropwise. The suspension was evaporated on celite and purified by dry column vacuum chromatography (4.7×2.0 cm) on silica gel eluting with a gradient of 0-12% MeOH in CH$_2$Cl$_2$ (v/v) to give the desired azetidine IX (20.4 mg, 78%) as a colourless oil.

$^1$H-NMR (300 MHz, acetone-d$_6$) δ: 7.63-7.59 (2H, m), 7.49-7.42 (2H, m), 7.36-7.29 (2H, m), 7.10-7.01 (2H, m), 6.92-6.77 (2H, m), 6.40-6.35 (2H, m), 4.72 (1H, d, J=3.7 Hz), 4.62 (1H, d, J=5.0 Hz), 4.61 (1H, bs), 4.52 (1H, d, J=6.9 Hz), 4.31 (2H, t, J=4.4 Hz), 4.21-4.15 (2H, m), 3.90 (1H, dd, J=1.2, 14.9 Hz), 3.76 (1H, d, J=8.1 Hz), 3.68 (1H, dd, J=3.7, 9.3 Hz), 3.66-3.57 (2H, m), 3.41 (3H, s, OMe), 3.38-3.31 (1H, m), 3.25 (1H, dt, J=5.0, 13.7 Hz), 2.62 (1H, dd, J=6.8, 14.3 Hz), 1.92-1.84 (1H, m), 1.74-1.57 (3H, m). $^{13}$C-NMR (75 MHz, acetone-d$_6$) δ: 163.90, 160.69, 158.31, 155.22, 149.93, 149.72, 149.52, 142.90, 142.84 (C), 129.60, 129.44, 128.30, 128.24, 128.13, 123.51, 122.99, 115.95, 115.91, 115.66, 115.40, 115.11, 113.87, 113.77, 113.67, 113.57 (CH), 100.84, 74.86, 74.03, 73.68, 73.14, 72.87, 68.09 (CH), 56.67 (CH$_2$), 55.63 (CH$_3$), 52.83 (CH$_2$), 42.78 (CH), 37.60, 29.83 (CH$_2$). IR (cm$^{-1}$): 3390, 2935, 2850, 1605, 1508, 1474, 1366, 1221, 1147, 1052, 1015, 874, 824, 755. MALDI-MS (C$_{31}$H$_{35}$F$_2$NO$_9$S): [MH-H$_2$O]+ 618.1968 (calcd. 618.1973); [MH]+ 636.2045 (calcd. 636.2079); [MNa]+ 658.1901 (calcd. 658.1898).

Example 6

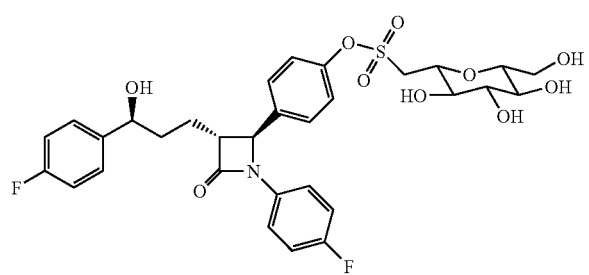

X a)

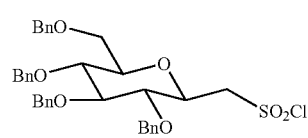

Xa

The above sulfonyl chloride Xa was prepared according to the methods described under step 5a) using C-(Hydroxymethyl)-2,3,4,6-tetra-O-benzyl-β-D-glucopyranoside (prepared according to RajanBabu, T. V.; Reddy, G. S. *J. Org. Chem.* 1986, 51, 5458-5461) as the starting material.

b)

The sulfonyl chloride Xa obtained under step 6a) (871 mg, 1.26 mmol) was suspended in anhydrous CH$_2$Cl$_2$ (10 mL), anhydrous pyridine (1.0 mL) followed by the silylated azetidinone phenol VIa obtained in step 2a) (334 mg, 0.634 mmol) were added and the solution was stirred for 13 h, diluted with EtOAc (50 mL) and washed sequentially with sat. aq. NaHCO$_3$ (20 mL) and H$_2$O (20 mL). The organic layer was evaporated on celite and purified by dry column vacuum chromatography (4.3×3.3 cm) on silica gel eluting with a gradient of 0-100% CH$_2$Cl$_2$ in hexane (v/v) to give the corresponding glycosylated azetidinone (657 mg, 92%) as a white foam.

$^1$H-NMR (300 MHz, CDCl$_3$) δ: 7.37-7.15 (28H, m), 7.01 (2H, t, J=8.7 Hz), 6.96 (2H, t, J=8.7 Hz), 5.03-4.81 (4H, m), 4.73-4.51 (6H, m), 3.95 (1H, t, J=8.4 Hz), 3.78 (4H, bs), 3.57-3.53 (1H, m), 3.48 (1H, d, J=1.2 Hz), 3.40 (1H, t, J=9.0 Hz), 3.24 (1H, dd, J=9.3, 14.9 Hz), 3.02-2.95 (1H, m), 1.97-1.80 (4H, m), 0.92 (9H, s), 0.06 (3H, s), −0.11 (3H, s). $^{13}$C-NMR (75 MHz, CDCl$_3$) δ: 166.72, 163.24, 160.35, 160.01, 157.13, 149.25, 140.37, 140.33, 137.90, 137.65, 137.58, 137.12, 136.97, 136.52, 133.52, 133.48 (C), 128.46, 128.32, 128.28, 128.17, 128.02, 127.97, 127.81, 127.76, 127.67, 127.63, 127.52, 127.13, 127.02, 123.32, 118.13, 118.02, 115.90, 115.60, 115.01, 114.72 (CH), 86.83, 79.13, 78.83, 77.73 (CH), 75.56, 75.00, 74.85 (CH$_2$), 74.19, 73.77 (CH), 73.31 (CH$_2$), 68.36, 60.57, 60.53 (CH), 51.31, 38.03 (CH$_2$), 25.85 (CH$_3$), 24.67 (CH$_2$), 18.20 (C), −4.57, −4.87 (CH$_3$). IR (cm$^{-1}$): 2951, 2929, 2858, 1751, 1605, 1510, 1454, 1386, 1362, 1251, 1220, 1151, 1102, 871, 835, 776, 754, 699. MALDI-MS: [MNa]+ 1146.4440 (calcd. 1146.4434). Anal. Calcd for C$_{65}$H$_{71}$F$_2$NO$_{10}$SiS: C, 69.43; H, 6.36; N, 1.25. Found: C, 69.27; H, 6.47; N, 1.28.

The glycosylated azetidinone obtained above (236 mg, 0.210 mmol) was then dissolved in EtOH/EtOAc (10 mL, 1:1 (v/v)), Pd(OH)$_2$/C (20% (w/w), 73 mg) was added and the suspension was evacuated 4 times with H$_2$ and stirred under an H$_2$-atmosphere for 3.5 h. The suspension was evaporated on celite and purified by dry column vacuum chromatography (4.6×2.0 cm) on silica gel eluting with a gradient of 0-20% MeOH in CH$_2$Cl$_2$ (v/v) to give the debenzylated azetidinone (145 mg, 90%) as a white foam.

$^1$H-NMR (300 MHz, acetone-d$_6$) δ: 7.55 (2H, dd, J=6.5, 8.7 Hz), 7.47 (2H, d, J=8.4 Hz), 7.40-7.20 (4H, m), 7.11-6.98 (4H, m), 4.97 (1H, dd, J=2.3, 10.5 Hz), 4.83 (1H, bs), 4.61 (1H, bs), 4.48 (1H, bs), 4.30 (1H, bs), 3.90-3.81 (3H, m), 3.71-3.64 (1H, m), 3.56-3.38 (5H, m), 3.25-3.14 (2H, m), 2.66 (1H, t, J=7.2 Hz), 1.98-1.81 (4H, m), 0.88 (9H, s), 0.05 (3H, s), −0.15 (3H, s). $^{13}$C-NMR (75 MHz, acetone-d$_6$) δ: 168.30, 161.88, 158.69, 151.25, 142.96, 139.63, 139.16, 139.13, 135.98 (C), 131.66, 131.56, 129.36, 129.28, 124.92, 120.00, 119.90, 117.46, 117.16, 116.62, 116.52 (CH), 82.13, 80.16, 76.75, 75.44, 74.46, 72.35 (CH), 63.64 (CH$_2$), 61.60, 61.55 (CH), 54.03, 39.52 (CH$_2$), 27.20 (CH$_3$), 26.35 (CH$_2$), 19.68 (C), −3.44, −3.69 (CH$_3$). IR (cm$^{-1}$): 3380, 2930, 2858, 1749, 1604, 1510, 1385, 1363, 1220, 1172, 1149, 1088, 1032, 1016, 872, 835, 757. MALDI-MS: [MNa]+ 786.2563 (calcd. 786.2556). Anal. Calcd for C$_{37}$H$_{47}$F$_2$NO$_{10}$SiS: C, 58.17; H, 6.20; N, 1.83. Found: C, 58.02; H, 6.26; N, 1.85.

The debenzylated azetidinone (31.5 mg, 0.041 mmol) was then dissolved in anhydrous THF (2.5 mL, teflon bottle), anhydrous pyridine (0.5 mL) followed by HF-pyridine complex (0.5 mL) were added and the solution was stirred for 24 h, diluted with ether (20 mL) and washed with sat. aq. NaHCO$_3$ (3×5 mL). The organic layer was evaporated on celite and purified by dry column vacuum chromatography (4.3×2.0 cm) on silica gel eluting with a gradient of 0-20% MeOH in CH$_2$Cl$_2$ (v/v) to give the desired azetidinone X (9.8 mg, 37%) as a white solid.

$^1$H-NMR (300 MHz, acetone-d$_6$) δ: 7.55 (2H, d, J=8.7 Hz), 7.47 (2H, d, J=8.7 Hz), 7.36 (2H, dd, J=5.6, 8.7 Hz), 7.29 (2H, dd, J=4.8, 9.2 Hz), 7.06 (2H, d, J=8.7 Hz), 7.03 (2H, d, J=9.0 Hz), 4.98 (1H, d, J=2.5 Hz), 4.68 (1H, bs), 4.58 (1H, bs), 4.38 (1H, bs), 4.27 (1H, bs), 3.89-3.80 (3H, m), 3.66 (1H, d, J=10.6 Hz), 3.54-3.36 (5H, m), 3.24-3.14 (2H, m), 2.00-1.86 (4H, m). $^{13}$C-NMR (75 MHz, acetone-d$_6$) δ: 168.48, 151.29, 143.63, 139.23, 136.09 (C), 129.37, 129.29, 129.19, 124.97, 120.05, 119.94, 117.49, 117.18, 116.46, 116.18 (CH), 82.17, 80.18, 76.78, 74.49, 73.79, 72.42 (CH), 63.67 (CH$_2$), 62.35, 61.63 (CH), 54.06, 38.62, 26.75 (CH$_2$). IR (cm$^{-1}$): 3364, 2924, 1734, 1509, 1388, 1220, 1148, 1102, 872, 835, 769. MALDI-MS (C$_{31}$H$_{33}$F$_2$NO$_{10}$S): [MNa]$^+$ 672.1744 (calcd. 672.1691).

Example 7

XI

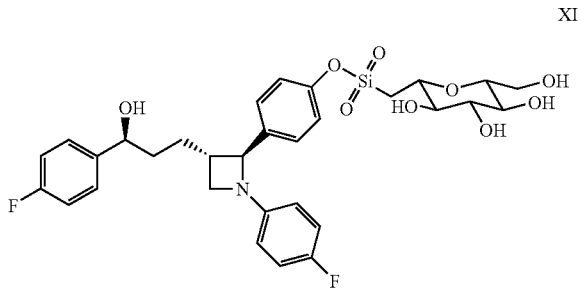

LiAlH$_4$ (57 mg, 1.5 mmol) and AlCl$_3$ (200 mg, 1.5 mmol) were suspended in anhydrous ether (15 mL), refluxed for 30 min and cooled to 0° C. The azetidinone X obtained in Example 6 (41.3 mg, 0.054 mmol) dissolved in anhydrous ether (5 mL) was added and after stirring at 0° C. for 10 min, sat. aq. NaHCO$_3$ (1 mL) was added dropwise. The suspension was evaporated on celite and purified by dry column vacuum chromatography (4.2×2.0 cm) on silica gel eluting with a gradient of 0-20% MeOH in CH$_2$Cl$_2$ (v/v) to give the corresponding azetidine (38.2 mg, 94%) as a white foam.

$^1$H-NMR (300 MHz, acetone-d$_6$) δ: 7.58 (2H, d, J=8.7 Hz), 7.47 (2H, d, J=8.7 Hz), 7.29 (2H, dd, J=5.6, 8.7 Hz), 7.05 (2H, t, J=8.7 Hz), 6.88 (2H, t, J=9.0 Hz), 6.37 (2H, dd, J=4.7, 9.0 Hz), 4.71 (1H, t, J=5.5 Hz), 4.61 (1H; d, J=5.0 Hz), 4.49 (2H, d, J=6.8 Hz), 4.30 (1H, bs), 4.17 (1H, t, J=7.2 Hz), 3.92-3.83 (3H, m), 3.74-3.66 (1H, m), 3.57-3.40 (5H, m), 3.32-3.15 (2H, m), 2.63-2.56 (1H, m), 1.82-1.56 (4H, m), 0.87 (9H, s), 0.04 (3H, s), −0.17 (3H, s). $^{13}$C-NMR (75 MHz, acetone-d$_6$) δ: 164.97, 161.76, 159.31, 156.21, 150.76, 150.47, 150.45, 143.77, 143.11, 143.07 (C), 129.35, 129.22, 124.60, 116.95, 116.65, 116.48, 116.19, 114.86, 114.75 (CH), 82.15, 80.21, 76.81, 75.43, 74.99, 74.52, 72.41 (CH), 63.70, 57.54, 53.95 (CH$_2$), 43.62 (CH), 39.47, 31.22 (CH$_2$), 27.20 (CH$_3$), 19.70 (C), −3.40, −3.68 (CH$_3$). IR (cm$^{-1}$): 3377, 2930, 2856, 1605, 1508, 1472, 1361, 1252, 1222, 1147, 1090, 1015, 871, 836, 776, 760. MALDI-MS (C$_{37}$H$_{49}$F$_2$NO$_9$SSi): [MNa]$^+$ 772.2767 (calcd. 772.2763).

The azetidine obtained above (34.3 mg, 0.046 mmol) was dissolved in anhydrous THF (2.5 mL, teflon bottle), anhydrous pyridine (0.5 mL) followed by HF-pyridine complex (0.5 mL) were added and the solution was stirred for 14 h, diluted with ether (20 mL) and washed with sat. aq. NaHCO$_3$ (3×5 mL). The organic layer was evaporated on celite and purified by dry column vacuum chromatography (4.9×2.0 cm) on silica gel eluting with a gradient of 0-18% MeOH in CH$_2$Cl$_2$ (v/v) to give the desired azetidine XI (20.2 mg, 69%) as a colourless oil.

$^1$H-NMR (300 MHz, acetone-d$_6$) δ: 7.61 (2H, d, J=8.1 Hz), 7.48 (2H, d, J=8.7 Hz), 7.30 (2H, dd, J=5.6, 8.7 Hz), 7.04 (2H, t, J=8.7 Hz), 6.89 (2H, m), 6.38 (2H, dd, J=4.4, 8.7 Hz), 4.60 (2H, d, J=4.4 Hz), 4.52 (1H, d, J=6.8 Hz), 4.45 (1H, d, J=2.5 Hz), 4.29 (2H, d, J=4.4 Hz), 4.19 (1H, t, J=6.8 Hz), 4.03-3.83 (3H, m), 3.80-3.67 (1H, m), 3.60-3.31 (6H, m), 3.25 (1H, p, J=4.4 Hz), 2.62 (1H, dd, J=7.5, 14.3 Hz), 1.92-1.82 (1H, m), 1.78-1.61 (3H, m). $^{13}$C-NMR (75 MHz, acetone-d$_6$) δ: 164.04, 155.14, 149.92, 149.71, 149.47, 142.77, 129.48 (C), 128.19, 128.16, 128.05, 123.52, 123.03, 115.87, 115.58, 115.39, 115.32, 115.05, 113.78, 113.69, 113.61, 113.51 (CH), 81.09, 79.15, 75.76, 73.98, 73.46, 72.75, 71.36 (CH), 62.63, 56.60, 52.88 (CH$_2$), 42.68 (CH), 37.52, 29.61 (CH$_2$). IR (cm$^{-1}$): 3370, 2933, 1605, 1508, 1474, 1360, 1220, 1146, 1087, 1015, 873, 823, 771. MALDI-MS (C$_{31}$H$_{35}$F$_2$NO$_9$S): [MH-H$_2$O]$^+$ 618.1973 (calcd. 618.1973); [M]$^+$ 635.1996 (calcd. 635.2001); [MNa]$^+$ 658.1900 (calcd. 658.1898).

Example 8

XII

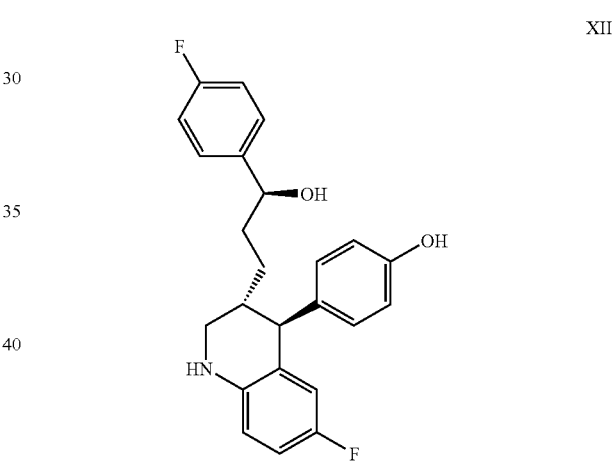

a)

XIIa

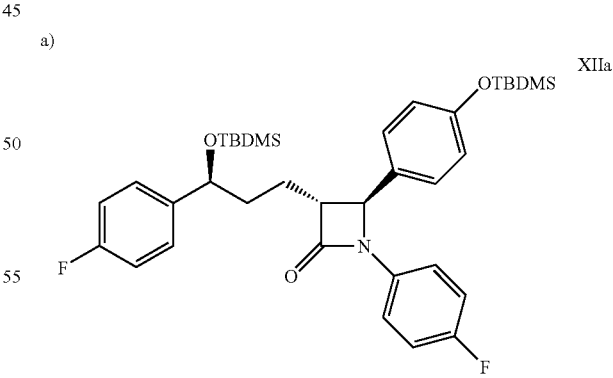

Ezetimibe (commercially obtained or synthesized according to Wu, G. Z. et al., *J. Org. Chem.* 1999; 279 mg, 0.681 mmol) was dissolved in anhydrous DMF (5 mL), imidazole (262 mg, 3.84 mmol) and TBDMSCl (500 mg, 3.32 mmol) were added sequentially and the solution was stirred for 5 h followed by addition of 50% sat. aq. NaHCO$_3$ (50 mL). After extraction with EtOAc (4×20 mL), the combined organic layer was washed successively with sat. aq. NaHCO$_3$ (20 mL) and H$_2$O (20 mL), evaporated on celite and purified by dry column vacuum chromatography (3.8×3.3 cm) on silica gel eluting with a gradient of 0-10% EtOAc in hexane (v/v) to give the fully silylated azetidinone XIIa (424 mg, 97%) as a colourless oil.

$^1$H-NMR (300 MHz, CDCl$_3$) δ: 7.25-7.21 (4H, m), 7.17 (2H, d, J=8.1 Hz), 6.98 (2H, t, J=8.7 Hz), 6.91 (2H, t, J=8.7 Hz), 6.83 (2H, d, J=8.1 Hz), 4.66 (1H, t, J=5.6 Hz), 4.51 (1H, d, J=2.5 Hz), 3.08-3.02 (1H, m), 1.96-1.78 (4H, m), 0.98 (9H, s), 0.88 (9H, s), 0.20 (6H, s), 0.02 (3H, s), −0.16 (3H, s). $^{13}$C-NMR (75 MHz, CDCl$_3$) δ: 167.27, 163.28, 160.27, 160.04, 157.06, 155.71, 140.58, 140.54, 133.89, 133.86 (C), 129.99, 127.22, 127.11, 126.94, 120.56, 118.24, 118.15, 115.74, 115.44, 114.99, 114.72 (CH), 73.84, 61.08, 60.44 (CH), 38.08 (CH$_2$), 25.90, 25.68 (CH$_3$), 24.75 (CH$_2$), 18.26, 18.24 (C), −4.28, −4.52, −4.83 (CH$_3$). IR (cm$^{-1}$): 2954, 2930, 2858, 1752, 1607, 1510, 1385, 1259, 1223, 1101, 1085, 914, 834, 778. MALDI-MS: [MH-TBDMSOH]$^+$ 506.2329 (calcd. 506.2327); [MH]$^+$ 638.3289 (calcd. 638.3297); [MNa]$^+$ 660.3117 (calcd. 660.3117). Anal. Calcd for C$_{36}$H$_{49}$F$_2$NO$_3$Si$_2$: C, 67.78; H, 7.74; N, 2.20. Found: C, 67.70; H, 7.60; N, 2.02.

b)

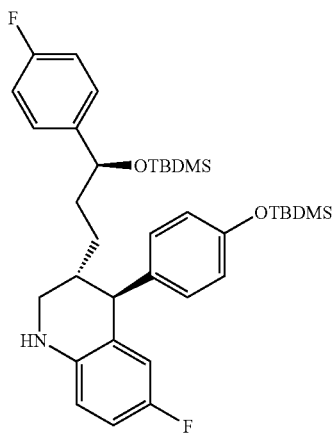

XIIb

LiAlH$_4$ (57 mg, 1.5 mmol) and AlCl$_3$ (200 mg, 1.5 mmol) were suspended in anhydrous ether (15 mL), refluxed for 40 min and cooled to 0° C. The fully silylated azetidinone XIIa obtained under step 8a) (180.8 mg, 0.283 mmol) dissolved in anhydrous ether (5 mL) was added and after stirring at 0° C. for 30 min, H$_2$O (1 mL) was added dropwise. The suspension was evaporated on celite and purified by dry column vacuum chromatography (3.5×3.3 cm) on silica gel eluting with a gradient of 0-50% CH$_2$Cl$_2$ in hexane (v/v) to give the desired bicyclic amine XIIb (110.8 mg, 63%) as a colourless oil.

$^1$H-NMR (300 MHz, CDCl$_3$) δ: 7.18-7.14 (2H, m), 6.95 (2H, t, J=8.7 Hz), 6.88 (2H, d, J=8.7 Hz), 6.74 (2H, d, J=8.1 Hz), 6.68 (1H, dd, J=2.8, 8.4 Hz), 6.44 (1H, dd, J=6.5, 8.7 Hz), 6.38 (1H, dd, J=2.8, 9.6 Hz), 4.48 (1H, dd, J=5.0, 6.8 Hz), 3.78 (1H, bs), 3.61 (1H, d, J=7.5 Hz), 3.26 (1H, dd, J=3.1, 11.2 Hz), 2.91 (1H, dd, J=7.8, 11.5 Hz), 1.91-1.85 (1H, m), 1.68-1.44 (3H, m), 1.16-1.04 (1H, m), 0.99 (9H, s), 0.80 (9H, s), 0.20 (6H, s), 0.06 (3H, s), −0.21 (3H, s). $^{13}$C-NMR (75 MHz, CDCl$_3$) δ: 163.60, 160.36, 157.37, 154.27, 141.53, 141.01, 138.13 (C), 130.07, 127.56, 127.46, 125.58, 125.50, 120.01, 117.27, 116.98, 115.17, 114.89, 114.78, 114.08, 113.79 (CH), 74.64, 48.97 (CH), 44.52 (CH$_2$), 39.89 (CH), 38.67, 28.28 (CH$_2$), 26.00, 25.90 (CH$_3$), 18.38, 18.32 (C), −4.16, −4.43, −4.77 (CH$_3$). IR (cm$^{-1}$): 2955, 2930, 2858, 1607, 1506, 1472, 1408, 1361, 1258, 1222, 1170, 1144, 1085, 1006, 915, 837, 808, 779, 735, 667. MALDI-MS (C$_{36}$H$_{51}$F$_2$NO$_2$Si$_2$): [MH-TBDMSOH]$^+$ 492.2517 (calcd. 492.2534); [M]$^+$ 623.3414 (calcd. 623.3426). Anal. Calcd for C$_{36}$H$_{51}$F$_2$NO$_2$Si$_2$: C, 69.30; H, 8.24; N, 2.24. Found: C, 69.47; H, 8.32; N, 2.15.

c)

The bicyclic amine XIIb obtained under step 8b) (39.8 mg, 0.064 mmol) was dissolved in THF (5 mL), TBAF (0.5 mL, 1M in THF) was added and the solution was stirred for 21 h, evaporated on celite and purified by dry column vacuum chromatography (3.7×2.0 cm) on silica gel eluting with a gradient of 0-100% EtOAc in hexane (v/v) to give the desired amine XII (27.7 mg, quant.) as a yellowish solid.

$^1$H-NMR (300 MHz, CDCl$_3$) δ: 7.19-7.15 (2H, m), 6.97 (2H, t, J=8.7 Hz), 6.87 (2H, d, J=8.4 Hz), 6.74-6.66 (3H, m), 6.46 (1H, dd, J=5.0, 8.7 Hz), 6.38 (1H, dd, J=2.2, 9.0 Hz), 5.54 (1H, bs), 4.52 (1H, t, J=6.5 Hz), 3.61 (1H, d, J=7.2 Hz), 3.26 (1H, dd, J=3.4, 11.5 Hz), 2.90 (1H, dd, J=7.5, 11.5 Hz), 1.95-1.86 (1H, m), 1.78-1.68 (2H, m), 1.52-1.41 (1H, m), 1.19-1.06 (1H, m). $^{13}$C-NMR (75 MHz, CDCl$_3$) δ: 163.55, 160.30, 157.10, 154.25, 154.00, 140.44, 139.95, 139.90, 137.07 (C), 129.90, 127.46, 127.36, 125.24, 116.99, 116.70, 115.28, 115.26, 115.21, 115.15, 115.00, 114.95, 114.84, 113.91, 113.61 (CH), 73.94, 48.53 (CH), 43.98 (CH$_2$), 39.73 (CH), 36.43, 27.95 (CH$_2$). IR (cm$^{-1}$): 3335, 2925, 2853, 1607, 1511, 1223, 913, 836, 744. MALDI-MS (C$_{24}$H$_{23}$F$_2$NO$_2$) [MH-H$_2$O]$^+$ 378.1661 (calcd. 378.1670); [M]$^+$ 395.1689 (calcd. 395.1670)

Example 9

XIII

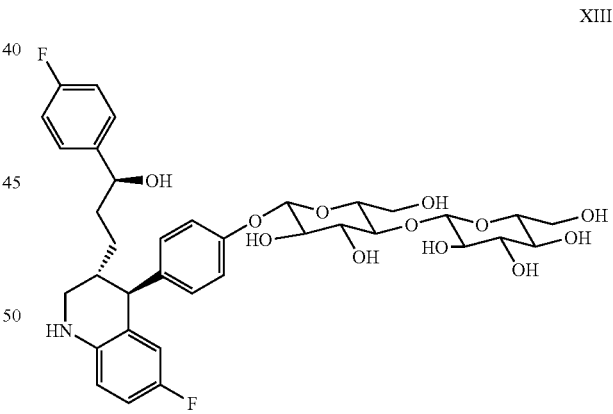

The bicyclic amine XIIb obtained in step 8b) (503 mg, 0.806 mmol) was dissolved in THF (15 mL) at 0° C., TBAF (1.5 mL, 1M in THF) was added and the solution was stirred at 0° C. for 1.5 h, diluted with EtOAc (50 mL) and washed successively with sat. aq. NaHCO$_3$ (20 mL) and H$_2$O (20 mL). The organic layer was evaporated on celite and purified by dry column vacuum chromatography (3.4×3.3 cm) on silica gel eluting with a gradient of 0-30% EtOAc in hexane (v/v) to give the corresponding phenol (344.2 mg, 84%) as a light yellow foam.

$^1$H-NMR (300 MHz, CDCl$_3$) δ: 7.16 (2H, dd, J=5.6, 8.1 Hz), 6.95 (2H, t, J=8.7 Hz), 6.90 (2H, d, J=8.7 Hz), 6.72 (2H, d, J=8.7 Hz), 6.72-6.67 (1H, m), 6.48 (1H, dd, J=4.4, 8.7 Hz), 6.39 (1H, dd, J=2.7, 9.6 Hz), 4.49 (1H, dd, J=5.6, 6.8 Hz), 4.40 (1H, bs), 3.61 (1H, d, J=7.5 Hz), 3.28 (1H, dd, J=2.7, 11.2 Hz), 2.92 (1H, dd, J=8.1, 11.2 Hz), 1.93-1.87 (1H, m), 1.73-1.47 (3H, m), 1.20-1.15 (1H, m), 0.81 (9H, s), 0.06 (3H, s), −0.20 (3H, s). $^{13}$C-NMR (75 MHz, CDCl$_3$) δ: 163.16, 159.93, 157.15, 154.03, 141.13, 141.09, 140.43, 140.40, 137.05 (C), 129.95, 127.21, 127.11, 125.69, 125.62, 116.92, 116.62, 115.23, 114.98, 114.87, 114.83, 114.55, 113.83, 113.53 (CH), 74.36, 48.77 (CH), 44.49 (CH$_2$), 39.78 (CH), 38.46, 28.07 (CH$_2$), 25.81 (CH$_3$), 18.17 (C), −4.52, −4.90 (CH$_3$). IR (cm$^{-1}$): 3338, 2954, 2929, 2857, 1606, 1508, 1475, 1462, 1361, 1251, 1221, 1084, 836, 775, 760. MALDI-MS (C$_{30}$H$_{37}$F$_2$NO$_2$Si): [MH-TBDMSOH]$^+$ 378.1657 (calcd. 378.1670); [M]$^+$ 509.2553 (calcd. 509.2562).

The phenol obtained above (79 mg, 0.15 mmol) and 2,3,6-tri-O-acetyl-4-O-(2,3,4,6-tetra-O-β-D-glucopyranosyl)-α-D-glucopyranosyl 1-(2,2,2-trichloroacetimidate) (prepared according to Buijsman, R. C. et al., *Bioorg. Med. Chem.* 1999, 7, 1881-1890; 267 mg, 0.34 mmol) were then dissolved in anhydrous CH$_2$Cl$_2$ (2 mL) at −25° C. and BF$_3$.OEt$_2$ in CH$_2$Cl$_2$ (1:9 (v/v), 0.10 mL, 0.08 mmol) was added. After stirring for 2.5 h at −25 to −20° C., additional BF$_3$.OEt$_2$ (0.05 mL, 0.39 mmol) was added and after additional 1 h at −25 to −20° C., sat. aq. NH$_4$Cl (10 mL) and EtOAc (10 mL) were added. The layers were separated and the aqueous phase was extracted with EtOAc (3×10 mL). The combined organic layer was washed successively with sat. aq. NaHCO$_3$ (10 mL) and H$_2$O (10 mL), evaporated on celite and purified by dry column vacuum chromatography (4.5×2.0 cm) on silica gel eluting with a gradient of 0-70% EtOAc in hexane (v/v) to give the glycosylated amine (169 mg, 97%) as a white foam.

$^1$H-NMR (300 MHz, CDCl$_3$) δ: 7.12 (2H, dd, J=5.6, 8.7 Hz), 6.94-6.84 (6H, m), 6.66 (1H, dt, J=2.5, 8.1 Hz), 6.42 (1H, dd, J=4.4, 8.7 Hz), 6.29 (1H, dd, J=2.7, 9.6 Hz), 5.29-4.90 (6H, m), 4.54-4.43 (3H, m), 4.37 (1H, dd, J=4.4, 12.5 Hz), 4.16-4.02 (2H, m), 3.86 (1H, t, J=9.0 Hz), 3.77-3.64 (2H, m), 3.60 (1H, d, J=7.5 Hz), 3.23 (1H, dd, J=2.7, 11.5 Hz), 2.88 (1H, dd, J=8.1, 11.2 Hz), 2.07-1.96 (21H, m), 1.87-1.75 (1H, m), 1.70-1.38 (3H, m), 1.13-0.97 (1H, m), 0.76 (9H, s), −0.10 (3H, s), −0.25 (3H, s). $^{13}$C-NMR (75 MHz, CDCl$_3$) δ: 170.38, 170.09, 169.67, 169.47, 169.20, 168.96, 163.25, 160.01, 156.95, 155.27, 153.85, 141.10, 140.73, 140.10 (C), 129.91, 127.21, 127.11, 124.80, 116.68, 114.83, 114.56, 113.62 (CH), 100.71, 98.80, 76.33, 74.20, 72.81, 72.69, 72.42, 71.89, 71.48, 71.27, 67.63 (CH), 61.84, 61.42 (CH$_2$), 48.71 (CH), 44.19 (CH$_2$), 39.61 (CH), 38.27, 27.85 (CH$_2$), 25.64, 20.67, 20.58, 20.43 (CH$_3$), 17.96 (C), −4.76, −5.14 (CH$_3$). IR (cm$^{-1}$): 2955, 2858, 1756, 1506, 1368, 1223, 1049, 837, 770. MALDI-MS (C$_{56}$H$_{71}$F$_2$NO$_{19}$Si): [MNa]$^+$ 1150.4235 (calcd. 1150.4255).

The glycosylated amine obtained above (370 mg, 0.328 mmol) was then dissolved in THF (10 mL), TBAF (1.0 mL, 1M in THF) was added and the solution was stirred for 27 h, diluted with EtOAc (40 mL) and washed successively with sat. aq. NaHCO$_3$ (15 mL) and H$_2$O (15 mL). The organic layer was evaporated and the crude intermediate [MALDI-MS (C$_{50}$H$_{57}$F$_2$NO$_{19}$): [MNa]$^+$ 1036.3394 (calcd. 1036.3391)] was dissolved in MeOH/Et$_3$N/THF (12 mL, 1:1:2 (v/v/v)), H$_2$O (10.5 mL) was added dropwise and the solution was stirred for 18 h. sat. aq. NaHCO$_3$ (1 mL) was added dropwise and the suspension was evaporated on celite and purified by dry column vacuum chromatography (4.0×3.3 cm) on silica gel eluting with a gradient of 0-25% MeOH in EtOAc (v/v) to give the desired bicyclic amine XIII (80.5 mg, 34%) as a white solid after coevaporation with hexane (20 mL).

$^1$H-NMR (300 MHz, CD$_3$OD) δ: 7.20 (2H, dd, J=5.6, 8.7 Hz), 7.02-6.93 (6H, m), 6.65 (1H, dt, J=2.5, 8.7 Hz), 6.54 (1H, dd, J=5.0, 8.7 Hz), 6.23 (1H, dd, J=2.5, 10.0 Hz), 4.94 (1H, d, J=7.5 Hz), 4.47-4.43 (2H, m), 3.92 (2H, bs), 3.90 (1H, d, J=10.6 Hz), 3.72-3.52 (6H, m), 3.43-3.22 (5H, m), 2.86 (1H, dd, J=8.1, 11.8 Hz), 1.96-1.84 (1H, m), 1.80-1.68 (2H, m), 1.50-1.35 (1H, m), 1.17-1.03 (1H, m). $^{13}$C-NMR (75 MHz, CD$_3$OD) δ: 164.71, 161.49, 157.30, 155.12, 142.58, 141.98, 141.95, 140.78 (C), 130.89, 128.83, 128.72, 126.64, 126.56, 117.52, 117.36, 117.09, 115.86, 115.57 (CH), 104.44, 101.98, 80.21, 78.01, 77.76, 76.49, 76.22, 74.83, 74.58, 74.41, 71.29 (CH), 62.39, 61.63 (CH$_2$), 50.00 (CH), 45.09 (CH$_2$), 40.95 (CH), 37.38, 29.09 (CH$_2$). MALDI-MS (C$_{36}$H$_{43}$F$_2$NO$_{12}$): [MNa]$^+$ 742.2654 (calcd. 742.2651).

Example 10

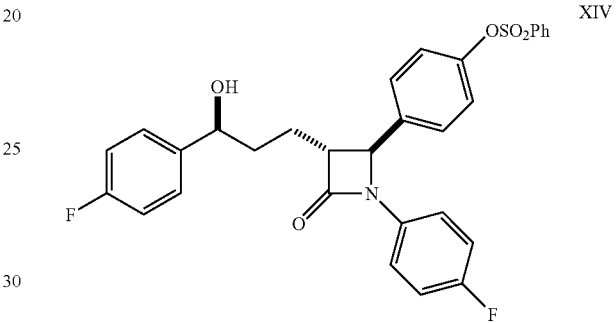

XIV

The silylated azetidinone phenol VIa obtained in step 2a) (104.0 mg, 0.199 mmol) was dissolved in anhydrous CH$_2$Cl$_2$ (10 mL), anhydrous pyridine (0.5 mL) followed by PhSO$_2$Cl (0.10 mL, 0.78 mmol) were added and the solution was stirred for 19 h. Additional PhSO$_2$Cl (0.10 mL, 0.78 mmol) was added and the solution was stirred for further 69 h, diluted with EtOAc (50 mL) and washed sequentially with sat. aq. NaHCO$_3$ (20 mL) and H$_2$O (20 mL). The organic layer was evaporated on celite and purified by dry column vacuum chromatography (4.2×3.3 cm) on silica gel eluting with a gradient of 0-100% CH$_2$Cl$_2$ in hexane (v/v) followed by 0.5-1.0% MeOH in CH$_2$Cl$_2$ (v/v) to give the corresponding benzene sulfonate (92.0 mg, 70%) as a colourless oil.

R$_f$(1% MeOH in CH$_2$Cl$_2$ (v/v)) 0.72; $^1$H-NMR (300 MHz, CDCl$_3$) δ: 7.83 (2H, d, J=7.5 Hz), 7.66 (1H, t, J=7.5 Hz), 7.51 (2H, t, J=7.5 Hz), 7.25-7.14 (6H, m), 7.00 (2H, d, J=8.7 Hz), 6.97 (2H, d, J=8.7 Hz), 6.91 (2H, t, J=8.7 Hz), 4.66 (1H, dd, J=4.4, 6.2 Hz), 4.55 (1H, d, J=1.9 Hz), 3.02-2.96 (1H, m), 1.94-1.75 (4H, m), 0.87 (9H, s), 0.00 (3H, s), −0.16 (3H, s). $^{13}$C-NMR (75 MHz, CDCl$_3$) δ: 166.82, 163.44, 160.51, 157.29, 149.35, 140.54 (C), 136.77 (CH), 135.26, 134.32, 133.56, 129.13 (C), 128.31, 127.27, 127.17, 127.08, 123.15, 118.23, 118.12, 115.93, 115.63, 115.09, 114.82, 73.76, 60.53, 60.40 (CH), 37.92 (CH$_2$), 25.75 (CH$_3$), 24.59 (CH$_2$), 18.10 (C), −4.71, −5.03 (CH$_3$). IR (cm$^{-1}$): 2953, 2930, 2857, 1752, 1605, 1510, 1450, 1382, 1252, 1221, 1202, 1181, 1155, 1093, 1016, 868, 835, 776, 753, 700, 687. MALDI-MS (C$_{36}$H$_{39}$F$_2$NO$_5$SSi): [MH-TBDMSOH]$^+$ 532.1395 (calcd. 532.1394); [MNa]$^+$ 686.2185 (calcd. 686.2184).

This benzene sulfonate (90.0 mg, 0.136 mmol) was dissolved in anhydrous THF (2.5 mL, teflon bottle) at 0° C., anhydrous pyridine (0.5 mL) followed by HF-pyridine complex (0.5 mL) were added and the solution allowed slowly to warm to room temperature. After 14 h, the mixture was diluted with ether (20 mL) and washed with sat. aq. NaHCO$_3$ (3×5 mL). The organic layer was evaporated on celite and purified by dry column vacuum chromatography (5.0×2.0 cm) on silica gel eluting with a gradient of 0-100% CH$_2$Cl$_2$ in hexane (v/v) followed by 1-7% MeOH in CH$_2$Cl$_2$ (v/v) to give β-lactam XIV (69.2 mg, 93%) as a white foam.

R$_f$ (3% MeOH in CH$_2$Cl$_2$ (v/v)) 0.33; $^1$H-NMR (300 MHz, CDCl$_3$) δ: 7.82 (2H, dd, J=1.2, 7.5 Hz), 7.67 (1H, tt, J=1.2, 7.5 Hz), 7.51 (2H, t, J=7.5 Hz), 7.29-7.22 (4H, m), 7.15 (2H, dd, J=4.4, 8.7 Hz), 6.99 (2H, t, J=8.7 Hz), 6.98 (2H, d, J=8.7 Hz), 6.92 (2H, t, J=8.7 Hz), 4.68 (1H, dd, J=5.6, 6.2 Hz), 4.60 (1H, d, J=1.9 Hz), 3.06-2.98 (1H, m), 2.55 (1H, bs), 2.04-1.84 (4H, m). $^{13}$C-NMR (75 MHz, CDCl$_3$) δ: 166.87, 163.56, 160.44, 160.31, 157.22, 149.23, 139.84, 139.79 (C), 136.46 (CH), 135.10, 134.26, 133.37 (C), 129.07, 128.22, 127.26, 127.16, 127.02, 123.07, 118.21, 118.11, 115.93, 115.62, 115.36, 115.07, 72.98, 60.50, 60.32 (CH), 36.54, 25.09 (CH$_2$). IR (cm$^{-1}$): 3440, 3069, 3017, 2927, 2862, 1747, 1604, 1510, 1450, 1426, 1378, 1221, 1201, 1180, 1154, 1094, 1016, 868, 835, 753, 700, 687, 668. MALDI-MS (C$_{30}$H$_{25}$F$_2$NO$_5$S): [MH—H$_2$O]$^+$ 532.1388 (calcd. 532.1394); [MNa]$^+$ 572.1302 (calcd. 572.1319).

Example 11

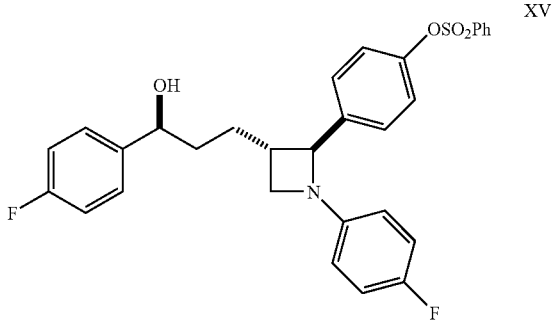

LiAlH$_4$ (57 mg, 1.5 mmol) and AlCl$_3$ (202 mg, 1.5 mmol) were suspended in anhydrous ether (15 mL), refluxed for 30 min and cooled to 0° C. β-Lactam XIV obtained in example 10 (62.8 mg, 0.114 mmol) dissolved in anhydrous ether (5 mL) was added and after stirring at 0° C. for 20 min, sat. aq. NaHCO$_3$ (1 mL) was added dropwise. The suspension was evaporated on celite and purified by dry column vacuum chromatography (4.8×2.0 cm) on silica gel eluting with a gradient of 0-50% EtOAc in hexane (v/v) to give azetidine XV (24.5 mg, 40%) as a white foam.

R$_f$ (1:1 EtOAc/hexane (v/v)) 0.46; $^1$H-NMR (300 MHz, CDCl$_3$) δ: 7.88-7.82 (2H, m), 7.70-7.63 (1H, m), 7.55-7.47 (2H, m), 7.38-7.30 (2H, m), 7.24-7.19 (2H, m), 7.05-6.98 (4H, m), 6.83 (2H, t, J=8.7 Hz), 6.26 (2H, dd, J=4.4, 9.3 Hz), 4.56 (1H, dd, J=5.0, 7.5 Hz), 4.36 (1H, d, J=6.8 Hz), 4.09 (1H, dd, J=6.8, 7.5 Hz), 3.27 (1H, dd, J=6.8, 7.5 Hz), 2.79 (1H, d, J=5.6 Hz), 2.52 (1H, dd, J=6.8, 7.5 Hz), 1.89-1.52 (4H, m). $^{13}$C-NMR (75 MHz, CDCl$_3$) δ: 163.65, 160.40, 157.73, 154.61, 148.65, 148.07, 141.59, 139.94, 135.36 (C), 134.11, 129.24, 129.03, 128.30, 127.28, 127.17, 122.54, 115.45, 115.15, 112.99, 112.90, 73.47, 73.32 (CH), 55.89 (CH$_2$), 41.74 (CH), 36.30, 29.93 (CH$_2$). IR (cm$^{-1}$): 3411, 2937, 2853, 1604, 1508, 1474, 1450, 1374, 1221, 1198, 1175, 1151, 1093, 1016, 867, 823, 752, 700, 686. MALDI-MS (C$_{30}$H$_{27}$F$_2$NO$_4$S): [MH-H$_2$O]$^+$ 518.1596 (calcd. 518.1601); [M]$^+$ 535.1619 (calcd. 535.1629); [MNa]$^+$ 558.1512 (calcd. 558.1527).

Example 12

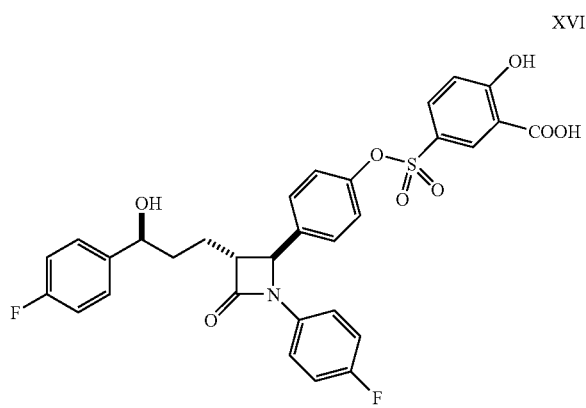

The silylated azetidinone phenol VIa obtained in step 2a) (105 mg, 0.201 mmol) was dissolved in anhydrous CH$_2$Cl$_2$ (5 mL), anhydrous pyridine (0.5 mL, 5.0 mmol) and 3-carboxy-4-hydroxybenzene sulfonyl chloride (prepared according to Stewart, J. *J. Chem. Soc.* 1922, 121, 2555-2561; 223 mg, 0.94 mmol) were added sequentially and the suspension was stirred at room temperature for 63 h. The mixture was evaporated on celite and purified by dry column vacuum chromatography (4.7×2.0 cm) on silica gel eluting with a gradient of 0-15% MeOH in CH$_2$Cl$_2$ (v/v) to give the corresponding silylated sulfonate (76.2 mg, 53%) as a colourless oil.

R$_f$ (20% MeOH in CH$_2$Cl$_2$ (v/v)) 0.68; $^1$H-NMR (300 MHz, CD$_3$CN) δ: 10.36 (1H, bs), 8.31 (1H, bs), 7.69 (1H, bs), 7.31-7.13 (8H, m), 7.00 (2H, t, J=7.5 Hz), 6.89 (2H, t, J=8.1 Hz), 6.57 (1H, bs), 4.72 (1H, bs), 4.65 (1H, bs), 3.12 (1H, bs), 2.98 (1H, bs), 1.88-1.72 (4H, m), 0.84 (9H, s), 0.01 (3H, s), −0.18 (3H, s). $^{13}$C-NMR (75 MHz, CD$_3$CN) δ: 168.91, 167.92, 163.57, 160.97, 157.89, 150.74, 142.17, 142.14, 137.17, 134.89 (C), 128.57, 128.45, 128.16, 123.34, 119.23, 119.17, 118.18, 116.68, 116.38, 115.71, 115.43, 74.39, 61.14, 60.64 (CH), 38.40 (CH$_2$), 26.12 (CH$_3$), 25.10 (CH$_2$), 18.65 (C), −4.53, −4.69 (CH$_3$). IR (cm$^{-1}$): 3450, 2954, 2930, 2858, 1751, 1696, 1606, 1585, 1510, 1478, 1386, 1339, 1293, 1220, 1194, 1126, 1103, 1087, 1063, 1042, 835, 777, 758. MALDI-MS (C$_{37}$H$_{39}$F$_2$NO$_8$SSi): [M-H+2Na]$^+$ 768.1851 (calcd. 768.1851).

This silylated sulfonate (74.2 mg, 62.5 mmol) was dissolved in anhydrous THF (2.5 mL, teflon bottle) at 0° C., anhydrous pyridine (0.5 mL) followed by HF.pyridine complex (0.5 mL) were added and the solution allowed slowly to warm to room temperature. After 15 h, sat. aq. NaHCO$_3$ (15 mL) was added and the suspension was evaporated on celite and purified by dry column vacuum chromatography (4.4× 2.0 cm) on silica gel eluting with a gradient of 0-25% MeOH in EtOAc (v/v) to give sulfonate XVI (43.6 mg, 70%) as a white solid.

R$_f$ (1:3 MeOH/EtOAc (v/v)) 0.44; $^1$H-NMR (300 MHz, CD$_3$OD) δ: 8.53 (1H, d, J=1.9 Hz), 7.99 (1H, dd, J=2.5, 8.7 Hz), 7.48 (1H, d, J=8.7 Hz), 7.35-7.28 (6H, m), 7.07-6.97 (5H, m), 4.93 (1H, d, J=2.5 Hz), 4.62 (1H, dd, J=5.0, 6.2 Hz), 3.17-3.08 (1H, m), 1.97-1.84 (4H, m). $^{13}$C-NMR (75 MHz, CD$_3$OD) δ: 169.19, 164.04, 151.43, 142.04, 142.01, 138.00

(C), 137.35 (CH), 134.92 (C), 129.46, 128.72, 128.62, 128.44, 123.54, 119.86, 119.76, 118.63, 116.82, 116.51, 115.98, 115.68 (CH), 112.37 (C), 73.73, 61.65, 61.39 H(CH), 37.49, 26.18 (CH$_2$). MALDI-MS (C$_{31}$H$_{25}$F$_2$NO$_8$S): [M−H+ 2Na]$^+$ 654.1000 (calcd. 654.0986).

Example 13

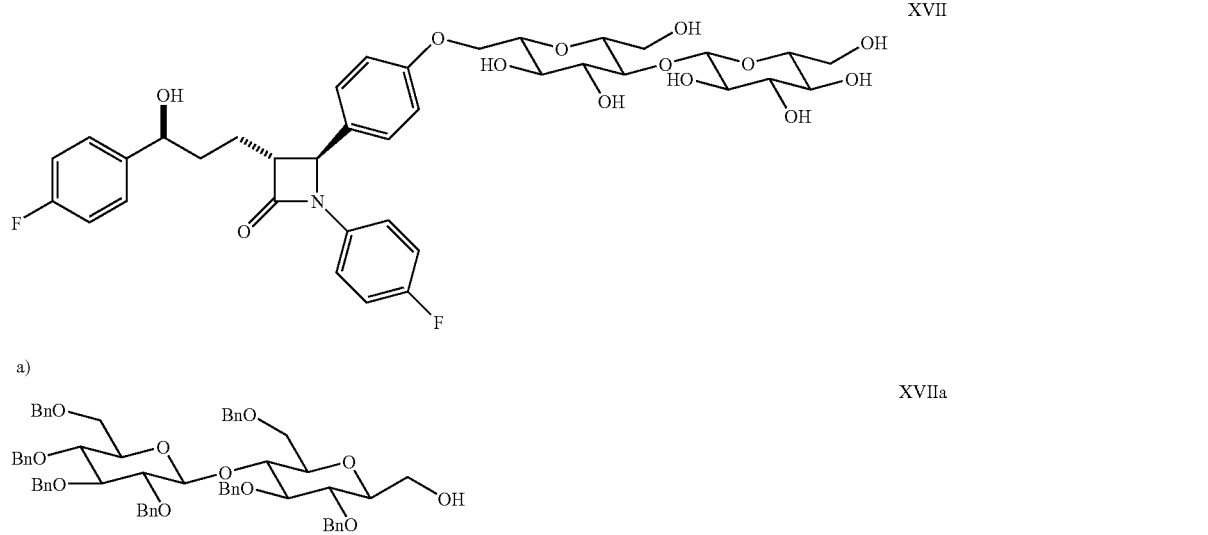

The silylated azetidinone phenol VIa obtained in step 2a) (80.3 mg, 0.153 μmmol) and alcohol XVIIa (prepared according to Spak, S. J.; Martin, O. R. *Tetrahedron* 2000, 56, 217-224; 101.5 mg, 0.103 mmol) were dissolved in anhydrous THF (10 mL) at 0° C., Bu$_3$P (50 mg, 0.20 mmol) and 1,1'-(azodicarbonyl)dipiperidine (39.5 mg, 0.17 mmol) were added sequentially and the suspension was allowed to warm to ambient temperature over several hours. After stirring at room temperature for 26 h, EtOAc/hexane (1:4 (v/v), 30 mL) was added and the suspension was filtered through celite (2×10 mL EtOAc/hexane (1:4 (v/v)) washings). The filtrate was evaporated on celite and purified by dry column vacuum chromatography (4.5×2.0 cm) on silica gel eluting with a gradient of 0-25% EtOAc in hexane (v/v) to give a 1:1 mixture of the corresponding C-glycoside and unreacted phenol VIa (49.7 mg) as a white foam.

R$_f$ (1:1 EtOAc/hexane (v/v)) 0.64; $^{13}$C-NMR (75 MHz, CDCl$_3$) δ: 167.39, 163.27, 160.31, 158.82, 157.09, 140.54, 140.49, 139.05, 138.37, 138.29, 138.19, 137.85, 133.78, 133.73, 129.40, 128.96, 128.23, 128.12, 128.04, 127.94, 127.86, 127.73, 127.63, 127.57, 127.49, 127.41, 127.20, 127.10, 126.87, 118.30, 118.19, 116.01, 115.78, 115.49, 115.30, 114.99, 114.71, 102.41, 85.35, 84.84, 82.70, 79.29, 78.01, 77.82, 77.19, 75.64, 75.25, 75.10, 75.02, 74.96, 74.81, 73.84, 73.26, 68.99, 68.15, 67.49, 61.07, 60.44, 38.09, 25.90, 24.72, 18.25, −4.53, −4.83. MALDI-MS (C$_{92}$H$_{99}$F$_2$NO$_{13}$Si): [MNa]$^+$ 1514.6763 (calcd. 1514.6751).

This mixture of the C-glycoside and phenol VIa (49.7 mg) was dissolved in EtOH/EtOAc (10 mL, 1:1 (v/v)), Pd(OH)$_2$/C (20% (w/w), 31 mg) was added and the suspension was evacuated 4 times with H$_2$ and stirred under an H$_2$-atmosphere for 3 h. The suspension was evaporated on celite and purified by dry column vacuum chromatography (4.6×2.0 cm) on silica gel eluting with a gradient of 0-20% MeOH in CH$_2$Cl$_2$ (v/v) to give the corresponding debenzylated C-glycoside (18.7 mg, 21% from VIa) as a colourless oil.

R$_f$ (20% MeOH in CH$_2$Cl$_2$ (v/v)) 0.44; $^1$H-NMR (300 MHz, CD$_3$OD) δ: 7.31-7.23 (6H, m), 7.04-6.94 (6H, m), 4.71 (1H, d, J=1.9 Hz), 4.41 (1H, d, J=7.5 Hz), 4.12 (1H, dd, J=5.3, 10.9 Hz), 3.91-3.81 (3H, m), 3.66 (1H, d, J=5.6, 11.8 Hz), 3.57-3.47 (3H, m), 3.40-3.20 (7H, m), 3.07 (1H, t, J=5.9 Hz), 1.92-1.78 (4H, m), 0.87 (9H, s), 0.02 (3H, s), −0.18 (3H, s). $^{13}$C-NMR (75 MHz, CD$_3$OD) δ: 169.71, 160.66, 145.96, 142.43, 131.16, 131.05, 128.89, 128.80, 128.62, 120.00, 119.89, 116.83, 116.54, 116.41, 116.02, 115.74, 115.58, 104.65, 80.78, 80.43, 79.64, 78.16, 77.90, 75.13, 74.99, 71.43, 62.50, 62.08, 61.29, 38.96, 26.38, 25.75, 19.06, −4.40. MALDI-MS (C$_{43}$H$_{57}$F$_2$NO$_{13}$Si): [MNa]$^+$ 884.3668 (calcd. 884.3465).

This debenzylated C-glycoside (18.3 mg, 0.021 mmol) was dissolved in anhydrous THF (2.5 mL, teflon bottle) at 0° C., anhydrous pyridine (0.50 mL) followed by HF-pyridine complex (0.50 mL) were added and the solution was stirred for 17 h. NaHCO$_3$ (s) was added and the suspension was evaporated on celite and purified by dry column vacuum chromatography (4.6×2.0 cm) on silica gel eluting with a gradient of 0-20% MeOH in CH$_2$Cl$_2$ (v/v) to give the desired C-glycoside XVII (10.3 mg, 65%) as a white solid.

R$_f$ (20% MeOH in CH$_2$Cl$_2$ (v/v)) 0.31; $^1$H-NMR (300 MHz, CD$_3$OD) δ: 7.33-7.24 (6H, m), 7.05-6.94 (6H, m), 4.78 (1H, d, J=1.9 Hz), 4.60 (1H, t, J=4.4 Hz), 4.41 (1H, d, J=7.5 Hz), 4.30 (1H, d, J=10.0 Hz), 4.12 (1H, dd, J=5.0, 10.6 Hz), 3.91-3.84 (3H, m), 3.66 (1H, d, J=5.6, 11.8 Hz), 3.57-3.49 (3H, m), 3.40-3.20 (6H, m), 3.10-3.06 (1H, m), 1.97-1.82 (4H, m). $^{13}$C-NMR (75 MHz, CD$_3$OD) δ: 169.52, 164.87, 160.42, 142.07, 133.18 (C), 131.03, 130.87, 128.68, 128.59, 128.47, 123.36, 119.86, 119.74, 116.69, 116.38, 116.25, 116.22, 115.96, 115.88, 115.68, 104.54, 80.71, 80.36, 79.58, 78.11, 77.85, 74.94, 73.70, 71.38 (CH), 69.02, 62.47 (CH$_2$), 62.09 (CH$_2$+CH), 61.20 (CH), 37.54, 26.18 (CH$_2$). MALDI-MS (C$_{37}$H$_{43}$F$_2$NO$_{13}$): [MNa]$^+$ 770.2589 (calcd. 770.2600).

Example 14

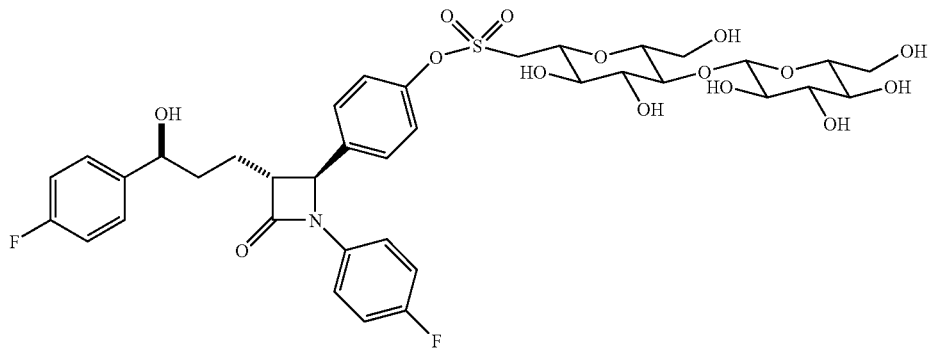

a)

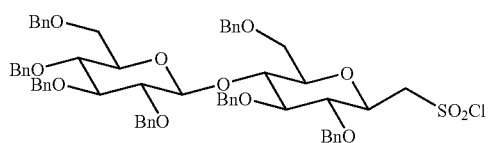

Alcohol XVIIa (prepared according to Spak, S. J.; Martin, O. R. *Tetrahedron* 2000, 56, 217-224; 895.3 mg, 0.907 mmol) was dissolved in anhydrous $CH_2Cl_2$ (10 mL), anhydrous pyridine (1.0 mL) followed by MsCl (0.20 mL, 2.6 mmol) were added and after stirring for 1 h, sat. aq. $NaHCO_3$ (40 mL) was added. The layers were separated and the aqueous layer extracted with EtOAc (3×20 mL). The combined organic layer was washed successively with sat. aq. $NaHCO_3$ (20 mL) and $H_2O$ (20 mL), evaporated on celite and purified by dry column vacuum chromatography (4.2×3.3 cm) on silica gel eluting with a gradient of 0-50% EtOAc in hexane (v/v) to give the corresponding mesylate (830.7 mg, 86%) as a white solid.

$R_f$ (1:1 EtOAc/hexane (v/v)) 0.67; $^1$H-NMR (300 MHz, $CDCl_3$) δ: 7.49-7.24 (35H, m), 5.31 (1H, d, J=11.2 Hz), 5.00 (1H, d, J=11.2 Hz), 4.98-4.79 (6H, m), 4.66-4.36 (9H, m), 4.09 (1H, t, J=9.3 Hz), 3.90 (1H, dd, J=2.8, 10.9 Hz), 3.83 (1H, d, J=10.0 Hz), 3.75-3.62 (5H, m), 3.55-3.39 (5H, m), 2.97 (3H, s). $^{13}$C-NMR (75 MHz, $CDCl_3$) δ: 138.97, 138.37, 138.21, 138.04, 137.61 (C), 128.37, 128.29, 128.18, 128.08, 127.93, 127.84, 127.76, 127.38, 127.34, 127.24, 102.51, 84.86, 82.64, 78.70, 77.94, 76.84, 76.53, 76.38, 75.57 (CH), 75.22, 75.09 ($CH_2$), 74.96, 74.78 ($CH_2$, CH), 73.21, 73.02, 69.22, 68.89, 67.76 ($CH_2$), 37.74 ($CH_3$). IR (cm$^{-1}$): 3063, 3030, 2867, 1497, 1454, 1358, 1277, 1209, 1174, 1150, 1092, 1071, 1028, 984, 922, 812, 737, 698, 527. MALDI-MS ($C_{63}H_{68}O_{13}S$): [MNa]$^+$ 1087.4284 (calcd. 1087.4278). Anal. Calcd for $C_{63}H_{68}O_{13}S$: C, 71.03; H, 6.43. Found: C, 70.94; H, 6.62.

Subsequently, this mesylate (825 mg, 0.774 mmol) was dissolved in EtOH (20 mL), KOSCMe (278 mg, 2.43 mmol), iPrOH (10 mL) and THF (10 mL) were added and the orange solution was stirred at reflux for 3 h (orange precipitate). Additional KOSCMe (512 mg, 4.48 mmol) was added and the suspension was stirred at reflux for 16 h. After cooling, 50% sat. aq. $NaHCO_3$ (100 mL) was added and the suspension was extracted with ether (4×30 mL). The combined organic layer was washed successively with sat. aq. Na—$HCO_3$ (50 mL) and $H_2O$ (50 mL), evaporated on celite and purified by dry column vacuum chromatography (4.2×3.3 cm) on silica gel eluting with a gradient of 0-50% EtOAc in hexane (v/v) to give the corresponding thioacetate (637 mg, 79%) as a light orange solid.

$R_f$ (1:3 EtOAc/hexane (v/v)) 0.45; $^1$H-NMR (300 MHz, $CDCl_3$) δ: 7.43-7.19 (35H, m), 5.22 (1H, d, J=11.2 Hz), 4.92 (1H, d, J=11.2 Hz), 4.88 (1H, d, J=11.2 Hz), 4.87-4.71 (5H, m), 4.62 (1H, d, J=12.5 Hz), 4.60-4.43 (5H, m), 4.41 (1H, d, J=11.8 Hz), 4.06 (1H, t, J=9.3 Hz), 3.86 (1H, dd, J=3.7, 11.2 Hz), 3.75 (1H, dd, J=1.6, 10.9 Hz), 3.69-3.55 (5H, m), 3.51-3.31 (6H, m), 3.05 (1H, dd, J=6.8, 13.7 Hz), 2.34 (3H, s). $^{13}$C-NMR (75 MHz, $CDCl_3$) δ: 195.04, 139.19, 138.53, 138.30, 138.24, 138.17, 137.96 (C), 128.33, 128.26, 128.20, 128.04, 127.79, 127.71, 127.63, 127.55, 127.47, 127.29, 127.19, 102.40, 85.12, 84.88, 82.71, 79.85, 79.30, 78.05, 77.87 (CH), 75.62, 75.18 ($CH_2$), 75.09 (CH), 74.94, 74.81, 73.26, 73.21, 68.96, 67.86, 31.12 ($CH_2$), 30.49 ($CH_3$). IR (cm$^{-1}$): 3030, 2868, 1692, 1496, 1454, 1358, 1210, 1067, 1028, 773, 735, 698, 626. MALDI-MS ($C_{64}H_{68}O_{11}S$): [MNa]$^+$ 1067.4365 (calcd. 1067.4380). Anal. Calcd for $C_{64}H_{68}O_{11}S$: C, 73.54; H, 6.56. Found: C, 73.50; H, 6.60.

The thioacetate received above (631 mg, 0.604 mmol) was suspended in AcOH (10 mL), KOAc (933 mg, 9.5 mmol) followed by Oxone ($2KHSO_5.KHSO_4.K_2SO_4$, 1.179 g, 2.55 mmol) were added and after stirring for 18 h, sat. aq. $Na_2CO_3$ (50 mL) and $H_2O$ (50 mL) were carefully added. After extraction with $CHCl_3$ (4×25 mL), the combined organic layer was washed with sat. aq. $Na_2CO_3$ (25 mL), evaporated on celite and purified by dry column vacuum chromatography (4.1× 3.3 cm) on silica gel eluting with a gradient of 0-20% MeOH in $CH_2Cl_2$ (v/v) to give the corresponding sulfinate salt (622 mg, 96%) as a colourless oil.

$R_f$ (10% MeOH in $CH_2Cl_2$ (v/v)) 0.29; $^1$H-NMR (300 MHz, $CDCl_3$) δ: 7.40-7.14 (35H, m), 5.19-4.34 (15H, m), 4.17-3.22 (15H, m). $^{13}$C-NMR (75 MHz, $CDCl_3$) δ: 138.97, 138.32, 138.21, 138.06, 137.88, 137.84, 128.70, 128.36, 128.18, 128.05, 127.86, 127.76, 127.63, 127.57, 127.44, 127.29, 127.20, 126.94, 84.53, 84.45, 82.01, 79.48, 77.96, 77.75, 76.06, 76.01, 75.46, 74.94, 74.79, 74.67, 74.57, 73.28, 73.08, 73.02, 53.42. IR (cm$^{-1}$): 3478, 3063, 3030, 2870, 1497, 1454, 1361, 1315, 1210, 1174, 1069, 1048, 1028, 736, 698, 621. MALDI-MS ($C_{62}H_{65}NaO_{13}S$): [MH]$^+$ 1073.4098 (calcd. 1073.4122); [MNa]+1095.3926 (calcd. 1095.3941).

Finally, the obtained sulfinate salt (334 mg, 0.311 mmol) was dissolved in anhydrous acetonitrile/CH$_2$Cl$_2$ (4 mL, 1:1 (v/v)) at 0° C., Ph$_3$P (264 mg, 1.01 mmol) and thionyl chloride (0.10 mL, 1.37 mmol) were added sequentially at 0° C. and the suspension was stirred at room temperature for 6 h. EtOAc/hexane (1:4 (v/v), 30 mL) was added, the suspension was filtered through a short pad of silica gel (4×5 mL EtOAc/hexane (1:3 (v/v)) washings) and the filtrate was evaporated and dried shortly under vacuum to give the desired sulfonyl chloride XVIIa (220 mg, 66%) as a light yellow foam.

$R_f$ (1:3 EtOAc/hexane (v/v)) 0.38; $^1$H-NMR (300 MHz, CDCl$_3$) δ: 7.50-7.26 (35H, m), 5.30 (1H, d, J=11.2 Hz), 4.98 (1H, d, J=10.6 Hz), 4.96-4.81 (5H, m), 4.79 (1H, d, J=10.6 Hz), 4.67-4.50 (6H, m), 4.48 (1H, d, J=11.8 Hz), 4.23-4.15 (1H, m), 3.98-3.91 (2H, m), 3.85-3.57 (8H, m), 3.51-3.38 (3H, m), 3.30 (1H, t J=9.0 Hz). $^{13}$C-NMR (75 MHz, CDCl$_3$) δ: 138.77, 138.45, 138.17, 138.11, 137.78, 137.27 (C), 128.63, 128.38, 128.31, 128.18, 128.12, 127.94, 127.78, 127.70, 127.63, 127.55, 127.42, 127.29, 102.32, 84.98, 84.80, 82.66, 79.23, 77.95, 77.82, 75.78 (CH), 75.60, 75.38 (CH$_2$), 75.12 (CH), 74.99, 74.78, 74.70 (CH$_2$), 74.21 (CH), 73.24, 68.95, 67.35, 66.79 (CH$_2$). IR (cm$^{-1}$): 3089, 3063, 3030, 2868, 1496, 1454, 1362, 1313, 1280, 1209, 1167, 1091, 1067, 1028, 913, 771, 736, 698, 601. MALDI-MS ($C_{62}H_{65}ClO_{12}S$): [MNa]$^+$ 1091.3767 (calcd. 1091.3783).

The sulfonyl chloride XVIIIa (271 mg, 0.253 mmol) was dissolved in anhydrous CH$_2$Cl$_2$ (3 mL), anhydrous pyridine (0.5 mL) followed by the silylated azetidinone phenol VIa obtained in step 2a) (75.7 mg, 0.145 mmol) were added and the solution was stirred for 38 h, diluted with EtOAc (50 mL) and washed sequentially with sat. aq. NaHCO$_3$ (15 mL) and H$_2$O (15 mL). The organic layer was evaporated on celite and purified by dry column vacuum chromatography (4.5×3.3 cm) on silica gel eluting with a gradient of 0-20% EtOAc in toluene (v/v) to give the corresponding sulfonate mixed with unreacted phenol VIa (166 mg, 4:1 mixture) as a white foam.

$R_f$ (1:1 EtOAc/hexane (v/v)) 0.73; $^1$H-NMR (300 MHz, CDCl$_3$) δ: 7.49-7.17 (41H, m), 7.06 (2H, d, J=8.7 Hz), 7.02 (2H, t, J=8.1 Hz), 6.96 (2H, d, J=8.7 Hz), 5.31 (1H, d, J=11.2 Hz), 5.01-4.74 (7H, m), 4.65-4.45 (8H, m), 4.21 (1H, t, J=9.3 Hz), 4.02-3.96 (2H, m), 3.86-3.60 (6H, m), 3.53-3.47 (4H, m), 3.33 (1H, d, J=9.3 Hz), 3.26 (1H, t, J=9.0 Hz), 3.19 (1H, m), 3.06-3.00 (1H, m), 2.06-1.84 (4H, m), 0.96 (9H, s), 0.10 (3H, s), −0.07 (3H, s). $^{13}$C-NMR (75 MHz, CDCl$_3$) δ: 166.70, 160.35, 160.00, 156.27, 149.33, 140.35, 140.31, 138.63, 138.26, 138.00, 137.90, 137.59, 137.45, 137.29, 136.51, 133.47 (C), 128.82, 128.73, 128.34, 128.19, 128.08, 127.98, 127.85, 127.66, 127.56, 127.45, 127.30, 127.25, 127.12, 127.01, 125.10, 123.32, 118.11, 118.01, 115.91, 115.60, 115.00, 114.93, 114.72, 102.39, 84.93, 84.80, 82.56, 78.82, 78.55, 77.95, 75.99 (CH), 75.60, 75.31 (CH$_2$), 75.15 (CH), 74.96, 74.76 (CH$_2$), 74.23, 73.77 (CH), 73.21, 73.08, 68.97, 67.62 (CH$_2$), 61.02, 60.57, 60.39 (CH), 51.26, 38.02 (CH$_2$), 25.85 (CH$_3$), 24.67 (CH$_2$), 18.19 (C), −4.56, −4.87 (CH$_3$). $^{19}$F-NMR (282 MHz, CDCl$_3$) δ: −114.94 (1F, septet, J=4.3 Hz), −117.10 (1F, septet, J=4.3 Hz). MALDI-MS ($C_{92}H_{99}F_2NO_{15}SiS$): [MNa]$^+$ 1578.6365 (calcd. 1578.6370).

Subsequently, this sulfonate (166 mg 4:1 mixture) was dissolved in EtOH (5 mL), Pd(OH)$_2$/C (20% (w/w), 94 mg) was added and the suspension was evacuated 4 times with H$_2$ and stirred under an H$_2$-atmosphere for 11.5 h. The suspension was evaporated on celite and purified by dry column vacuum chromatography (4.3×2.0 cm) on silica gel eluting with a gradient of 0-10% MeOH in CH$_2$Cl$_2$ (v/v) to give the corresponding debenzylated β-lactam (69.5 mg, 52% from phenol VIa) as a colourless oil.

$R_f$ (20% MeOH in CH$_2$Cl$_2$ (v/v)) 0.46; $^1$H-NMR (300 MHz, CD$_3$OD) δ: 7.46-7.38 (4H, m), 7.31-7.23 (4H, m), 7.04-6.95 (4H, m), 4.75-4.68 (1H, m), 4.44 (1H, d, J=8.1 Hz), 3.92-3.80 (5H, m), 3.69-3.18 (11H, m), 3.10-3.05 (1H, m), 1.95-1.75 (4H, m), 0.86 (9H, s), 0.01 (3H, s), −0.19 (3H, s). $^{13}$C-NMR (75 MHz, CD$_3$OD) δ: 169.31, 169.21, 161.76, 158.91, 150.96, 142.28, 138.45, 135.01, 134.98, 131.06, 130.95 (C), 128.83, 124.50, 119.92, 119.83, 116.99, 116.68, 116.10, 116.04, 115.81, 115.74, 104.54, 80.33, 80.10, 78.11, 77.81, 77.72, 76.30, 75.13, 74.89, 73.61, 71.38 (CH), 62.47, 61.63 (CH$_2$), 61.56, 61.47 (CH), 53.26, 38.83 (CH$_2$), 26.38 (CH$_3$), 25.75 (CH$_2$), 19.04 (C), −4.40, −4.70 (CH$_3$). $^{19}$F-NMR (282 MHz, CD$_3$OD) δ: −117.94 (1F, septet, J=4.3 Hz), −120.10 (1F, septet, J=4.3 Hz). MALDI-MS ($C_{43}H_{57}F_2NO_{15}SiS$): [MNa]$^+$ 948.3088 (calcd. 948.3084).

This debenzylated β-Lactam (59.5 mg, 0.073 mmol) was dissolved in anhydrous THF (2.0 mL, teflon bottle), anhydrous pyridine (0.40 mL) followed by HF-pyridine complex (0.40 mL) were added and the solution was stirred for 14 h. Sat. aq. NaHCO$_3$ (5 mL) was added and the suspension was evaporated on celite and purified by dry column vacuum chromatography (4.4×2.0 cm) on silica gel eluting with a gradient of 10-20% MeOH in CH$_2$Cl$_2$ (v/v) to give the desired β-lactam XVIII (38.1 mg, 64%) as a white solid.

$R_f$ (10% MeOH in CH$_2$Cl$_2$ (v/v)) 0.17 (eluted thrice); $^1$H-NMR (300 MHz, CD$_3$OD) δ: 7.45 (2H, t, J=9.3 Hz), 7.40 (2H, d, J=8.7 Hz), 7.33-7.24 (4H, m), 7.02 (2H, t, J=8.1 Hz), 6.98 (2H, d, J=8.7 Hz), 4.90 (1H, d, J=1.9 Hz), 4.60 (1H, dd, J=5.0, 6.2 Hz), 4.43 (1H, d, J=7.5 Hz), 3.92-3.79 (5H, m), 3.69-3.49 (4H, m), 3.44-3.18 (6H, m), 3.12-3.06 (1H, m), 1.99-1.82 (4H, m). $^{13}$C-NMR (75 MHz, CD$_3$OD) δ: 169.31, 165.08, 162.17, 161.85, 158.96, 150.98, 142.15, 138.51, 135.01 (C), 128.88, 128.76, 124.46, 119.97, 119.86, 116.99, 116.68, 116.13, 115.84, 104.54, 80.35, 80.06, 78.11, 77.81, 77.71, 76.31, 74.91, 73.77, 73.63, 71.39 (CH), 62.45, 61.50 (CH$_2$), 61.42 (CH), 53.26, 37.45, 26.12 (CH$_2$). $^{19}$F-NMR (282 MHz, CD$_3$OD) δ: −118.08 (1F, septet, J=4.3 Hz), −120.21 (1F, septet, J=4.3 Hz). MALDI-MS ($C_{37}H_{43}F_2NO_{15}S$): [MNa]$^+$ 834.2223 (calcd. 834.2219).

Example 15

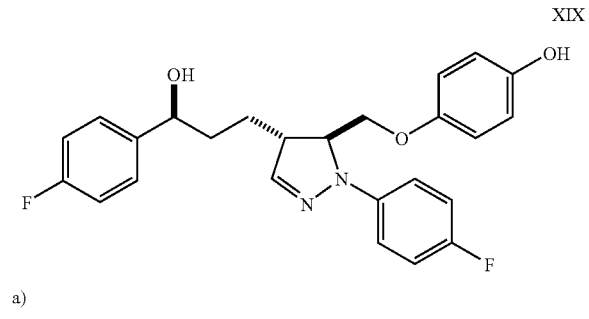

XIX a)

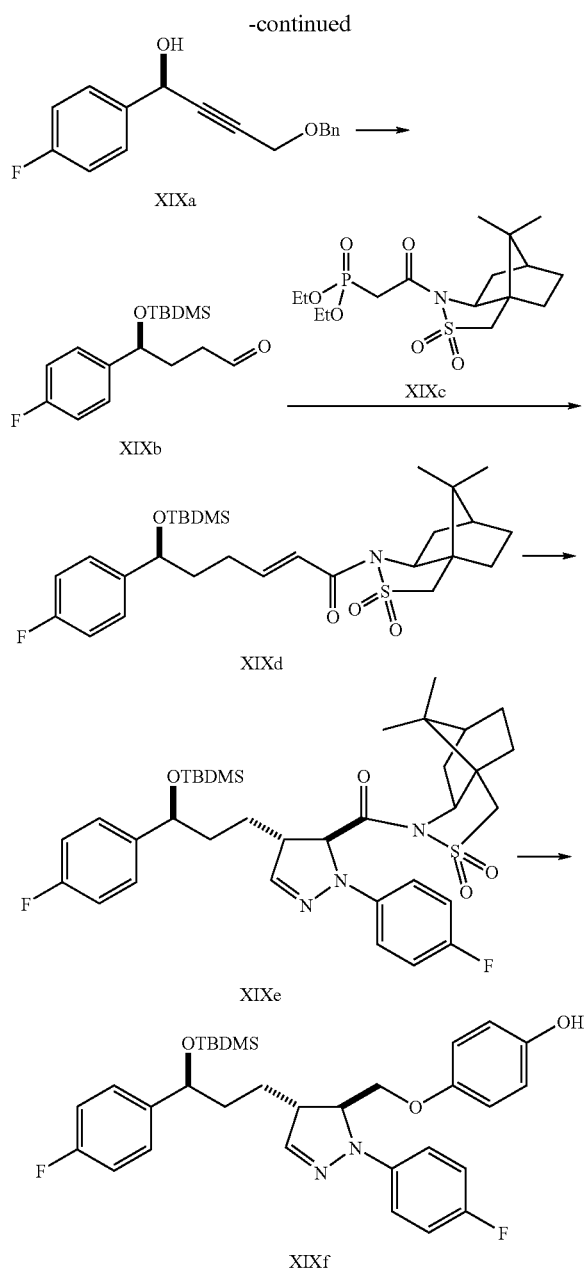

A 50 mL Schlenk flask was charged with Zn(OTf)$_2$ (12.647 g, 34.79 mmol) and heated to 120° C. under high-vacuum (0.2 Torr) for 3.5 h. After cooling, (+)-N-methylephedrine (6.595 g, 36.79 mmol) was added and the flask was purged with Ar for 15 min. Anhydrous toluene (14 mL) followed by Et$_3$N (3.874 g, 38.3 mmol) were added and after 3 h stirring, benzyl propargyl ether (prepared according to Ren, X. F.; Turos, E.; Lake, C. H.; Churchill, M. R. *J. Org. Chem.* 1995, 60, 6468-6483; 5.556 g, 38.00 mmol) was added in one portion. After 20 min stirring, the mixture was transferred to a precooled acetone bath (8° C.), stirred for 5 min and p-FC$_6$H$_4$CHO (3.632 g, 29.26 mmol) was added in one portion. After 15 h stirring at 9 to 12° C., the suspension was diluted with EtOAc (125 mL) and washed with sat. aq. NH$_4$Cl (2×30 mL) and brine (30 mL). The organic layer was evaporated on celite and purified by dry column vacuum chromatography (5.4×5.5 cm) on silica gel eluting with a gradient of 0-50% EtOAc in hexane (v/v) to give propargyl alcohol XIXa (5.896 g, 75%) as a light yellow oil.

Enantiomeric excess as determined by HPLC analysis: 96% ee; R$_t$ 20 min (R-XIXa), 28 min (S-XIXa) (Chiracel OD-H 25 cm, 6% iPrOH in hexane, flow 1.0 mL/min, 254 nm). R$_f$ (1:3 EtOAc/hexane (v/v)) 0.28; $^1$H-NMR (300 MHz, CDCl$_3$) δ: 7.50 (2H, dd, J=5.6, 8.7 Hz), 7.38-7.32 (5H, m), 7.06 (2H, t, J=8.7 Hz), 5.48 (1H, s), 4.60 (2H, s), 4.26 (2H, s), 2.84 (1H, s). $^{13}$C-NMR (75 MHz, CDCl$_3$) δ: 164.01, 160.75, 136.95, 136.04 (C), 128.30, 128.21, 127.92, 127.81, 115.43, 115.13 (CH), 86.13, 82.62 (C), 71.74 (CH$_2$), 63.74 (CH), 57.35 (CH$_2$). $^{19}$F-NMR (282 MHz, CDCl$_3$) δ: −113.28 (1F, septet, J=4.3 Hz). IR (cm$^{-1}$): 3390, 3066, 3032, 2859, 1604, 1508, 1455, 1413, 1386, 1355, 1224, 1158, 1121, 1096, 1072, 1028, 1014, 842, 772, 744, 699, 592, 561, 498. MALDI-MS (C$_{17}$H$_{15}$FO$_2$): [MNa]$^+$ 293.0947 (calcd. 293.0954). Anal. Calcd for C$_{17}$H$_{15}$FO$_2$: C, 75.54; H, 5.59. Found: C, 75.39; H, 5.62.

Subsequently this propargyl alcohol (4.108 g, 15.20 mmol) was dissolved in anhydrous DMF (50 mL), imidazole (2.123 g, 31.1 mmol) and TBDMSCl (3.590 mg, 23.8 mmol) were added sequentially and the solution was stirred for 3.5 h followed by addition of 50% sat. aq. NaHCO$_3$ (150 mL). After extraction with ether (4×50 mL), the combined organic layer was washed successively with sat. aq. NaHCO$_3$ (50 mL) and H$_2$O (50 mL), evaporated and dried shortly under high vacuum. The residue was dissolved in EtOH (40 mL), Na$_2$CO$_3$ (3.229 g, 30.5 mmol) and Pd/C (10% (w/w), 223 mg) were added and the suspension was evacuated 4 times with H$_2$ and stirred under an H$_2$-atmosphere for 19 h. The suspension was diluted with 10% EtOAc/hexane (250 mL (v/v)) and filtered through a short plug of silica gel (2×25 mL 20% EtOAc/hexane washings (v/v)), evaporated and dried shortly under high vacuum. The residue was dissolved in EtOH (40 mL), Pd/C (10% (w/w), 142 mg) was added and the suspension was evacuated 4 times with H$_2$ and stirred under an H$_2$-atmosphere for 1 h. Additional Pd/C (10% (w/w), 190 mg) was added and the suspension was evacuated 4 times with H$_2$ and stirred under an H$_2$-atmosphere for 1.25 h. The suspension was evaporated on celite and purified by dry column vacuum chromatography (5.2×5.5 cm) on silica gel eluting with a gradient of 0-25% EtOAc in hexane (v/v) to give the corresponding alcohol (3.643 g, 80%) as a light yellow oil.

R$_f$ (1:3 EtOAc/hexane (v/v)) 0.37; $^1$H-NMR (300 MHz, CDCl$_3$) δ: 7.24 (2H, dd, J=5.6, 8.7 Hz), 6.97 (2H, t, J=8.7 Hz), 4.69 (1H, dt, J=1.2, 5.0 Hz), 3.59 (2H, dt, J=1.2, 6.2 Hz), 2.18 (1H, bs), 1.77-1.45 (4H, m), 0.87 (9H, s), 0.02 (3H, s), −0.15 (3H, S). $^{13}$C-NMR (75 MHz, CDCl$_3$) δ: 163.37, 160.13, 140.96, 140.91 (C), 127.32, 127.23, 114.94, 114.64, 74.16 (CH), 62.76, 37.19, 28.47 (CH$_2$), 25.76 (CH$_3$), 18.15 (C), −4.71, −5.05 (CH$_3$). IR (cm$^{-1}$): 3339, 2954, 2930, 2885, 2858, 1606, 1510, 1472, 1463, 1362, 1252, 1223, 1156, 1092, 1060, 984, 890, 836, 776, 668, 560. MALDI-MS (C$_{16}$H$_{27}$FO$_2$Si): [MNa]$^+$ 321.1643 (calcd. 321.1662). Anal. Calcd for C$_{16}$H$_{27}$FO$_2$Si: C, 64.39; H, 9.12. Found: C, 64.36; H, 9.15.

The alcohol obtained above was dissolved in CH$_2$Cl$_2$ (50 mL), Dess-Martin periodinane (5.658 g, 13.3 mmol) was added and the milky solution was stirred at room temperature for 1.5 h. Sat. aq. Na$_2$SO$_3$ (100 mL) was added and the layers were swirled until the solid had dissolved. The layers were separated and the aqueous phase was extracted with CH$_2$Cl$_2$ (2×40 mL). The combined organic phase was evaporated on celite and purified by dry column vacuum chromatography (5.1×5.5 cm) on silica gel eluting with a gradient of 0-10%

EtOAc in hexane (v/v) to give the corresponding aldehyde XIXb (2.093 g, 80%) as a light yellow oil.

$R_f$ (1:3 EtOAc/hexane (v/v)) 0.63; $^1$H-NMR (300 MHz, CDCl$_3$) δ: 9.73 (1H, d, J=1.5 Hz), 7.25 (2H, dd, J=5.6, 8.7 Hz), 6.99 (2H, t, J=9.0 Hz), 4.74 (1H, dt, J=5.0, 6.8 Hz), 2.52-2.35 (2H, m), 2.06-1.88 (2H, m), 0.88 (9H, s), 0.02 (3H, s), −0.16 (3H, s). $^{13}$C-NMR (75 MHz, CDCl$_3$) δ: 201.91 (CH), 163.35, 160.10, 140.13 (C), 127.20, 127.10, 115.04, 114.75, 73.03 (CH), 39.69, 33.11 (CH$_2$), 25.85 (CH$_3$), 18.21 (C), −4.61, −4.95 (CH$_3$). IR (cm$^{-1}$): 2955, 2938, 2888, 2858, 2720, 1727, 1606, 1509, 1472, 1464, 1412, 1390, 1362, 1254, 1223, 1156, 1090, 1014, 837, 776, 670, 540. Anal. Calcd for C$_{16}$H$_{25}$FO$_2$Si: C, 64.82; H, 8.50. Found: C, 64.95; H, 8.36.

LiCl (140.8 mg, 3.32 mmol) was heated shortly with a heat gun under high-vacuum and after cooling, anhydrous CH$_3$CN (5 mL), phosphonate XIXc (prepared according to Melekhov, A.; Fallis, A. G. *Tetrahedron Lett.* 1999, 40, 7867-7870; 660 mg, 1.68 mmol) and DBU (221 mg, 1.45 mmol) were added sequentially. After 3 min stirring, the aldehyde XIXb (407.3 mg, 1.3.7 mmol) was added and the suspension was stirred at room temperature for 2.5 h followed by addition of 50% sat. aq. NaHCO$_3$ (60 mL). After extraction with ether/hexane (1:1 (v/v), 4×25 mL), the combined organic layer was washed with brine (25 mL), evaporated on celite and purified by dry column vacuum chromatography (4.6×3.3 cm) on silica gel eluting with a gradient of 0-20% EtOAc in hexane (v/v) to give olefin XIXd (520.7 mg, 71%) as a colourless oil.

$R_f$ (1:3 EtOAc/hexane (v/v)) 0.43; $^1$H-NMR (300 MHz, CDCl$_3$) δ: 7.25 (2H, dd, J=5.6, 8.7 Hz), 7.10-6.94 (3H, m), 6.53 (1H, d, J=14.9 Hz), 4.65 (1H, dd, J=5.0, 7.5 Hz), 3.91 (1H, dd, J=5.6, 6.8 Hz), 3.50 (1H, d, J=13.7 Hz), 3.42 (1H, d, J=13.7 Hz), 2.30-2.23 (2H, m), 2.09-2.02 (2H, m), 1.90-1.70 (5H, m), 1.43-1.30 (2H, m), 1.15 (3H, s), 0.95 (3H, s), 0.85 (9H, s), 0.01 (3H, s), −0.20 (3H, s). $^{13}$C-NMR (75 MHz, CDCl$_3$) δ: 163.88, 163.39, 160.14, 150.06, 140.63 (C), 127.35, 127.26, 120.91, 114.98, 114.69, 73.24, 64.99 (CH), 53.04 (CH$_2$), 48.33, 47.67 (C), 44.58 (CH), 38.61, 38.39, 32.71, 28.32, 26.40 (CH$_2$), 25.72, 20.72, 19.78 (CH$_3$), 18.04 (C), −4.74, −5.10 (CH$_3$). IR (cm$^{-1}$): 2956, 2885, 2859, 1684, 1640, 1605, 1509, 1472, 1414, 1374, 1332, 1295, 1250, 1220, 1165, 1134, 1083, 1049, 995, 970, 860, 836, 774, 544. MALDI-MS (C$_{28}$H$_{42}$FNO$_4$SSi): [MNa]$^+$ 558.2479 (calcd. 558.2486). Anal. Calcd for C$_{28}$H$_{42}$FNO$_4$SSi: C, 62.77; H, 7.90; N, 2.61. Found: C, 62.84; H, 7.78; N, 2.58.

Olefin XIXd was dissolved in anhydrous toluene (2.0 mL), TMSCHN$_2$ (2 M in hexanes, 1.50 mL, 3.0 mmol) was added and the solution was stirred at room temperature for 64 h. After evaporation, the residue was dissolved in CH$_2$Cl$_2$ (10 mL), TFA (202 mg, 1.77 mmol) was added and the solution was stirred for 20 min. Sat. aq. Na—HCO$_3$ (1.5 mL) was added and the mixture was evaporated on celite and purified by dry column vacuum chromatography (4.5×3.3 cm) on silica gel eluting with a gradient of 0-40% EtOAc in hexane (v/v) to give the corresponding pyrazoline (468 mg, 84%) as a light yellow foam.

$R_f$ (1:3 EtOAc/hexane (v/v)) 0.25; $^1$H-NMR (300 MHz, CDCl$_3$) δ: 7.21 (2H, dd, J=5.6, 8.7 Hz), 6.95 (2H, t, J=8.7 Hz), 6.60 (1H, s), 6.16 (1H, d, J=5.6 Hz), 4.65 (1H, t, J=5.0 Hz), 4.33 (1H, dd, J=5.9, 9.7 Hz), 3.87 (1H, dd, J=5.0, 7.5 Hz), 3.67-3.62 (1H, bs), 3.53 (1H, d, J=13.7 Hz), 3.44 (1H, d, J=13.7 Hz), 2.15-1.99 (2H, m), 1.91-1.86 (3H, m), 1.66-1.51 (3H, m), 1.47-1.21 (3H, m), 1.14 (3H, s), 0.95 (3H, s), 0.86 (9H, s), 0.01 (3H, s), −0.17 (3H, s). $^{13}$C-NMR (75 MHz, CDCl$_3$) δ: 167.96, 163.12, 159.89 (C), 146.91 (CH), 140.52, 140.49 (C), 127.15, 127.05, 114.83, 114.54, 73.37, 66.44, 65.09 (CH), 52.81 (CH$_2$), 48.91 (C), 48.04 (CH), 47.79 (C), 44.33 (CH), 37.98, 37.79, 32.55, 26.76, 26.45 (CH$_2$), 25.82, 20.68, 19.84 (CH$_3$), 18.16 (C), −4.64, −4.90 (CH$_3$). IR (cm$^{-1}$): 3360, 2955, 2857, 1700, 1604, 1509, 1472, 1390, 1329, 1273, 1250, 1236, 1221, 1166, 1134, 1086, 1066, 994, 939, 836, 775, 694, 542. MALDI-MS (C$_{29}$H$_{44}$FN$_3$O$_4$SSi): [MNa]$^+$ 600.2691 (calcd. 600.2704). Anal. Calcd for C$_{29}$H$_{44}$FN$_3$O$_4$SSi: C, 60.28; H, 7.67; N, 7.27. Found: C, 60.25; H, 7.83; N, 7.16.

This pyrazoline (409.8 mg, 0.709 mmol), Cu(OAc)$_2$ (296 mg, 1.63 mmol) and (p-FC$_6$H$_4$)$_3$Bi (prepared according to Banfi, A.; Bartoletti, M.; Bellora, E.; Bignotti, M.; Turconi, M. *Synthesis* 1994, 775-776; 950 mg, 1.92 mmol) were dissolved in anhydrous CH$_2$Cl$_2$ (5 mL), anhydrous Et$_3$N (165 mg, 1.63 mmol) was added and the dark green suspension was stirred at room temperature for 12.5 h. After evaporation on celite the residue was purified by dry column vacuum chromatography (4.5×3.3 cm) on silica gel eluting with a gradient of 0-30% EtOAc in hexane (v/v) to give N-arylated pyrazoline XIXe (320.8 mg, 63%) as a light yellow foam.

$R_f$ (1:3 EtOAc/hexane (v/v)) 0.33; $^1$H-NMR (300 MHz, CDCl$_3$) δ: 7.24 (2H, dd, J=5.3, 8.4 Hz), 7.01-6.94 (4H, m), 6.89 (2H, t, J=8.7 Hz), 6.68 (1H, d, J=1.9 Hz), 5.05 (1H, d, J=3.7 Hz), 4.62 (1H, t, J=5.3 Hz), 3.85 (1H, dd, J=4.4, 7.5 Hz), 3.59 (1H, d, J=14.3 Hz), 3.58 (1H, d, J=14.3 Hz), 3.41-3.35 (1H, m), 1.98-1.78 (5H, m), 1.72-1.60 (3H, m), 1.41-1.23 (3H, m), 1.21 (3H, s), 0.98 (3H, s), 0.88 (9H, s), 0.04 (3H, s), −0.17 (3H, s). $^{13}$C-NMR (75 MHz, CDCl$_3$) δ: 169.54, 163.38, 160.14, 158.46, 155.30 (C), 142.10 (CH), 140.75 (C), 127.32, 127.22, 115.71, 115.40, 114.96, 114.67, 114.22, 114.12, 73.99, 65.48, 64.93 (CH), 53.02 (CH, CH$_2$), 49.05, 47.77 (C), 44.31 (CH), 37.98, 36.95, 32.76, 27.79, 26.25 (CH$_2$), 25.75, 20.37, 19.77 (CH$_3$), 18.07 (C), −4.77, −5.01 (CH$_3$). $^{19}$F (282 MHz, CDCl$_3$) δ: −116.27 (1F, m), −125.73 (1F, septet, J=4.3 Hz). IR (cm$^{-1}$): 2957, 2857, 1699, 1606, 1510, 1471, 1413, 1362, 1334, 1268, 1250, 1221, 1166, 1136, 1113, 1088, 1063, 987, 836, 776, 759, 538. MALDI-MS (C$_{35}$H$_{47}$F$_2$N$_3$O$_4$SSi): [MH-TBDMSOH]$^+$ 540.2127 (calcd. 540.2132); [MNa]$^+$ 694.2909 (calcd. 694.2922). Anal. Calcd for C$_{35}$H$_{47}$F$_2$N$_3$O$_4$SSi: C, 62.56; H, 7.05; N, 6.25. Found: C, 62.37; H, 7.05; N, 6.03.

The N-arylated pyrazoline XIXe (101.5 mg, 0.151 mmol) was dissolved in anhydrous THF (5 mL) −78° C., LiAlH$_4$ (33 mg, 0.87 mmol) was added and the suspension was stirred at −78° C. for 4.5 h. Sat. aq. NaHCO$_3$ (1 mL) was added and the mixture was evaporated on celite and purified twice by dry column vacuum chromatography (4.6×2.0 cm) on silica gel eluting with a gradient of 0-30% EtOAc in hexane (v/v) to give the corresponding alcohol (52.7 mg, 76%) as a light yellow oil.

$R_f$ (1:3 EtOAc/hexane (v/v)) 0.23; $^1$H-NMR (300 MHz, CDCl$_3$) δ: 7.23 (2H, dd, J=5.6, 8.7 Hz), 7.04-6.92 (6H, m), 6.67 (1H, d, J=1.2 Hz), 4.64 (1H, t, J=5.9 Hz), 3.81 (1H, dd, J=4.0, 11.5 Hz), 3.68-3.58 (2H, m), 3.12 (1H, dd, J=6.2, 6.8 Hz), 1.86 (1H, bs), 1.77-1.67 (2H, m), 1.58-1.48 (2H, m), 0.86 (9H, s), 0.00 (3H, s), −0.17 (3H, s). $^{13}$C-NMR (75 MHz, CDCl$_3$) δ: 163.47, 160.22, 158.83, 155.68 (C), 144.84 (CH), 142.35, 140.67, 140.62 (C), 127.26, 127.16, 115.75, 115.46, 115.11, 115.06, 114.96, 114.83, 73.76, 66.81 (CH), 62.37 (CH$_2$), 50.05 (CH), 37.72, 28.28 (CH$_2$), 25.75 (CH$_3$), 18.12 (C), −4.67, −5.01 (CH$_3$). $^{19}$F (282 MHz, CDCl$_3$) δ: −115.25 (1F, septet, J=4.3 Hz), −124.25 (1F, septet, J=4.3 Hz). IR (cm$^{-1}$): 3401, 2953, 2930, 2885, 2858, 1672, 1605, 1509, 1472, 1463, 1416, 1362, 1296, 1252, 1223, 1156, 1086, 1006, 979, 938, 861, 835, 776, 666, 608, 554. MALDI-MS (C$_{25}$H$_{34}$F$_2$N$_2$O$_2$Si): [MH-CH$_2$O] 429.2175 (calcd. 429.2174); [M−H]$^+$ 459.2279 (calcd. 459.2279).

Subsequently this alcohol (70.8 mg, 0.154 mmol) was dissolved in anhydrous CH$_2$Cl$_2$ (5 mL), anhydrous Et$_3$N (0.50 mL, 3.9 mmol), DMAP (6.8 mg, 0.056 mmol) and TsCl (69 mg, 0.36 mmol) were added and the solution was stirred at room temperature for 12.5 h, evaporated on celite and purified by dry column vacuum chromatography (4.4×2.0 cm) on silica gel eluting with a gradient of 0-20% EtOAc in hexane (v/v) to give the corresponding tosylate (78.4 mg, 83%) as a colourless oil.

$R_f$ (1:3 EtOAc/hexane (v/v)) 0.44; $^1$H-NMR (300 MHz, CDCl$_3$) δ: 7.68 (2H, d, J=8.7 Hz), 7.25 (4H, t, J=8.1 Hz), 6.99 (2H, t, J=8.7 Hz), 6.92-6.80 (4H, m), 6.64 (1H, d, J=1.2 Hz), 4.65 (1H, dd, J=4.4, 6.8 Hz), 4.12 (1H, dd, J=2.5, 9.3 Hz), 3.92-3.81 (2H, m), 3.08-3.01 (1H, m), 2.42 (3H, s), 1.80-1.43 (4H, m), 0.87 (9H, s), 0.01 (3H, s), −0.17 (3H, s). $^{13}$C-NMR (75 MHz, CDCl$_3$) δ: 163.49, 160.24, 158.59, 155.43, 145.16 (C), 143.40 (CH), 140.54, 132.21 (C), 129.84, 127.82, 127.32, 127.21, 115.79, 115.48, 115.12, 114.83, 114.31, 114.22, 73.50 (CH), 67.45 (CH$_2$), 62.42, 50.74 (CH), 37.35, 27.87 (CH$_2$), 25.77, 21.59 (CH$_3$), 18.10 (C), −4.67, −5.01 (CH$_3$). $^{19}$F (282 MHz, CDCl$_3$) δ: −116.01 (1F, m), −125.40 (1F, septet, J=4.3 Hz). IR (cm$^{-1}$): 3055, 3034, 2953, 2930, 2886, 2857, 1603, 1509, 1472, 1463, 1365, 1307, 1294, 1252, 1223, 1190, 1177, 1156, 1096, 979, 862, 835, 775, 666, 608, 555. MALDI-MS (C$_{32}$H$_{40}$F$_2$N$_2$O$_4$SSi): [MH−TBDMSOH]$^+$ 483.1559 (calcd. 483.1554); [MNa]$^+$ 637.2330 (calcd. 637.2344).

The tosylate received above was dissolved in anhydrous DMF (2.5 mL), hydroquinone (263 mg, 2.39 mmol) and Cs$_2$CO$_3$ (102.1 mg, 0.313 mmol) were added and the suspension was stirred at 80° C. for 12 h. EtOAc (30 mL) was added and the organic phase was washed with sat. aq. NaHCO$_3$ (10 mL) and H$_2$O (10 mL), evaporated on celite and purified by dry column vacuum chromatography (4.5×2.0 cm) on silica gel eluting with a gradient of 0-30% EtOAc in hexane (v/v) to give the corresponding phenol XIXf (70.9 mg, 86%) as a colourless oil.

$R_f$ (1:3 EtOAc/hexane (v/v)) 0.33; $^1$H-NMR (300 MHz, CDCl$_3$) δ: 7.24 (2H, dd, J=5.3, 8.4 Hz), 7.06-6.93 (6H, m), 6.75-6.68 (5H, m), 4.67 (1H, dd, J=4.4, 6.8 Hz), 4.10-3.98 (2H, m), 3.74 (1H, dd, J=1.2, 7.5 Hz), 3.17-3.11 (1H, m), 1.86-1.54 (4H, m), 0.88 (9H, s), 0.02 (3H, s), −0.15 (3H, s). $^{13}$C-NMR (75 MHz, CDCl$_3$) δ: 163.32, 160.08, 158.48, 155.35, 152.31, 149.86 (C), 143.85 (CH), 141.52, 141.49, 140.63 (C), 127.23, 127.12, 115.99, 115.73, 115.51, 115.44, 115.04, 114.75, 114.67, 114.57, 73.78 (CH), 67.79 (CH$_2$), 63.88, 51.51 (CH), 37.77, 28.38 (CH$_2$), 25.89 (CH$_3$), 18.25 (C), −4.46, −4.80 (CH$_3$). $^{19}$F (282 MHz, CDCl$_3$) δ: −115.31 (1F, m), −124.71 (1F, septet, J=4.3 Hz). IR (cm$^{-1}$): 3350, 3056, 2953, 2930, 2885, 2858, 1605, 1509, 1472, 1462, 1362, 1297, 1226, 1156, 1100, 1086, 1050, 1006, 939, 828, 776, 667, 609, 553, 518. MALDI-MS (C$_{31}$H$_{38}$F$_2$N$_2$O$_3$Si): [MH−TBDMSOH]$^+$ 421.1720 (calcd. 421.1728); [MH]$^+$ 553.2677 (calcd. 553.2698); [MNa]+575.2505 (calcd. 575.2517).

The phenol XIXf (18.4 mg, 0.0333 mmol) was dissolved in anhydrous THF (1.0 mL, teflon bottle) at 0° C., anhydrous pyridine (0.20 mL) followed by HF-pyridine complex (0.20 mL) were added and the solution was allowed to warm to room temperature over several h and stirred at room temperature for 22 h. Ether (20 mL) was added and the solution was washed with sat. aq. NaHCO$_3$ (2×5 mL), evaporated on celite and purified by dry column vacuum chromatography (4.5×2.0 cm) on silica gel eluting with a gradient of 0-60% EtOAc in hexane (v/v) to give the desired diol XIX (14.4 mg, 99%) as a colourless oil.

$R_f$ (1:1 EtOAc/hexane (v/v)) 0.27; $^1$H-NMR (300 MHz, CDCl$_3$) δ: 7.29 (2H, dd, J=5.3, 8.4 Hz), 7.06-6.93 (6H, m), 6.75-6.67 (5H, m), 4.70 (1H, t, J=6.5 Hz), 4.09-4.03 (2H, m), 3.72 (1H, t, J=10.0 Hz), 3.18 (1H, dd, J=4.4, 6.2 Hz), 1.99- 1.50 (4H, m). $^{13}$C-NMR (75 MHz, CDCl$_3$) δ: 163.72, 160.47, 155.31, 152.26, 149.95 (C), 143.53 (CH), 141.41, 139.78 (C), 127.41, 127.29, 116.01, 115.77, 115.51, 115.23, 114.54, 114.42, 73.49 (CH), 67.60 (CH$_2$), 63.67, 51.35 (CH), 35.89, 28.70 (CH$_2$). $^{19}$F (282 MHz, CDCl$_3$) δ: −114.89 (1F, septet, J=4.3 Hz), −124.64 (1F, septet, J=4.3 Hz). IR (cm$^{-1}$): 3320, 2927, 1604, 1508, 1453, 1366, 1225, 1157, 1102, 1044, 910, 826, 733, 609. MALDI-MS (C$_{25}$H$_{24}$F$_2$N$_2$O$_3$) [MH−H$_2$O]$^+$ 421.1717 (calcd. 421.1728); [M]$^+$ 438.1755 (calcd. 438.1755); [MH] 439.1825 (calcd. 439.1833); [MNa]$^+$ 461.1650 (calcd. 461.1653).

Example 16

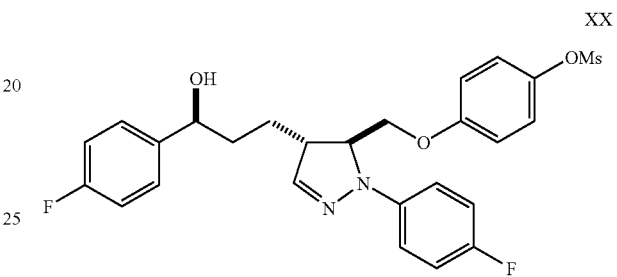

XX

The phenol XIXf obtained in step 15a) (28.4 mg, 0.0514 mmol) was dissolved in anhydrous CH$_2$Cl$_2$ (2 mL), anhydrous pyridine (0.10 mL, 1.3 mmol) and MsCl (0.05 mL, 0.51 mmol) were added and the solution was stirred at room temperature for 22.5 h, evaporated on celite and purified by dry column vacuum chromatography (4.5×2.0 cm) on silica gel eluting with a gradient of 0-50% EtOAc in hexane (v/v) to give the corresponding mesylate (29.2 mg, 90%) as a colourless oil.

$R_f$ (1:1 EtOAc/hexane (v/v)) 0.64; $^1$H-NMR (300 MHz, CDCl$_3$) δ: 7.26-7.17 (6H, m), 7.06-6.94 (6H, m), 6.83 (2H, d, J=9.3 Hz), 6.71 (1H, d, J=1.2 Hz), 4.66 (1H, dd, J=4.4, 6.8 Hz), 4.11 (1H, dd, J=4.0, 9.0 Hz), 4.04 (1H, dt, J=4.4, 7.5 Hz), 3.81 (1H, dd, J=7.5, 8.7 Hz), 3.11 (3H, s), 3.19-3.08 (1H, m), 1.85-1.52 (4H, m), 0.87 (9H, s), 0.01 (3H, s), −0.16 (3H, s). $^{13}$C-NMR (75 MHz, CDCl$_3$) δ: 160.25, 158.65, 157.92, 157.23, 155.50 (C), 143.67 (CH), 142.93, 141.52, 140.67 (C), 127.30, 127.19, 123.18, 115.85, 115.56, 115.45, 115.14, 114.85, 114.64, 114.53, 73.76 (CH), 67.53 (CH$_2$), 63.54, 51.60 (CH), 37.75 (CH$_2$), 37.09 (CH$_3$), 28.29 (CH$_2$), 25.78 (CH$_3$), 18.13 (C), −4.63, −4.98 (CH$_3$). $^{19}$F (282 MHz, CDCl$_3$) δ: −116.00 (1F, m), −125.47 (1F, septet, J=4.3 Hz). IR (cm$^{-1}$): 2930, 2857, 1605, 1508, 1472, 1369, 1299, 1251, 1223, 1197, 1168, 1152, 1086, 1009, 970, 868, 836, 776, 609, 527. MALDI-MS (C$_{32}$H$_{40}$F$_2$N$_2$O$_5$SSi) [MH−TBDMSOH]$^+$ 499.1504 (calcd. 499.1503); [MNa]$^+$ 653.2298 (calcd. 653.2293).

This mesylate (29.0 mg, 0.0460 mmol) was dissolved in anhydrous THF (1.0 mL, teflon bottle) at 0° C., anhydrous pyridine (0.20 mL) followed by HF-pyridine complex (0.20 mL) were added and the solution was allowed to warm to room temperature over several h and stirred at room temperature for 10 h. Ether (20 mL) was added and the solution was washed with sat. aq. NaHCO$_3$ (2×5 mL), evaporated on celite and purified by dry column vacuum chromatography (4.6× 2.0 cm) on silica gel eluting with a gradient of 0-90% EtOAc in hexane (v/v) to give the desired mesylate XX (23.0 mg, 97%) as a colourless oil.

R$_f$ (1:1 EtOAc/hexane (v/v)) 0.18; $^1$H-NMR (300 MHz, CDCl$_3$) δ: 7.30 (2H, dd, J=5.6, 8.7 Hz), 7.18 (2H, d, J=9.3 Hz), 7.06-6.94 (6H, m), 6.83 (2H, d, J=9.3 Hz), 6.73 (1H, d, J=1.2 Hz), 4.70 (1H, dd, J=5.6, 6.8 Hz), 4.14-4.07 (2H, m), 3.84-3.77 (1H, m), 3.19-3.14 (1H, m), 3.10 (3H, s), 1.94 (1H, bs), 1.92-1.54 (4H, m). $^{13}$C-NMR (75 MHz, CDCl$_3$) δ: 163.72, 160.47, 158.50, 157.04, 155.35 (C), 143.35 (CH), 142.82, 141.30, 141.26, 139.84 (C), 127.36, 127.26, 123.11, 115.81, 115.52, 115.41, 115.25, 114.52, 114.42, 73.44 (CH), 67.37 (CH$_2$), 63.44, 51.43 (CH), 37.20 (CH$_3$), 35.97, 28.73 (CH$_2$). $^{19}$F (282 MHz, CDCl$_3$) δ: −114.06 (1F, m), −124.49 (1F, septet, J=4.3 Hz). IR (cm$^{-1}$): 3550, 3404, 2936, 1604, 1508, 1366, 1299, 1249, 1223, 1196, 1168, 1151, 1039, 970, 913, 870, 835, 743, 528. MALDI-MS (C$_{26}$H$_{26}$F$_2$N$_2$O$_5$S): [MH—H$_2$O]$^+$ 499.1500 (calcd. 499.1503); [M]$^+$ 516.1536 (calcd. 516.1504); [MH]$^+$ 517.1606 (calcd. 517.1609); [MNa]$^+$ 539.1428 (calcd. 539.1428).

Example 17 trated in vacuo. The residue is purified by chromatography on silica gel eluting with hexane/ethyl acetate (3/2 to 1/2 gradient) and then chromatography on silica gel eluting with EtOAc/CH$_2$Cl$_2$ (7/1 to 3/1 gradient) to afford β-lactam XXIc as a colorless solid in 40% yield along with 35% yield of the undesired diastereomer.

mp: 132° C. R$_f$=0.38 (hexane/ethyl acetate 1/1). α$_D$=+77°, (CHCl$_3$, c=1.075, 30.5° C.). $^1$H-NMR (300 MHz, CDCl$_3$): δ 7.46-7.07 (m, 16H), 6.92-6.84 (m, 2H), 5.34 (d, J=5.3 Hz, 1H), 5.06 (s, 2H), 4.95 (d, J=5.3 Hz, 1H), 4.60 (d, J=2.5 Hz), 3.23-3.14 (m, 1H), 2.90 (s, 3H), 1.70 (s, 3H), 0.83 (d, J=6.2 Hz) $^{13}$C-NMR (75 MHz, CDCl$_3$): δ 165.4, 165.0, 159.3 (J=244 Hz), 159.1, 137.1 (J=5 Hz), 133.7, 129.9, 128.9, 128.6, 128.3, 128.0, 127.7, 125.7, 119.0 (J=8 Hz), 116.0 (J=23 Hz), 115.1, 100.1, 76.9, 71.2, 70.1, 62.2, 59.0, 33.8, 23.6, 12.4. IR (thin film): 2938, 1756, 1667, 1612, 1511, 1382, 1223, 1177, 1112, 1092, 834, 734. HRMS (EI): Calcd' for (C$_{35}$H$_{33}$FN$_2$O$_5$$^+$), 580.2374, found, 580.2369.

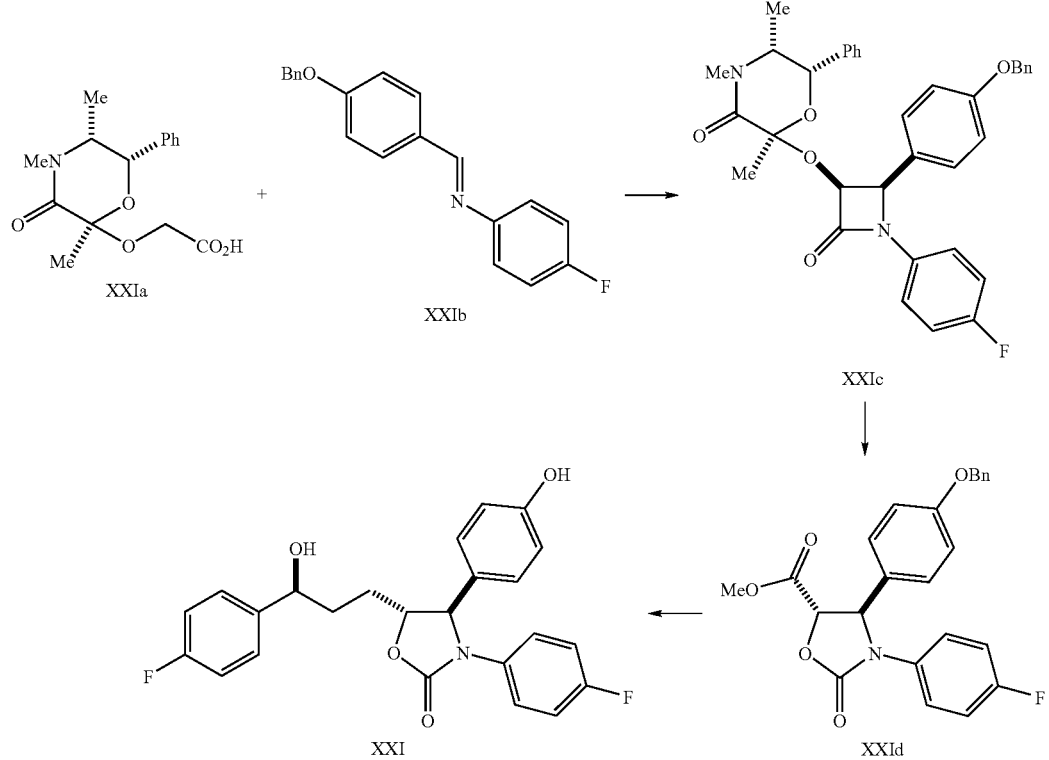

To a solution of acid XXIa (prepared according to B. A. Shinkre, V. G. Puranik, B. M. Bhawal, A. Deshmukh, *Tetrahedron: Asymmetry* 2003, 14, 453; 30.0 g, 102 mmol, 1.11 equiv) in CH$_2$Cl$_2$ (600 ml) is added triethylamine (64.0 ml, 461 mmol, 5.00 equiv) followed by imine XXIb (prepared according to T. Kambara, K. Tomioka, *J. Org. Chem.* 1999, 64, 9282; 28.1 g, 92.1 mmol, 1.00 equiv). The solution is cooled to −20° C. and triphosgene (16.4 g, 55.8 mmol, 0.600 equiv) is added in 50 ml CH$_2$Cl$_2$ over a period of 20 min. The solution is warmed to 23° C. over a period of 8 h and stirred for additional 10 h at this temperature. The solution is poured onto 600 ml ice water and 200 ml CH$_2$Cl$_2$. The aqueous phase is extracted with CH$_2$Cl$_2$ (3*100 ml). The combined organic phases are washed with brine, dried (Na$_2$SO$_4$) and concen- To a solution of β-lactam XXIc (17.0 g, 29.0 mmol, 1.00 equiv) in THF (242 ml) and water (48 ml) is added p-toluenesulfonic acid hydrate (55.7 g, 293 mmol, 10.0 equiv). The solution is heated to reflux for 5 h. The solution is concentrated to an approximate volume of 60 ml and then poured onto EtOAc (150 ml) and water (250 ml). The aqueous phase is extracted with EtOAc (4*100 ml). The combined organic phases are washed with brine, dried (Na$_2$SO$_4$) and concentrated in vacuo. The residue is purified by chromatography on silica gel eluting with hexane/ethyl acetate (3/2 to 2/3 gradient) to afford the corresponding 3-hydroxy-β-lactam as a colorless solid in 51% yield.

mp: 168° C. $R_f$=0.26 (hexane/ethyl acetate 3/2). $\alpha_D$=−129°, (acetone, c=1.22, 29.5° C.). $^1$H-NMR (300 MHz, acetone): δ 7.50-7.47 (m, 2H), 7.42-7.29 (m, 5H), 7.10-7.01 (m, 4H), 5.33 (d, J=5.3 Hz, 1H), 5.27 (dd, J=7.2 Hz, 5.3 Hz, 1H), 5.11 (s, 2H), 5.07 (d, J=7.2 Hz, 1H). $^{13}$C-NMR (75 MHz, acetone): δ 166.5, 159.2, 159.0 (J=241 Hz), 137.7, 134.7, 129.6, 128.6, 128.0, 127.8, 118.9 (J=8 Hz), 115.8 (J=23 Hz), 114.8, 78.0, 69.8, 62.3. IR (thin film): 3120, 1756, 1667, 1612, 1511, 1382, 1223, 1177, 1112, 1092, 834, 734. HRMS (EI): Calcd' for ($C_{22}H_{18}FNO_3^+$), 363.1271, found, 363.1268. Anal. Calcd. for $C_{22}H_{18}FNO_3$: C, 72.72; H, 4.99; N, 3.85; found: C, 77.73; H, 5.20; N, 3.91.

To a suspension of this 3-hydroxy-β-lactam (2.00 g, 5.50 mmol, 1.00 equiv) in methanol (55.0 ml) is added sodium methoxide (1.49 g, 27.5 mmol, 5.00 equiv). The suspension is stirred at 23° C. for 2 h. To the forming solution is added $NH_4Cl_{(s)}$ and the suspension is concentrated in vacuo. To the solid is added EtOAc (50 ml) and water (50 ml). The aqueous phase is extracted with EtOAc (3*20 ml). The combined organic phases are washed with brine, dried ($Na_2SO_4$) and concentrated in vacuo. The residue is purified by chromatography on silica gel eluting with hexane/ethyl acetate (3/2 to 1/1 gradient) to afford the corresponding amino alcohol as a colorless solid in 89% yield.

mp: 103° C. $R_f$=0.45 (hexane/ethyl acetate 3/2). $\alpha_D$=+13.9°, ($CH_2Cl_2$, c=1.10, 25.3° C. $^1$H-NMR (300 MHz, CDCl$_3$): δ 7.44-7.24 (m, 4H), 6.97-6.91 (m, 2H), 6.84-6.76 (m, 2H), 6.53-6.46 (m, 2H), 5.02 (s, 2H), 4.81 (s, 1H), 4.60 (s, 1H), 4.46 (m, 1H), 3.79 (s, 3H), 3.07 (d, J=3.7 Hz, 1H). $^{13}$C-NMR (75 MHz, CDCl$_3$): δ 158.2, 155.8 (J=233 Hz), 142.5, 136.8, 131.0, 128.5, 127.9, 127.9, 127.4, 155.5 (J=22 Hz), 114.9, 114.8, 74.6, 70.0, 59.1, 53.1, 114.8, 78.0, 69.8, 62.3. IR (thin film): 3390, 1737, 1610, 1510, 1221, 1113, 823. MS (EI): 306.1748 (2.54%), 186.2356 (18.8%), 91.0908 (100%). Anal. Calcd. for $C_{23}H_{22}FNO_4$: C, 69.86; H, 5.61; N, 3.54; found: C, 69.88; H, 5.78; N, 3.54.

To a solution of the amino alcohol received above (1.92 g, 4.86 mmol, 1.00 equiv) in $CH_2Cl_2$ (24.0 ml) is added diisopropylethylamine (2.54 ml, 14.6 mmol, 3.00 equiv) and 4-N,N-dimethylaminopyridine (59.0 mg, 0.486 mmol, 0.10 equiv). The solution is cooled to −78° C. and triphosgene (1.44 g, 4.86 mmol, 1.00 equiv) in $CH_2Cl_2$ (4.0 ml) is added over a period of 5 min. The solution is warmed to 23° C. over 8 h and stirred at this temperature for additional 5 h. To this solution is added water (50 ml) and concentrated aqueous ammonium hydroxide solution (3 ml). The aqueous phase is extracted with $CH_2Cl_2$ (3*20 ml). The combined organic phases are washed with brine, dried ($Na_2SO_4$) and concentrated in vacuo. The residue is purified by chromatography on silica gel eluting with hexane/ethyl acetate (2/1 to 1/1 gradient) to afford methyl ester XXId as a colourless solid in 82% yield.

mp: 118° C. $R_f$=0.54 (hexane/ethyl acetate 3/2). $\alpha_D$=+18°, (CHCl$_3$, c=1.10, 29.3° C.). $^1$H-NMR (300 MHz, CDCl$_3$): δ 7.40-7.32 (m, 7H), 7.29-7.22 (m, 2H), 6.98-6.93 (m, 4H), 5.33 (d, J=4.4 Hz, 1H), 5.03 (s, 2H), 4.73 (d, J=4.4 Hz, 1H), 3.89 (s, 3H). $^{13}$C-NMR (75 MHz, CDCl$_3$): δ 168.9, 160.1 (d, J=244 Hz), 159.7, 154.3, 136.7, 132.7, 129.5, 128.9, 128.4, 127.8, 127.7, 123.2 (d, J=8 Hz), 116.1 (d, J=22 Hz), 116.0, 77.9, 70.3, 36.6, 53.5. IR (thin film): 1769, 1552, 1388, 1227, 1099, 834. HRMS (MALDI): Calcd' for ($C_{24}H_{20}FNO_5Na^+$), 444.1224, found, 444.1224. Anal. Calcd. for $C_{24}H_{20}FNO_5$: C, 68.40; H. 4.78; N, 3.32; found: C, 68.18; H, 4.91; N, 3.38.

To a suspension of methyl ester XXId (1.68 g, 3.99 mmol, 1.00 equiv) in ethanol (27.0 ml) is added at 23° C. sodium cyanoborohydride (226 mg, 5.98 mmol, 1.50 equiv). The suspension is stirred for 2 h at this temperature at which point all solids were dissolved. To this solution is added $NH_4Cl_{(s)}$ and the volume is concentrated in vacuo to 5 ml. To this suspension is added water (50 ml) and EtOAc (50 ml). The aqueous phase is extracted with EtOAc. The combined organic phases are washed with brine, dried ($Na_2SO_4$) and concentrated in vacuo. The residue is purified by chromatography on silica gel eluting with hexane/ethyl acetate (1/1 to 2/3 gradient) to afford the corresponding alcohol as a colorless solid in 92% yield.

mp: 143° C. $R_f$=0.40 (hexane/ethyl acetate 2/3). $\alpha_D$=−16°, (CHCl$_3$, c=1.54, 32.4° C.). $^1$H-NMR (300 MHz, CDCl$_3$): δ 7.42-7.19 (m, 9H), 6.97-6.90 (m, 4H), 5.26 (d, J=6.5 Hz, 1H), 5.02 (s, 2H), 4.39 (m, 1H), 3.99 (d, J=12.5 Hz, 1H), 3.74 (d, J=12.5 Hz, 1H), 2.77 (s, 1H). $^{13}$C-NMR (75 MHz, CDCl$_3$): δ 159.7 (d, J=245 Hz), 159.0, 136.4, 132.7, 129.4, 128.5, 128.0, 127.9, 127.4, 123.6 (d, J=8 Hz), 115.6 (d, J=22 Hz), 115.6, 82.0, 70.1, 61.6, 61.2. IR (thin film): 3418, 2930, 2871, 1748, 1611, 1512, 1394, 1234. HRMS (EI): Calcd' for ($C_{23}H_{20}FNO_4^+$), 393.1376, found, 393.1389. Anal. Calcd. for $C_{23}H_{20}FNO_4$: C, 70.22; H, 5.12; N, 3.56; found: C, 70.26; H, 5.21; N, 3.61.

To a solution of oxalylchloride (508 mg, 4.00 mmol, 2.00 equiv) in $CH_2Cl_2$ (15.0 ml) is added at −78° C. dimethylsulfoxide (0.355 ml, 5.00 mmol, 2.50 equiv). After 10 min at −78° C. is added the alcohol received above (787 mg, 2.00 mmol, 1.00 equiv) in $CH_2Cl_2$ (15.0 ml) over a period of 5 min. After additional 5 min at this temperature triethylamine (1.14 ml, 8.00 mmol, 8.00 equiv) is added. After 5 min 1-(4-Fluorophenyl)-2-(triphenyl-$\lambda^5$-phosphanylidene)-ethanone is added and the resulting suspension is warmed to 20° C. and stirred for additional 30 min. To the solution is added saturated aqueous $Na_2HCO_3$ solution. The aqueous phase is extracted with $CH_2Cl_2$. The combined organic phases are washed with brine, dried ($Na_2SO_4$) and concentrated in vacuo. The residue is purified by chromatography on silica gel eluting with hexane/ethyl acetate (2/1 to 1/1 gradient) to afford the corresponding enone as a colorless solid in 89% yield.

mp: 152° C. $R_f$=0.56 (hexane/ethyl acetate 3/2). $\alpha_D$=+1000, (CHCl$_3$, c=0.60, 25.6° C.). $^1$H-NMR (300 MHz, CDCl$_3$): δ 8.06-7.99 (m, 2H), 7.42-7.06 (m, 14H), 7.00-6.92 (m, 4H), 5.05-5.00 (m, 4H). $^{13}$C-NMR (75 MHz, CDCl$_3$): δ 187.1, 165.9 (d, J=254 Hz), 159.8 (d, J=243 Hz), 159.4, 154.8, 140.0, 136.2, 133.2, 132.3, 131.4 (d, J=9 Hz), 128.6, 128.1, 128.1, 127.9, 127.4, 125.8, 123.5 (d, J=9 Hz), 115.9 (d, J=24 Hz), 115.8 (d, J=24 Hz), 115.8, 80.5, 70.2, 66.0. IR (thin film): 1760, 1675, 1597, 1511, 1385, 1227. HRMS (MALDI): Calcd' for ($C_{33}H_{23}F_2NO_4Na^+$), 534.1493, found, 534.1482. Anal. Calcd. for $C_{31}H_{23}F_2NO_4$: C, 72.79; H, 4.53; N, 2.74; found: C, 72.51; H, 4.78; N, 2.73.

To this enone (910 mg, 1.78 mmol, 1.00 equiv) in ethanol (15.0 ml) is added at 23° C. palladium on carbon (10%) (100 mg). The suspension is vigorously stirred under 1 atm of hydrogen gas for 3 h. The suspension is filtered through a pad of celite eluting with EtOAc concentrated and the residue is purified by chromatography on silica gel eluting with hexane/ethyl acetate (2/1 to 1/1 gradient). A portion of the resulting benzyl ether (310 mg, 0.604 mmol, 1.00 equiv) is dissolved in $CH_2Cl_2$ and cooled to −20° C. (R)-3,3-diphenyl-1-methyltetrahydro-0.3H-pyrrolo-oxazaborole2-methyl-oxazaborolidin (solution in toluene (0.5 M) 0.600 ml, 0.302 mmol, 0.50 equiv) is added followed by borane dimethylsulfide complex (0.080 ml, 0.905 mmol, 1.50 equiv). The solution is stirred at −20° C. for 2 h, then warmed to 0° C. and quenched with methanol. To the solution is added saturated aqueous $Na_2HCO_3$ solution and $CH_2Cl_2$. The aqueous phase is extracted with $CH_2Cl_2$. The combined organic phases are washed with brine, dried (Na$_2$SO$_4$) and concentrated in vacuo. The residue is purified by chromatography on silica gel eluting with hexane/ethyl acetate (3/2 to 1/1 gradient). A portion of the resulting alcohol (53 mg, 0.10 mmol, 1.0 equiv) is dissolved in ethanol and palladium on carbon (10 mg) is added. The suspension is vigorously stirred under an atmosphere of hydrogen for 2.5 h. The suspension is filtered through a plug of celite eluting with EtOAc. The residue is purified by chromatography on silica gel eluting with hexane/ethyl acetate (1/1 to 1/2 gradient) to afford the desired oxazolidinone XXI as a colorless solid in 57% yield from the starting enone.

mp: 98° C. R$_f$=0.41 (hexane/ethyl acetate 2/3). α$_D$=−1°, (CHCl$_3$, c=0.84, 27.6° C.). $^1$H-NMR (300 MHz, acetone d$_6$): δ 7.47-7.35 (m, 4H), 7.29-7.24 (m, 2H), 7.09-6.97 (m, 4H), 6.85-6.79 (m, 2H), 5.15 (d, J=6.7 Hz, 1H), 4.76-4.68 (m, 1H), 4.43-4.34 (m, 2H), 2.02-1.76 (m, 4H). $^{13}$C-NMR (75 MHz, acetone d$_6$): δ 162.0 (d, J=243 Hz), 159.5 (d, J=242 Hz), 157.9, 155.3, 142.2 (d, J=3 Hz), 134.3 (d, J=2 Hz), 129.1, 128.7, 127.8 (d, J=8 Hz), 123.8 (d, J=9 Hz), 116.1, 115.2 (d, J=23 Hz), 114.9 (d, J=21 Hz), 82.4, 72.3, 65.6, 35.0, 30.3. IR (thin film): 3316, 2925, 1726, 1603, 1511, 1224, 835. HRMS (MALDI): Calcd' for (C$_{24}$H$_{21}$F$_2$NO$_4$Na$^+$), 448.1337, found, 448.1326.

Example 18

The compounds of the invention and ezetimibe (commercially obtained or prepared according to Wu, G. Z. et al., *J. Org. Chem.* 1999) together with the glucuronide (the metabolite of ezetimibe, prepared according to Vaccaro, W. D.; Davis, H. R. *Bioorg. Med. Chem. Lett.* 1998, 8, 313-318) as appropriate reference compounds were evaluated by well-established methods to determine their inhibition of cholesterol uptake in rabbit brush border membrane vesicles (BBMV) (Table 1). Briefly, the scavenger receptor-mediated uptake of radiolabelled cholesterol ester from the loaded donor particles into the BBMV bilayer was measured in the presence of various compounds of the invention and appropriate reference compounds (Hauser, H. et al., *Biochemistry* 1998, 37, 17843-17850; Werder, M. et al., *Biochemistry* 2001, 40, 11643-11650; Boffelli, D. et al., *FEBS Lett.* 1997, 411, 7-11.)

TABLE 1

| Compound | applied in donor SUV (9 mol %) Inhibition in (%) |
|---|---|
| Ezetimibe | 16 ± 4 |
| Glucuronide | 19 ± 4 |
| VI | 30 ± 4 |
| VII | 22 ± 2 |
| VIII | 15 ± 3 |
| IXb | 20 ± 5 |
| IX | 27 ± 4 |
| X | 15 ± 3 |
| XI | 20 ± 5 |
| XIV | 26 ± 3 |
| XV | 19 ± 3 |
| XVI | 21 ± 5 |
| XVII | 28 ± 4 |
| XVIII | 41 ± 4 |
| XXI | 19 ± 2 |

The invention claimed is:
1. A compound according to formula I

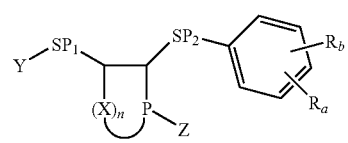

wherein
P represents —N<,
(X)$_n$ represents —OOC—, —COO—, —CONH—, —CH=N—,
R$_a$ represents H, lower alkyl, —OR$_3$, —O(CO)R$_3$, —O(CO)OR$_3$, —O(CO)NR$_3$R$_4$, —N$_3$R$_4$, —NR$_3$(CO)R$_4$, —COOR$_3$, —CONR$_3$R$_4$, —CH=CHCOOR$_3$, —CF$_3$, —CN, —NO$_2$, SO$_3$H, PO$_3$H or halogen,
wherein
R$_3$ and R$_4$ represent H or lower alkyl,
R$_b$ represents H, OH, —OSO$_2$Me, —OSO$_2$W
wherein
W represents optionally substituted aryl or heteroaryl, —OCO(CHOH)$_2$COOR$_5$
wherein
R$_5$ represents H or lower alkyl; or represents the formula -Sp$_3$—R$_6$,
wherein
Sp$_3$ represents a covalent bond, —O—, —OCH$_2$—, —OSO$_2$CH$_2$—, —OSO$_2$—, —OSO$_2$— (p) C$_6$H$_4$O— and
R$_6$ represents one of carbohydrate structures A-D:

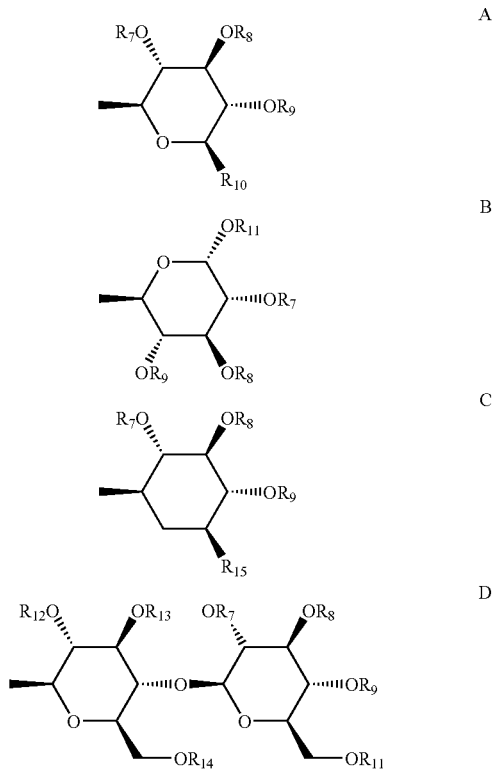

wherein
R$_7$, R$_8$, R$_9$, R$_{11}$, R$_{12}$, R$_{13}$ and R$_{14}$ represent independently of each other H, lower alkyl, aryl(lower alkyl), —CO-lower alkyl, —CO-aryl, —SO$_3^-$ or —PO$_3^-$,
R$_{10}$ represents —CH$_2$OR$_{16}$ or —COOR$_{17}$, and
R$_{15}$ represents —CH$_2$OR$_{16}$, —COOR$_{17}$, —CH$_2$NH$_2$, —CH$_2$OPO$_3^-$ or —CH$_2$OSO$_3^-$, wherein
R$_{16}$ and R$_{17}$ independently of each other represent H, lower alkyl, aryl (lower alkyl), —CO-lower alkyl, —CO-aryl, —SO$_3^-$ or —PO$_3^-$,
Z represents optionally substituted aryl or heteroaryl,
Sp$_1$ represents lower alkyl group —(CH$_2$)$_p$—, wherein p is from 2-6, which is mono or poly-substituted by —OH, —OR$_{18}$, halogen or cyano group, wherein one or more —CH$_2$— groups may independently be replaced by —O—, —CO—, —CO—O—, —O—CO—, —NR$_{19}$—, —NR$_{19}$—CO—, —CO—NR$_{19}$—, —CH═CH—, —C≡C— and wherein R$_{18}$ and R$_{19}$ represent a hydrogen atom or lower alkyl,
Sp$_2$ represents a covalent bond or a lower alkyl group —(CH$_2$)$_q$—, wherein q is from 1-6, which is unsubstituted, mono or poly-substituted by —OH, —OR$_{20}$, halogen or cyano group, wherein one or more —CH$_2$— groups may independently be replaced by —O—, —CO—, —CO—O—, —O—CO—, —NR$_{21}$—, —NR$_{21}$—CO—, —CO—NR$_{21}$—, —CH═CH—, —C≡C— and wherein R$_{20}$, and R$_{21}$, represents a hydrogen atom or lower alkyl,
Y represents optionally substituted aryl or heteroaryl.

2. A compound according to claim 1 having the formula IVa

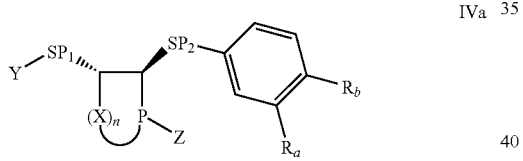

wherein P is —N═ and (X)$_n$ is —OOC—, —COO—, —CONH, —CH═N—, and R$_a$, R$_b$, Sp$_1$, Sp$_2$, Y, Z and n are as defined in claim 1.

3. A compound according to claim 1 having the formula IVb,

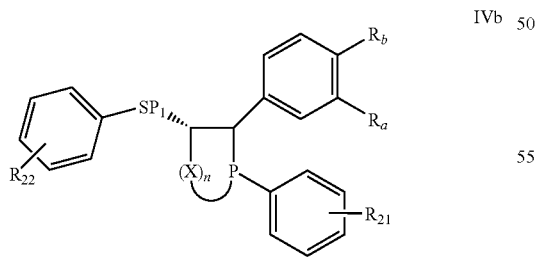

wherein P is —N═ and (X)$_n$ is —OOC—, —COO—, —CONH, —CH═N—, and R$_a$, R$_b$, Sp$_1$, are as defined hereinabove and wherein R$_{21}$ and R$_{22}$ represent H, lower alkyl, lower alkoxy or halogen.

4. A pharmaceutical composition comprising a therapeutically effective amount of a compound of claim 1 with a pharmaceutically acceptable carrier.

5. A pharmaceutical composition according to claim 4 for the treatment of arteriosclerosis or for the reduction of cholesterol levels.

6. A kit comprising a pharmaceutical composition according to claim 4 for use in the treatment of arteriosclerosis or for the reduction of cholesterol levels.

7. A method for the treatment of arteriosclerosis or for the reduction of cholesterol levels comprising administering to a subject in need of such treatment an effective amount of a compound according to claim 1.

8. A compound according to claim 1 having the formula IIIa or formula IIId

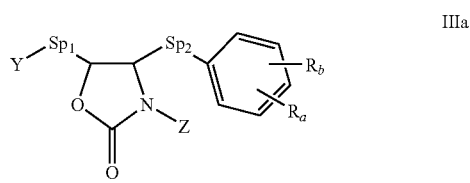

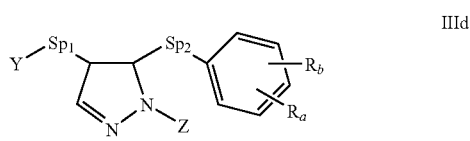

wherein,
R$_a$ represents H straight chain or branched C(1-8)alkyl, —OR$_3$, —NR$_3$R$_4$, —COOR$_3$, —CONR$_3$R$_4$, —CH═CHCOOR$_3$, —CF$_3$, —CN, —NO$_2$, SO$_3$H, PO$_3$H or halogen, wherein R$_3$ and R$_4$ represent independently of each other H or straight chain or branched C(1-8)alkyl,
R$_b$ represents H, OH, —OSO$_2$Me, —OSO$_2$W wherein W represents optionally substituted aryl or heteroaryl, OCO(CHOH)$_2$COOR$_5$ wherein R$_5$ represents H or straight chain or branched C(1-8)alkyl; or represents the formula -Sp$_3$-R$_6$,
wherein
Sp$_3$ represents a covalent bond, —O—, —OCH$_2$—, —OSO$_2$CH$_2$—, —OSO$_2$-(p)C$_6$H$_4$O— and R$_6$ represents one of carbohydrate structures A-D:

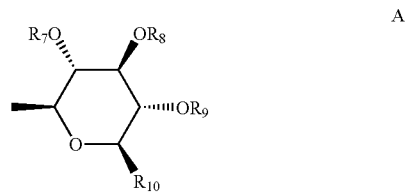

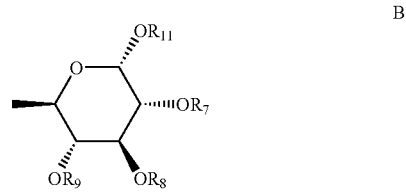

-continued

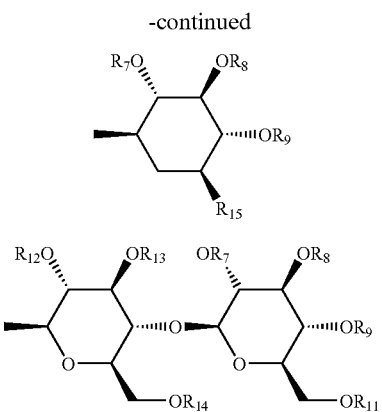

C

D wherein, $R_7$, $R_8$, $R_9$, $R_{11}$, $R_{12}$, $R_{13}$ and $R_{14}$ represent independently of each other H, straight chain or branched C(1-8)alkyl, aryl(C(1-8)alkyl), —CO— (C(1-8)alkyl), —CO-aryl, —SO$_3$— or —PO$_3$—, $R_{10}$ represents —CH$_2$OR$_{16}$ or —COOR$_{17}$, and $R_{15}$ represents —CH$_2$OR$_{16}$, COOR$_{17}$, —CH$_2$NH$_2$—, CH$_2$OPO$_3$— or —CH$_2$OSO$_3$—, wherein $R_{16}$ and $R_{17}$ independently of each other represents H, straight chain or branched C(1-8)alkyl, aryl (C(1-8) alkyl), —CO—(C(1-8)alkyl), —CO-aryl, —SO$_3$— or —PO$_3$—, Z represents optionally substituted aryl, $Sp_1$ represents a straight chain or branched alkyl group —(CH$_2$)$_p$—, wherein p is from 2-6, which is mono or poly-substituted by —OH, —OR$_{18}$, halogen or cyano group, wherein one or more —CH$_2$— groups may independently be replaced by —O—, —CO—, —CO—O—, —O—CO—, —NR$_{19}$—, —NR$_{19}$—CO—, —CO—NR$_{19}$—, —CH=CH—, —C≡C—, and wherein $R_{18}$ and $R_{19}$ represent a hydrogen atom or straight chain or branched C(1-8)alkyl, $Sp_2$ represents a covalent bond, Y represents optionally substituted aryl.

9. A compound according to claim 8 wherein $R_a$ is in the meta-position and $R_b$ is in the para-position.

10. A compound according to claim 8 wherein $R_a$ is H, straight chain or branched C(1-8)alkyl, —OR$_3$, —NR$_3$R$_4$, —COOR$_3$, —CONR$_3$R$_4$ or halogen, wherein $R_3$ and $R_4$ represent independently of each other H or straight chain or branched C(1-8)alkyl.

11. A compound according to claim 8 wherein $R_b$ is H, OH, —OSO$_2$Me, OSO$_2$Ph; or the formula -Sp$_3$-R$_6$, wherein Sp$_3$, preferably represents a covalent bond, —O—, —OCH$_2$— or —OSO$_2$CH$_2$— and R$_6$ represents one of carbohydrate structures A-D, preferably carbohydrate structures A, B or D.

12. A compound according to claim 8 wherein $Sp_1$ represents a lower alkyl —CH$_2$)$_m$— group, which is mono or poly-substituted by —OH, —OR$_{18}$, halogen or cyano group, wherein $R_{18}$ represents hydrogen or straight chain or branched C(1-8) alkyl and m is 1 to 3.

13. A compound according to claim 8 wherein Y represents an optionally substituted phenyl group.

14. A compound according to claim 8 wherein Z represents an optionally substituted phenyl group.

15. A pharmaceutical composition comprising a therapeutically effective amount of a compound of claim 8 with a pharmaceutically acceptable carrier.

16. A pharmaceutical composition according to claim 15 for the treatment of arteriosclerosis or for the reduction of cholesterol levels.

17. A kit comprising a pharmaceutical composition according to claim 15 for use in the treatment of arteriosclerosis or for the reduction of cholesterol levels.

18. A method for the treatment of arteriosclerosis or for the reduction of cholesterol levels comprising administering, to a subject in need of such treatment, an effective amount of a compound according to claim 8.

* * * * *